(12) United States Patent
Gruss et al.

(10) Patent No.: US 8,895,604 B2
(45) Date of Patent: Nov. 25, 2014

(54) SOLID FORMS OF (1R,4R)-6'-FLUORO-N,N-DIMETHY1-4-PHENYL-4',9'-DIHYDRO-3'H-SPIRO-[CYCLOHEXANE-1,1'-PYRANO-[3,4,B]INDOL]-4-AMINE HYDROCHLORIDE

(71) Applicant: Gruenenthal GmbH, Aachen (DE)

(72) Inventors: Michael Gruss, Aachen (DE); Stefan Kluge, Riehen (CH); Andreas Sieber, Glis (CH)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/711,277

(22) Filed: Dec. 11, 2012

(65) Prior Publication Data

US 2013/0150420 A1 Jun. 13, 2013

Related U.S. Application Data

(60) Provisional application No. 61/569,512, filed on Dec. 12, 2011.

(30) Foreign Application Priority Data

Dec. 12, 2011 (EP) .................................. 11009773

(51) Int. Cl.
*C07D 491/107* (2006.01)
*C07D 491/052* (2006.01)

(52) U.S. Cl.
CPC ........ *C07D 491/052* (2013.01); *C07D 491/107* (2013.01)
USPC .......................................... 514/410; 548/421

(58) Field of Classification Search
CPC .................................. C07D 491/107
USPC ....................................... 548/421
See application file for complete search history.

(56) References Cited

U.S. PATENT DOCUMENTS

2011/0015220 A1 1/2011 Linz et al.
2011/0319440 A1 12/2011 Hinze et al.

FOREIGN PATENT DOCUMENTS

WO WO 2004/043967 A1 5/2004
WO WO 2008/040481 A1 4/2008

OTHER PUBLICATIONS

International Search Report including Written Opinion (PCT/ISA/237) dated Jan. 31, 2013 {Nine (9) Pages}.
Hilfiker, Rolf, "Physical Characterization of Hygroscopicity in Pharmaceutical Solids", Polymorphism in the Pharmaceutical Industry, 2006, pp. 235-242, Wiley VCH Verlag GmbH & Co., Weinheim, Germany.
Ravin, L. PhD., "Preformulation", Remington Chapter 76, pp. 1409-1423, 1985 (fifteen (15) sheets).
Disanto, A., "Bioavailability and Bioequivalency Testing", Remington Chapter 77, pp. 1424-1431, 1985 (eight (8) sheets).
Knevel, A. PhD., "Separation", Remington Chapter 78, pp. 1432-1442, 1985 (eleven (11) sheets).
Phillips, G Briggs, PhD., "Sterilization", Remington Chapter 79, pp. 1443-1454, 1985 (twelve (12) sheets).
Siegel, F. PhD., "Tonicity, Osmoticity, Osmolality and Osmolarity", Remington Chapter 80, pp. 1455-1472, 1985 (eighteen (18) sheets).
Giles et al., "Plastic Packaging Materials", Remington Chapter 81, pp. 1473-1477, 1985 (five (5) sheets).
Lintner, C. PhD., "Stability of Pharmaceutical Products", Remington Chapter 82, pp. 1478-1486, 1985 (nine (9) sheets).
Erskine, C., Jr., "Quality Assurance and Control" Remington Chapter 83, pp. 1487-1491, 1985 (five (5) sheets).
Nairn, J.G. PhD., "Solutions, Emulsions, Suspensions and Extractives", Remington Chapter 84, pp. 1492-1517, 1985 (twenty-six (26) sheets).
Avis, K. DSc., "Parenteral Preparations", Remington Chapter 85, pp. 1518-1541, 1985 (twenty-four (24) sheets).
Turco et al., "Intravenous Admixtures", Remington Chapter 86, pp. 1542-1552, 1985 (eleven (11) sheets).
Mullins, J. PhD., "Ophthalmic Preparations", Remington Chapter 87, pp. 1553-1566, 1985 (fourteen (14) sheets).
Block, L. PhD., "Medicated Applications", Remington Chapter 88, pp. 1567-1584, 1985 (eighteen (18) sheets).
Rippie, E. PhD., "Powders", Remington Chapter 89, pp. 1585-1602 (eighteen, 1985 (18) sheets).
King et al., "Oral Solid Dosage Forms", Remington Chapter 90, pp. 1603-1632, 1985 (thirty (30) sheets).
Porter, S. PhD., "Coating of Pharmaceutical Dosage Forms", Remington Chapter 91, pp. 1633-1643, 1985 (eleven (11) sheets).
Longer et al., "Sustained-Release Drug Delivery Systems", Remington Chapter 92, pp. 1644-1661, 1985 (eighteen (18) sheets).
Sclarra et al., "Aerosols", Remington Chapter 93, 1985, pp. 1662-1677, 1985 (sixteen (16) sheets).
Reutzel-Edens et al., "Physical Characterization of Hygroscopicity in Pharmaceutical Solids", Polymorphism in the Pharmaceutical Industry, 2006, pp. 235-242 (ten (10) sheets).
Ravin, L. PhD., "Preformulation", Remington Chapter 76, pp. 1409-1423 (fifteen (15) sheets).
Disanto, A., "Bioavailability and Bioequivalency Testing", Remington Chapter 77, pp. 1424-1431 (eight (8) sheets).
Knevel, A. PhD., "Separation", Remington Chapter 78, pp. 1432-1442 (eleven (11) sheets).
Phillips, G Briggs, PhD., "Sterilization", Remington Chapter 79, pp. 1443-1454 (twelve (12) sheets).
Siegel, F. PhD., "Tonicity, Osmoticity, Osmolality and Osmolarity", Remington Chapter 80, pp. 1455-1472 (eighteen (18) sheets).
Giles et al., "Plastic Packaging Materials", Remington Chapter 81, pp. 1473-1477 (five (5) sheets).
Lintner, C. PhD., "Stability of Pharmaceutical Products", Remington Chapter 82, pp. 1478-1486 (nine (9) sheets).
Erskine, C., Jr., "Quality Assurance and Control" Remington Chapter 83, pp. 1487-1491 (five (5) sheets).
Nairn, J.G. PhD., "Solutions, Emulsions, Suspensions and Extractives", Remington Chapter 84, pp. 1492-1517 (twenty-six (26) sheets).

(Continued)

*Primary Examiner* — Shawquia Young
(74) *Attorney, Agent, or Firm* — Crowell & Moring LLP

(57) ABSTRACT

Solid forms of (1r,4r)-6'-fluoro-N,N-dimethyl-4-phenyl-4',9'-dihydro-3'H-spiro[cyclohexane-1,1'-pyrano[3,4,b]indol]-4-amine hydrochloride, in particular crystalline forms and/or amorphous forms thereof, pharmaceutical compositions and medicaments containing these solid forms, the use of these solid forms, and a process for obtaining such solid forms.

9 Claims, 14 Drawing Sheets

(56) References Cited

OTHER PUBLICATIONS

Avis, K. DSc., "Parenteral Preparations", Remington Chapter 85, pp. 1518-1541 (twenty-four (24) sheets).
Turco et al., "Intravenous Admixtures", Remington Chapter 86, pp. 1542-1552 (eleven (11) sheets).
Mullins, J. PhD., "Ophthalmic Preparations", Remington Chapter 87, pp. 1553-1566 (fourteen (14) sheets).
Block, L. PhD., "Medicated Applications", Remington Chapter 88, pp. 1567-1584 (eighteen (18) sheets).
Rippie, E. PhD., "Powders", Remington Chapter 89, pp. 1585-1602 (eighteen (18) sheets).
King et al., "Oral Solid Dosage Forms", Remington Chapter 90, pp. 1603-1632 (thirty (30) sheets).
Porter, S. PhD., "Coating of Pharmaceutical Dosage Forms", Remington Chapter 91, pp. 1633-1643 (eleven (11) sheets).
Longer et al., "Sustained-Release Drug Delivery Systems", Remington Chapter 92, pp. 1644-1661 (eighteen (18) sheets).
Sclarra et al., "Aerosols", Remington Chapter 93, pp. 1662-1677 (sixteen (16) sheets).
Extended European Search Report dated Mar. 23, 2012 (five (5) sheets).

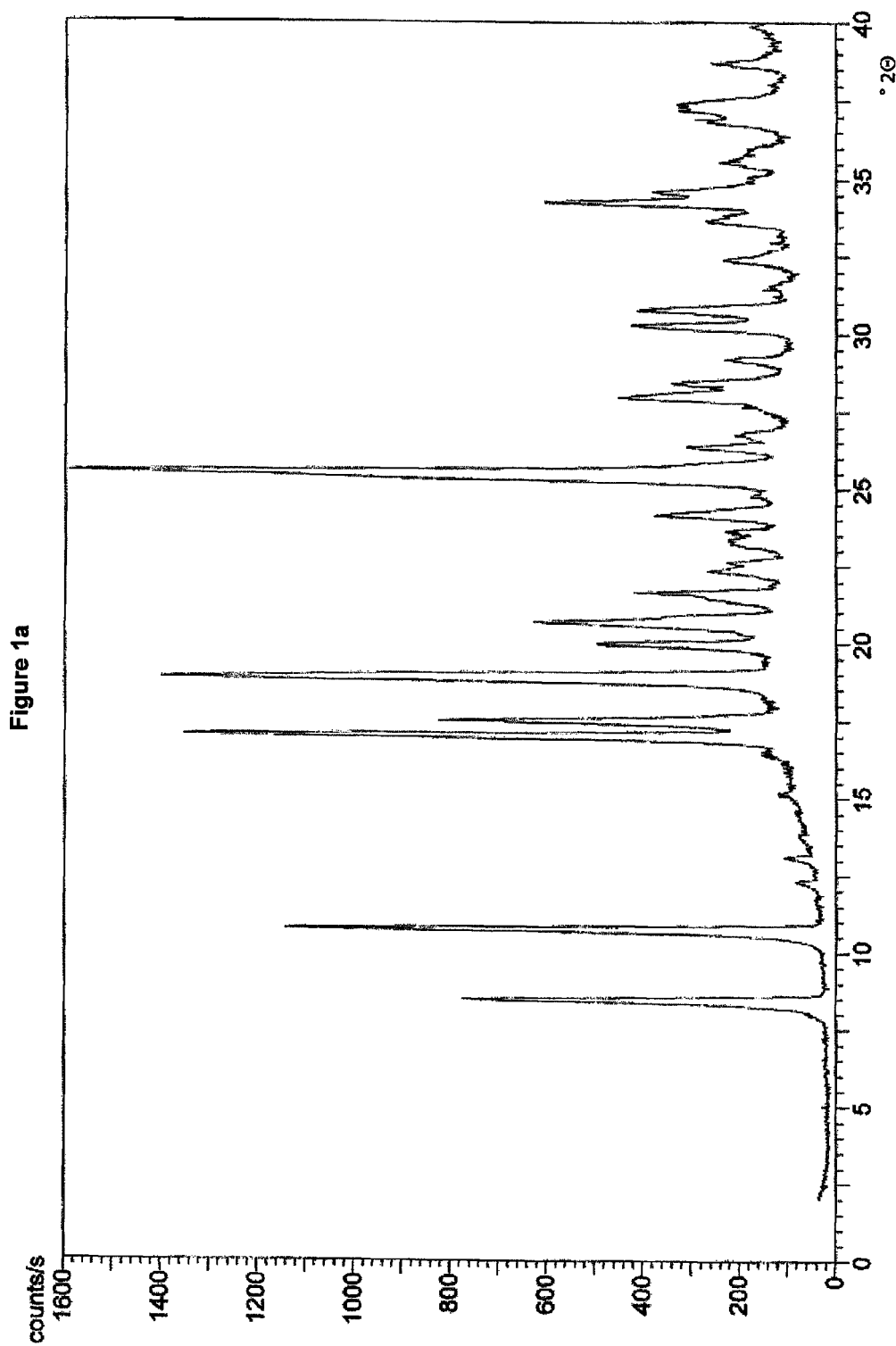

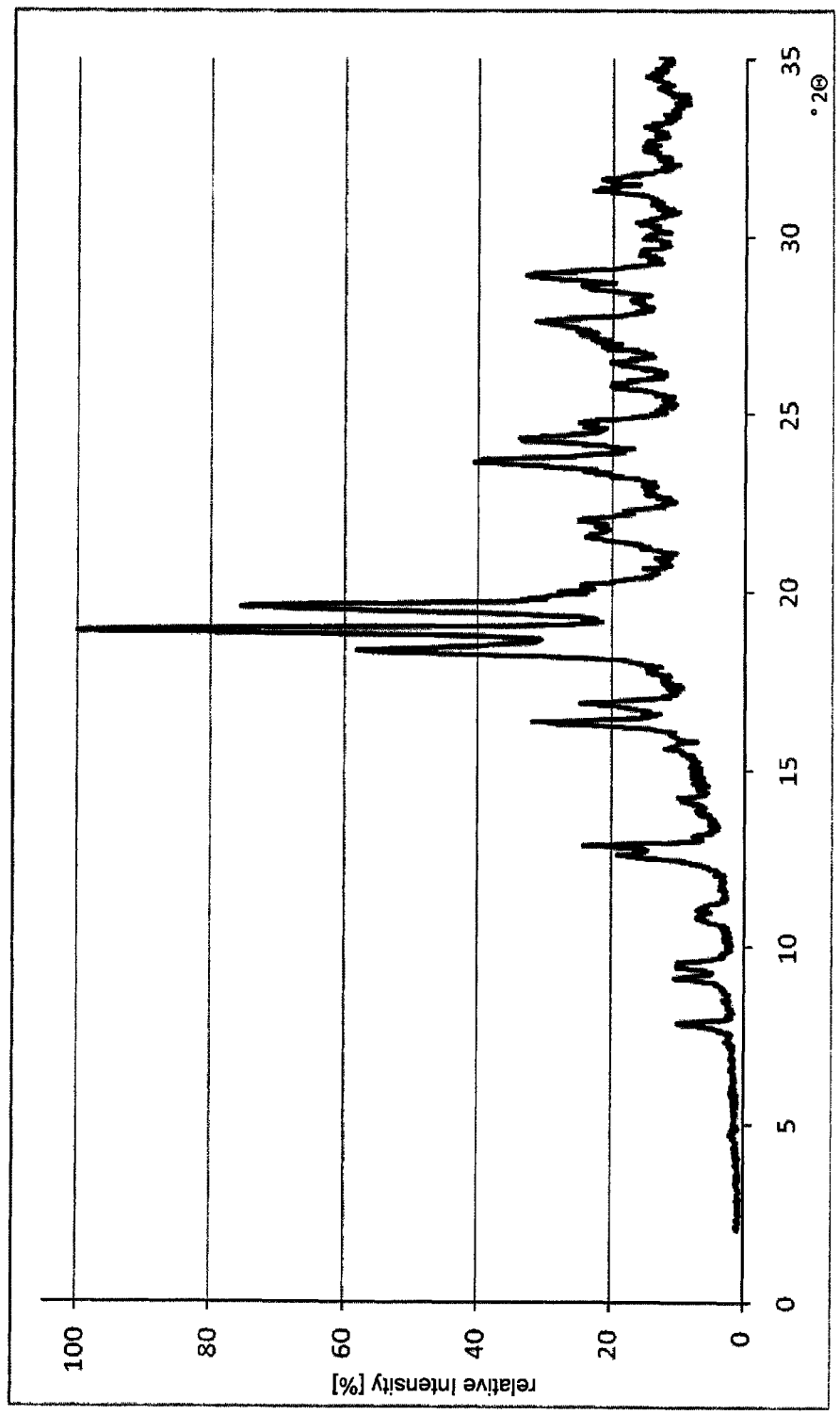

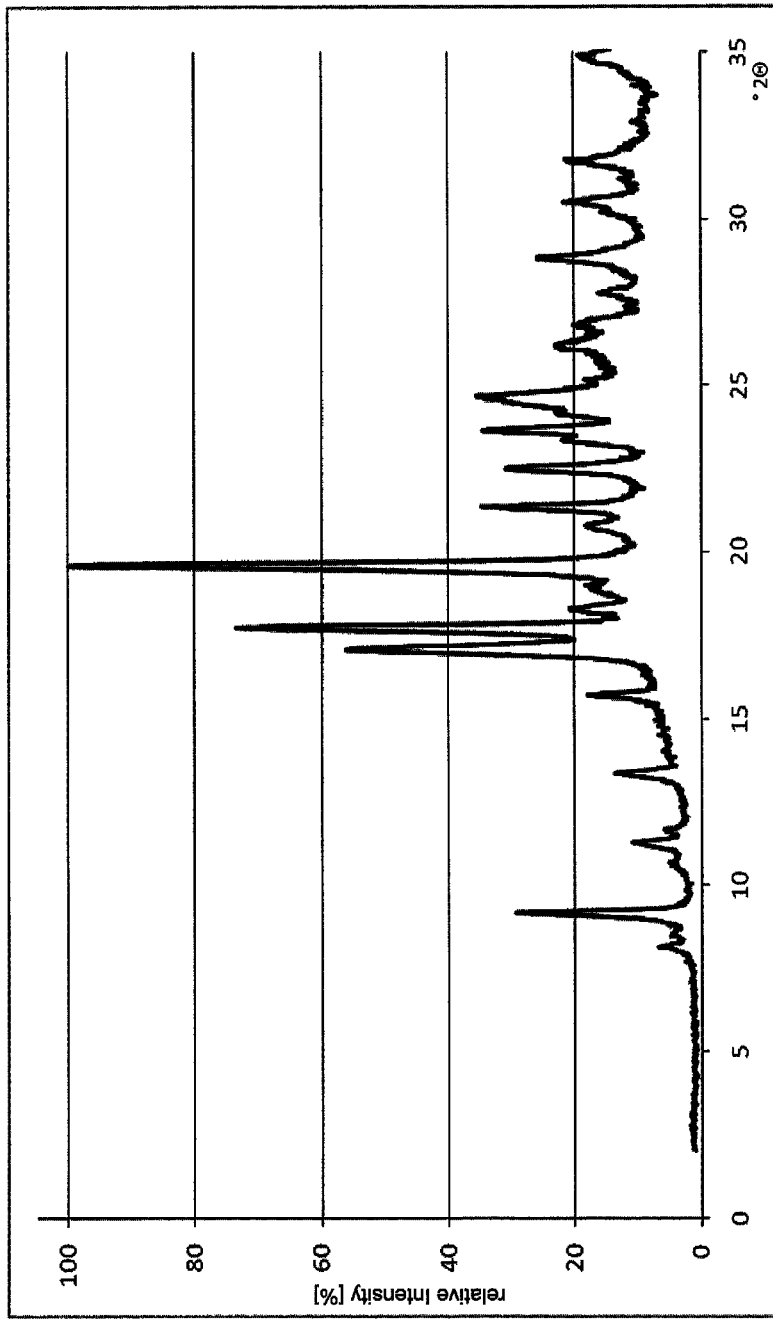

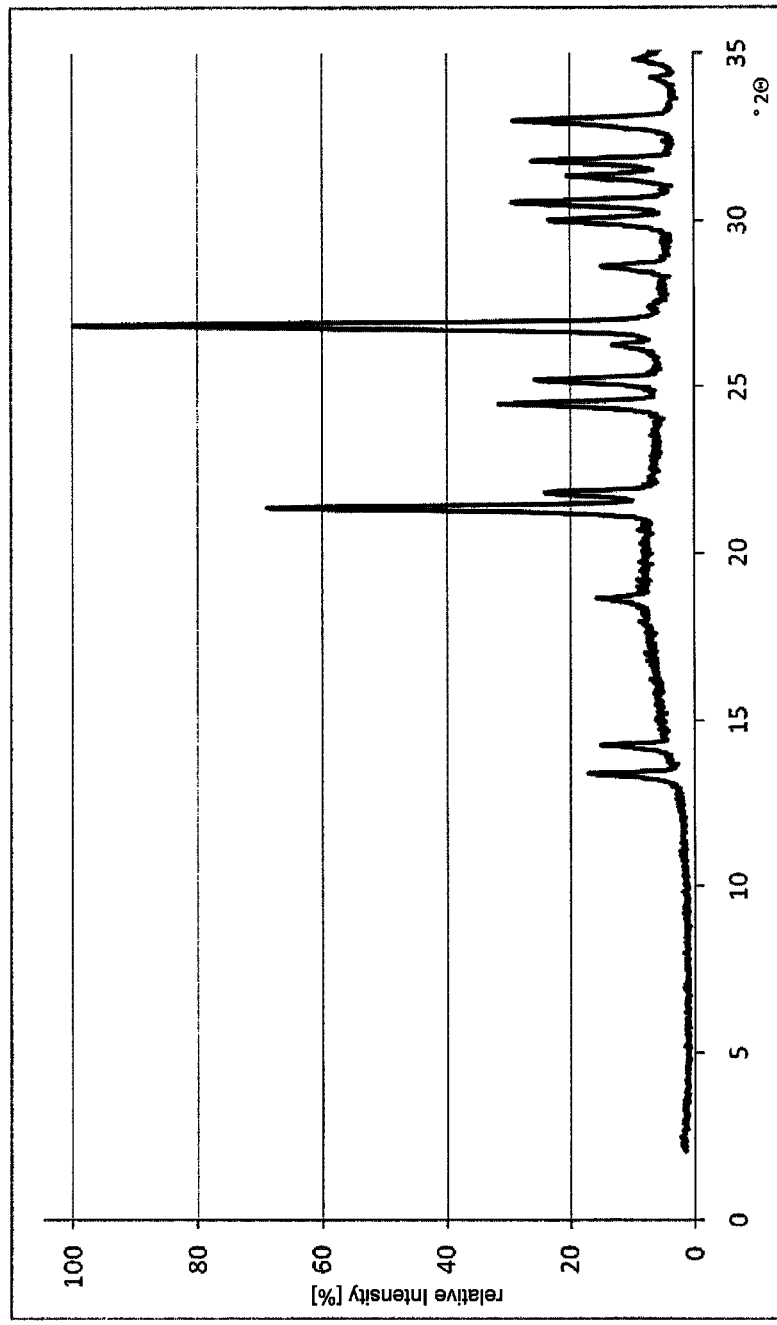

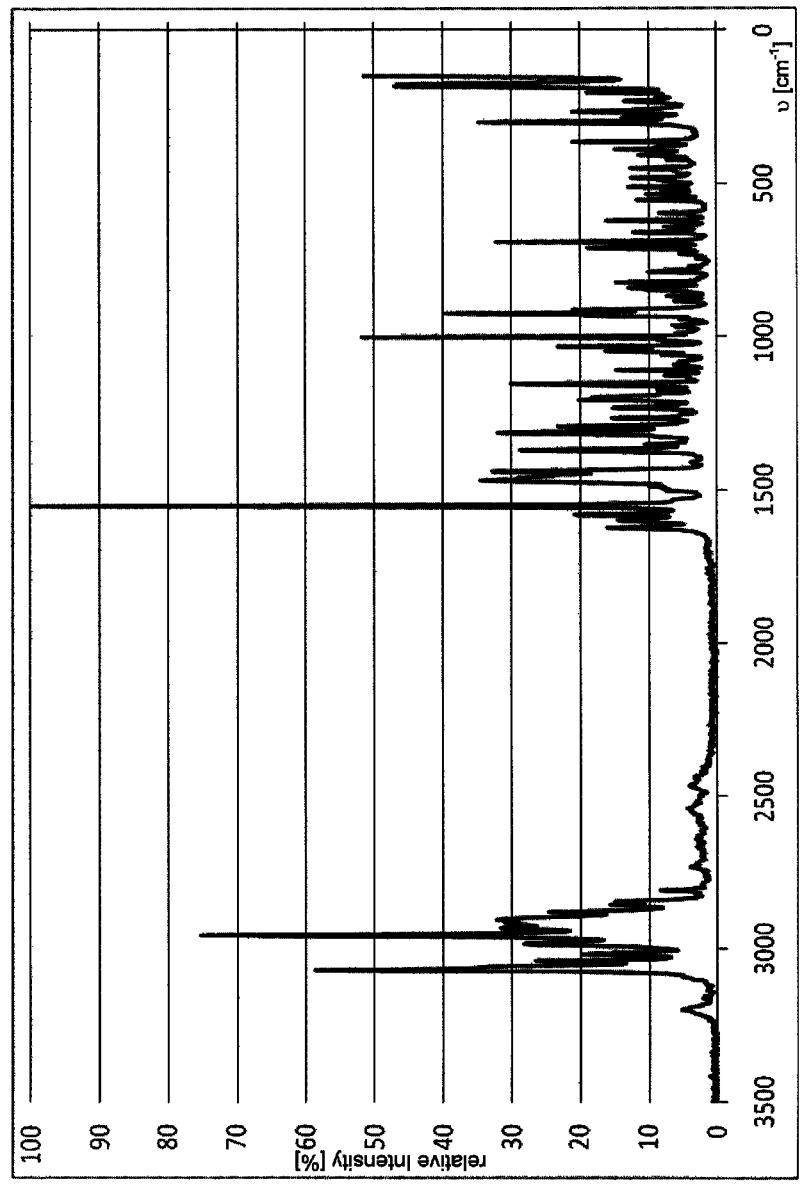

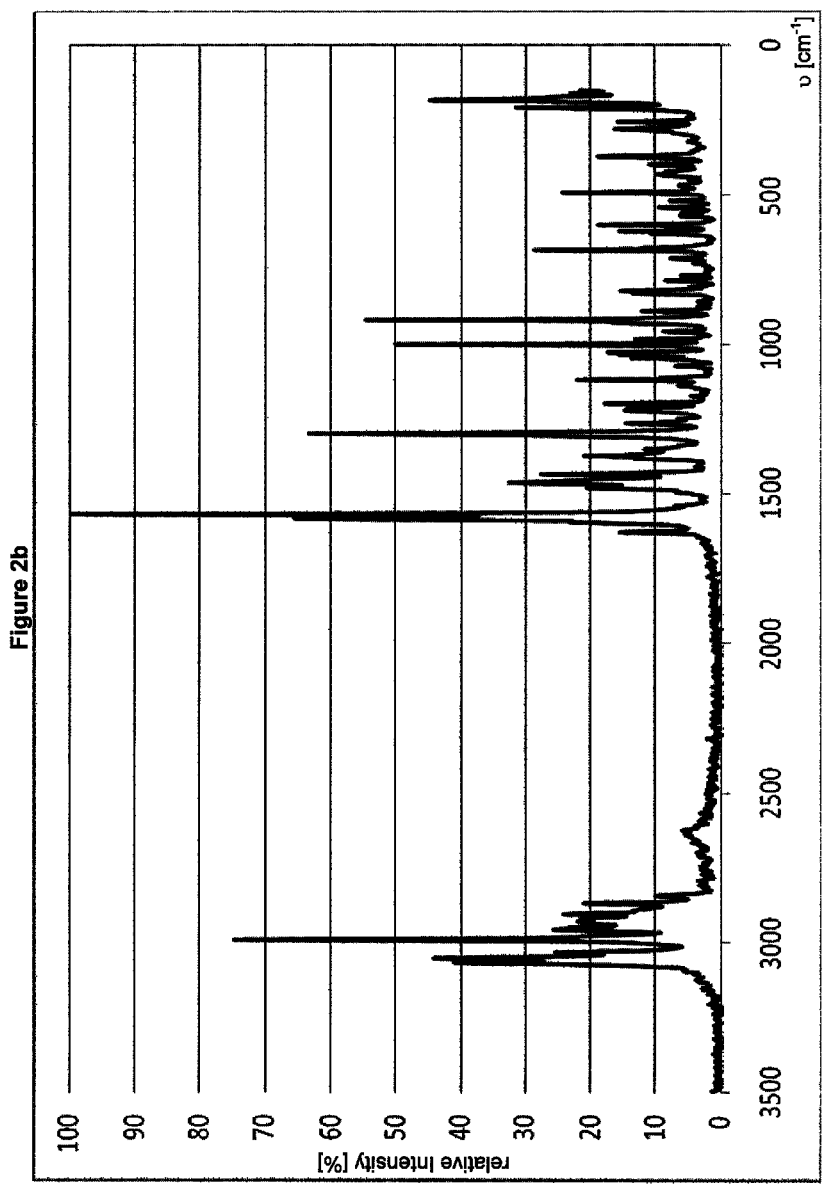

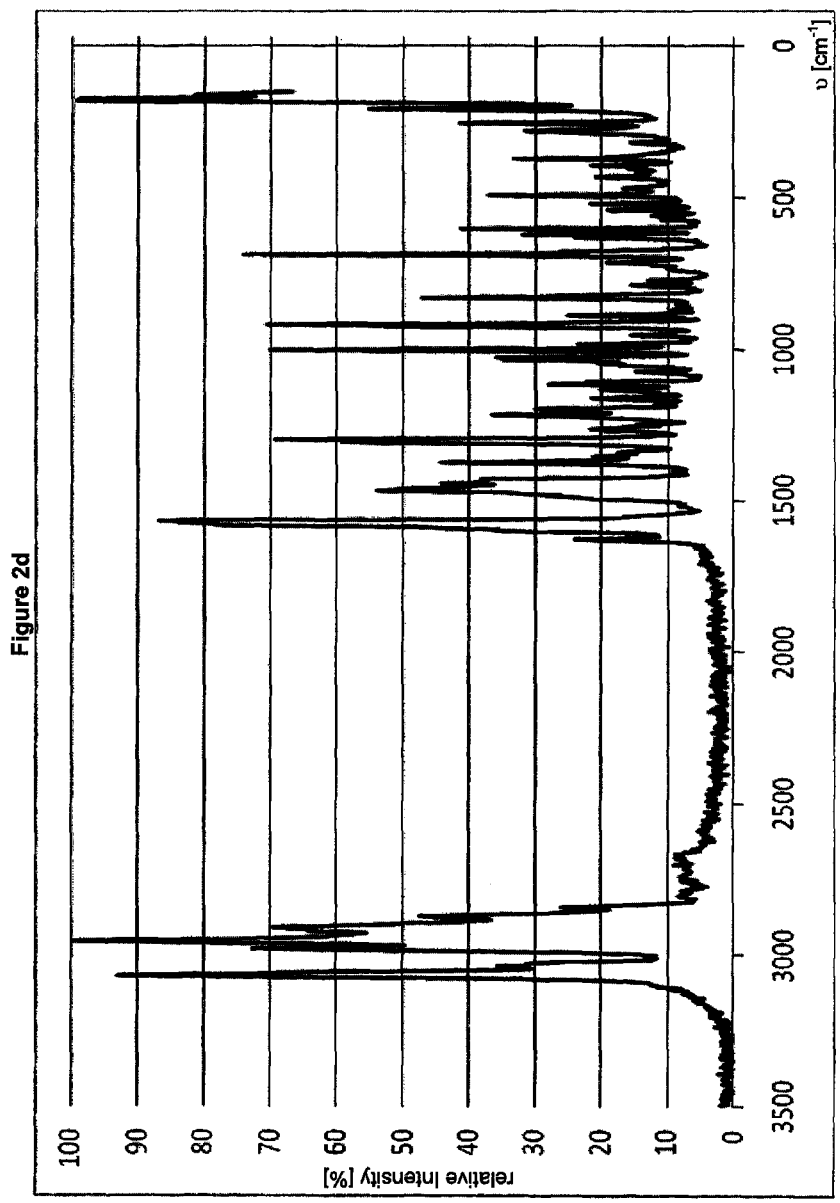

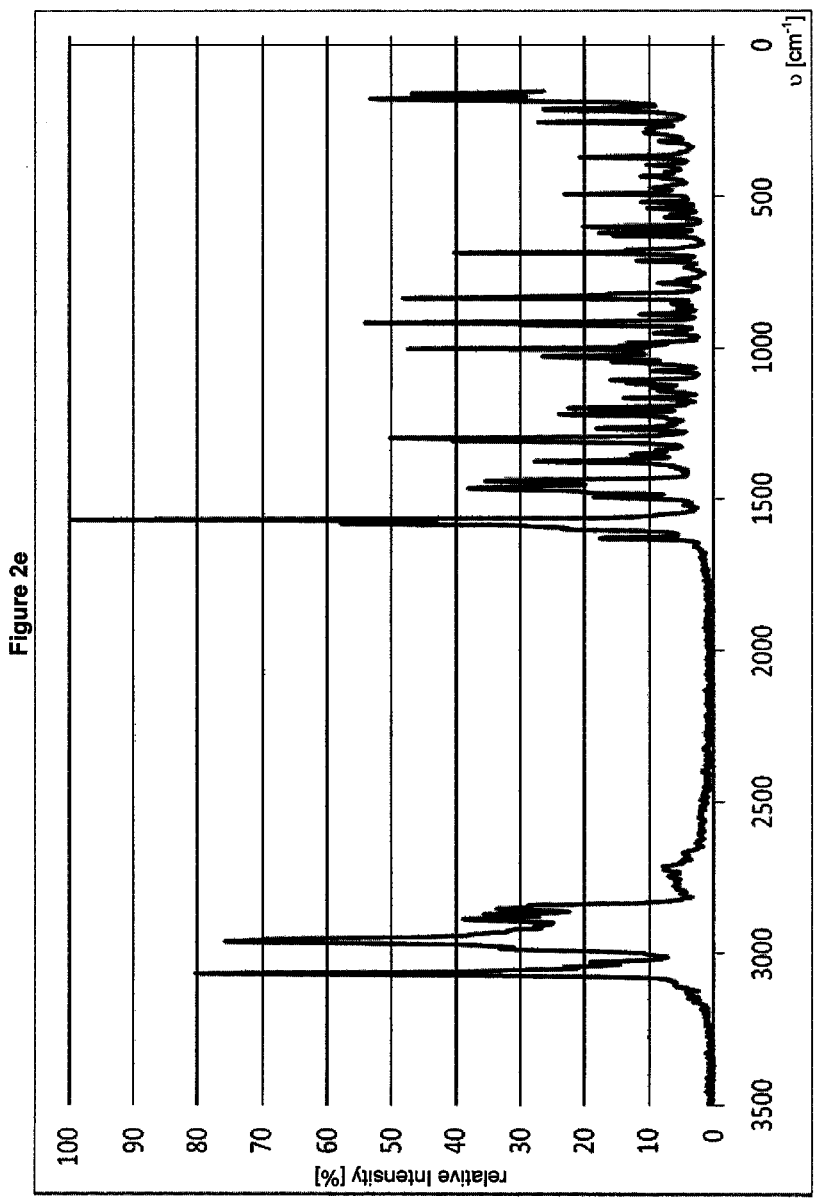

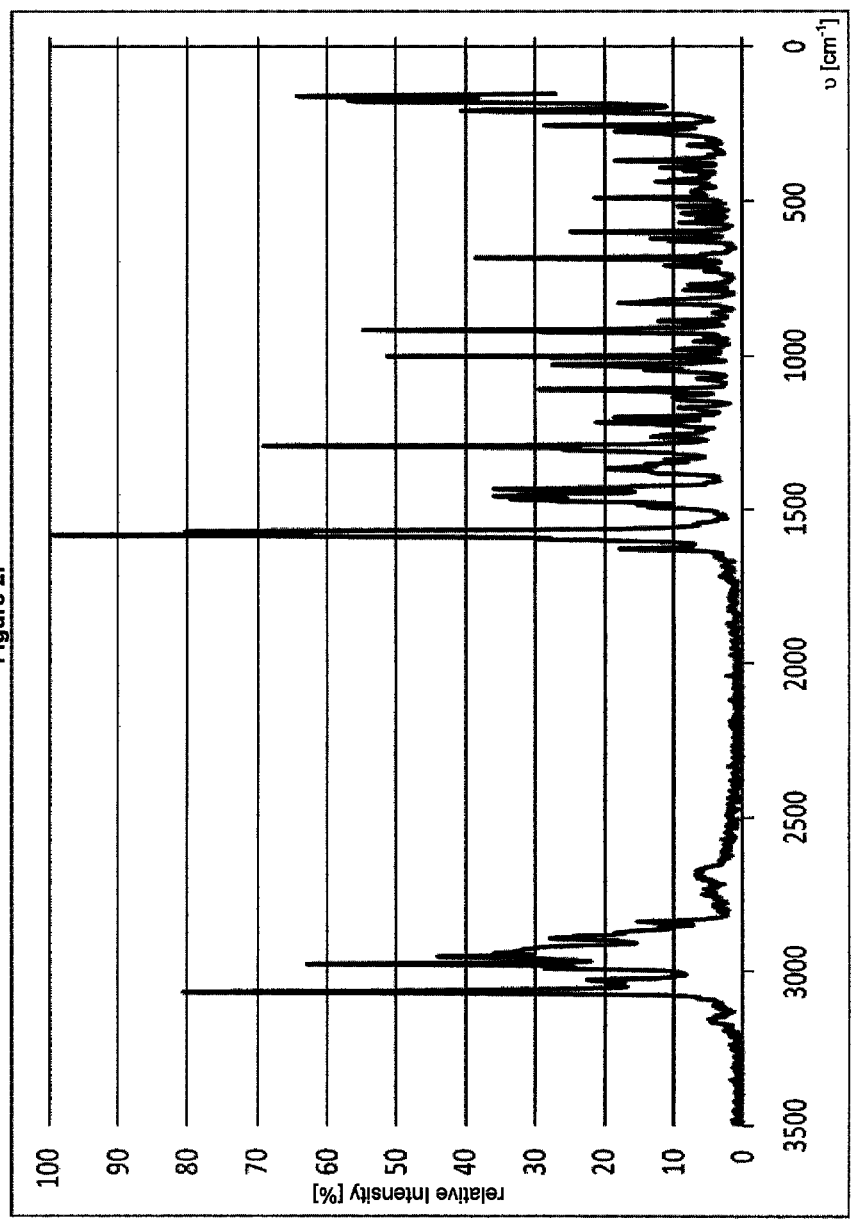

SOLID FORMS OF (1R,4R)-6'-FLUORO-N,N-DIMETHY1-4-PHENYL-4',9'-DIHYDRO-3'H-SPIRO-[CYCLOHEXANE-1,1'-PYRANO-[3,4,B]INDOL]-4-AMINE HYDROCHLORIDE

CROSS REFERENCE TO RELATED APPLICATIONS

This application claims priority based on U.S. provisional patent application No. 61/569,512, filed Dec. 12, 2011, the entire disclosure of which is incorporated herein by reference. Priority is also claimed based on Europaen patent application no. 11 009 773.0, filed Dec. 12, 2011, the entire disclosure of which is likewise incorporated herein by reference.

FIELD OF THE INVENTION

The invention relates to solid forms of (1r,4r)-6'-fluoro-N,N-dimethyl-4-phenyl-4',9'-dihydro-3'H-spiro[cyclohexane-1,1'-pyrano[3,4,b]indol]-4-amine hydrochloride, in particular crystalline forms and/or amorphous forms thereof, pharmaceutical compositions and medicaments comprising these solid forms, the use of these solid forms as well as to a process for obtaining them.

BACKGROUND OF THE INVENTION

Pharmaceutically active drugs can exist in different solid forms. For example, a drug may exist in different crystalline forms which have different physical and chemical properties.

Different physical properties can cause different crystalline forms of the same drug to have largely different processing and storage performance. Such physical properties include, for example, thermodynamic stability, crystal morphology [form, shape, structure, particle size, particle size distribution, degree of crystallinity, color], ripple behavior, flowability, density, bulk density, powder density, apparent density, vibrated density, depletability, emptyability, hardness, deformability, grindability, compressability, compactability, brittleness, elasticity, caloric properties [particularly melting point], solubility [particularly equilibrium solubility, pH dependence of solubility], dissolution [particularly dissolution rate, intrinsic dissolution rate], reconstitutability, hygroscopicity, tackiness, adhesiveness, tendency to electrostatic charging, and the like.

In addition, different chemical properties can cause different crystalline forms of the same drug to have largely different performance properties. For example, a crystalline form having a low hygroscopicity (relative to other crystalline forms) can have superior chemical stability and longer shelf-life stability (cf. R. Hilfiker, Polymorphism, 2006 Wiley VCH, pp 235-242).

Further, different stereoisomers of one compound can form different crystalline forms. In some cases this difference can be exploited to allow separation of the stereoisomers from one another.

One particular drug that is of great interest for use in treating cancer pain (and other acute, visceral, neuropathic and chronic pain disorders) is (1r,4r)-6'-fluoro-N,N-dimethyl-4-phenyl-4',9'-dihydro-3'H-spiro[cyclohexane-1,1'-pyrano[3,4b]indol]-4-amine. This drug is depicted below as the compound of formula (I).

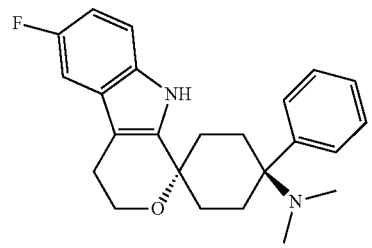

(1r,4r)-6'-fluoro-N,N-dimethyl-4-phenyl-4',9'-dihydro-3'H-spiro[cyclohexane-1,1'-pyrano[3,4-b]indol]-4-amine The solid forms of (1r,4r)-6'-fluoro-N,N-dimethyl-4-phenyl-4',9'-dihydro-3'H-spiro[cyclo-hexane-1,1'-pyrano[3,4b]indol]-4-amine that are known so far are not satisfactory in every respect and there is a demand for advantageous solid forms.

SUMMARY OF THE INVENTION

It is an object of the invention to provide forms or modifications of (1r,4r)-6'-fluoro-N,N-dimethyl-4-phenyl-4',9'-dihydro-3'H-spiro[cyclohexane-1,1'-pyrano[3,4,b]indol]-4-amine that have advantages compared to the forms or modifications of the prior art.

This object has been achieved by the present invention.

It has been found that by converting (1r,4r)-6'-fluoro-N,N-dimethyl-4-phenyl-4',9'-dihydro-3'H-spiro[cyclohexane-1,1'-pyrano[3,4b]indol]-4-amine into the hydrochloride salt, optionally in the form of a solvate thereof, the aqueous solubility of the compound may be improved.

It has surprisingly been found that converting (1r,4r)-6'-fluoro-N,N-dimethyl-4-phenyl-4',9'-dihydro-3'H-spiro[cyclohexane-1,1'-pyrano[3,4b]indol]-4-amine into the hydrochloride salt, optionally in the form of a solvate thereof, and subsequent crystallization purifies the compound.

Moreover, it has surprisingly been found that different crystalline forms of (1r,4r)-6'-fluoro-N,N-dimethyl-4-phenyl-4',9'-dihydro-3'H-spiro[cyclohexane-1,1'-pyrano[3,4b]indol]-4-amine hydrochloride, optionally in the form of solvates thereof, can be prepared which have fundamentally different properties. These inventive crystalline forms are described herein.

BRIEF DESCRIPTION OF THE DRAWINGS

FIGS. 1a-g show the PXRD patterns of crystalline forms A, B, C, D, E, F and G.
FIGS. 2a-g show the Raman spectra of crystalline forms A, B, C, D, E, F and G.

DETAILED DESCRIPTION

Figure 1B:
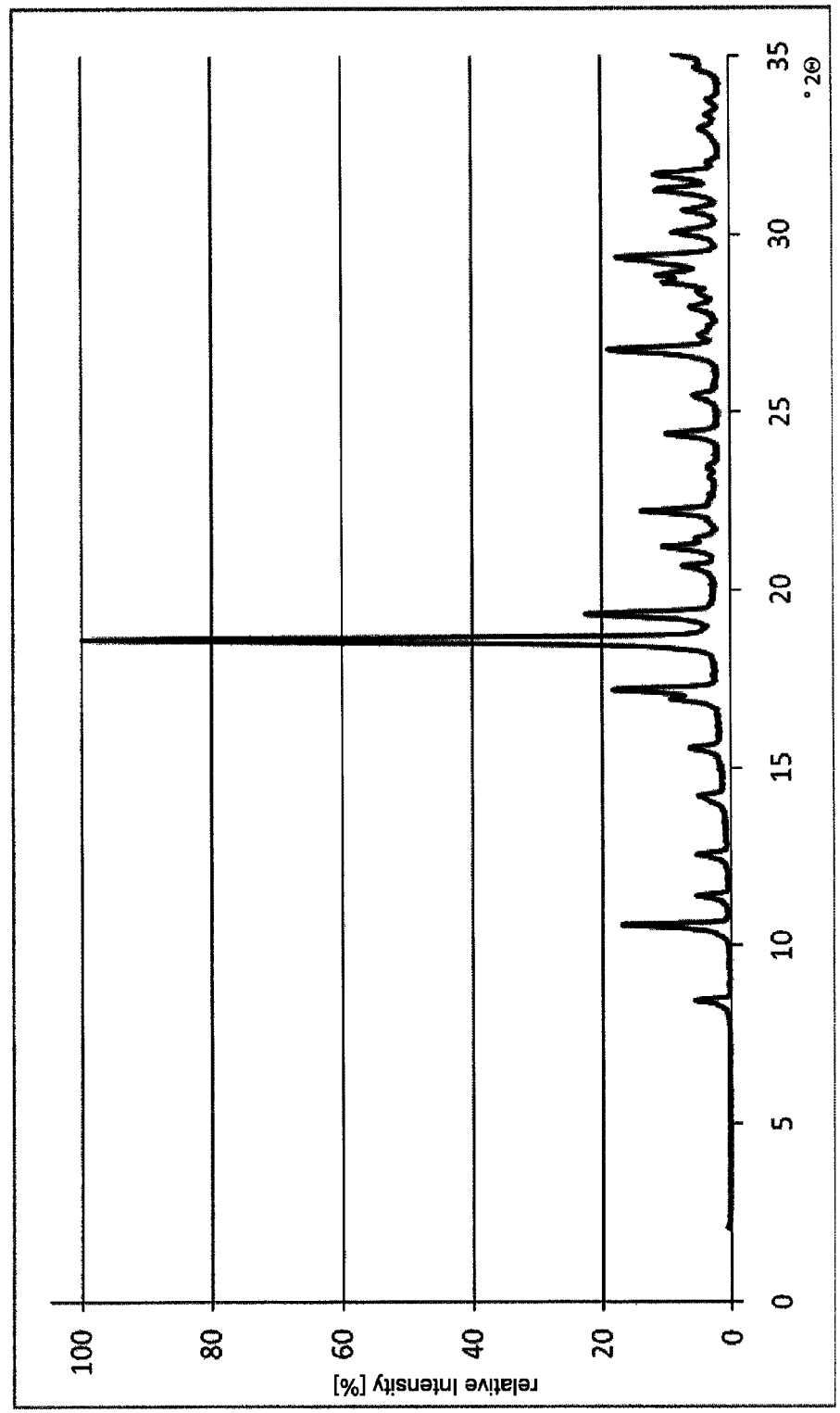

The compound according to general formula (I) can systematically be referred to as "1,1-(3-dimethylamino-3-phenylpentamethylene)-6-fluoro-1,3,4,9-tetrahydropyrano[3,4-b]indole (trans)" or as "(1r,4r)-6'-fluoro-N,N-dimethyl-4-phenyl-4',9'-dihydro-3'H-spiro[cyclohexane-1,1'-pyrano[3,4,b]indol]-4-amine", respectively.

In the solid form according to the invention the compound according to general formula (I) is present in form of the hydrochloride. The definition of the hydrochloride of the compound according to general formula (I) as used herein includes salts, solvates, co-crystals, polymorphs, amorphous forms and multi-component complex forms. For the purpose of the specification, "hydrochloride" preferably means that the compound according to general formula (I) is present in form of the hydrochloric acid-addition salt. The most basic functional group of the compound according to general formula (I) is its N,N-dimethylamino moiety, which thus according to the invention is preferably protonated. Methods to determine whether a chemical substance is present as a salt, co-crystalline form, crystalline form or as the free base, optionally in each case in a solvated from thereof, are known to the skilled artisan such as $^{14}N$ or $^{15}N$ solid state NMR, X-ray diffraction, IR, DSC, TGA, Raman and XPS. $^{1}H$-NMR recorded in solution may also be used to consider the presence of protonation.

Unless explicitly stated otherwise, all 2Θ values refer to a X-ray diffractogram measured using CuKα radiation having a wavelength of 1.54060 Å determined at 23+/−3° C.

One aspect of the present invention relates to a solid form of (1r,4r)-6'-fluoro-N,N-dimethyl-4-phenyl-4',9'-dihydro-3'H-spiro[cyclohexane-1,1'-pyrano[3,4b]indol]-4-amine hydrochloride.

The solid form according to the invention may be a crystalline form or an amorphous form, which may be in the form of an ansolvate or in the form of a solvate.

Mixtures of crystalline forms and/or amorphous forms are also included within the scope of the present invention.

In a preferred embodiment, the solid form according to the invention is an amorphous form.

Suitable methods for the preparation of amorphous forms are known to a person skilled in the art. For example, amorphous forms of or amorphous mixtures may be obtained by means of the following methods:
i) precipitation from solution,
ii) lyophilization,
iii) spray drying,
iv) melts extrusion,
v) flash evaporation,
vi) quench cooling of the melt,
vii) grinding at ambient or liquid nitrogen temperatures, and/or
viii) using capillary crystallization technology.

In a preferred embodiment, the solid form according to the invention is a crystalline form of (1r,4r)-6'-fluoro-N,N-dimethyl-4-phenyl-4',9'-dihydro-3' H-spiro[cyclohexane-1,1'-pyrano-[3,4b]indol]-4-amine hydrochloride.

In some preferred embodiments, the crystalline form according to the invention has an X-ray diffraction peak at 14.3±0.5 (2Θ) and/or an X-ray diffraction peak at 17.1±0.5 (2Θ) and/or an X-ray diffraction peak at 18.9±0.5 (2Θ) and/or an X-ray diffraction peak at 19.6±0.5 (2Θ). All values refer to a X-ray diffractogram measured using CuKα radiation having a wavelength of 1.54060 Å.

Preferably, said X-ray diffraction peak(s) exhibit(s) a relative intensity of at least 20%, more preferably of at least 25%, still more preferably of at least 30%, yet more preferably of at least 40%, most preferably of at least 45% and in particular, of at least 50%.

Preferably, the crystalline form according to the invention has at least two Raman peaks selected from the group consisting of 918±5 cm$^{-1}$, 1299±5 cm$^{-1}$, 1569±5 cm$^{-1}$ and at 1583±5 cm$^{-1}$.

In a preferred embodiment, the crystalline form according to the invention has at least three Raman peaks selected from the group consisting of 918±5 cm$^{-1}$, 1299±5 cm$^{-1}$, 1569±5 cm$^{-1}$ and at 1583±5 cm$^{-1}$. In an especially preferred embodiment, the crystalline form according to the invention has all four peaks.

The solid form according to the invention may be an ansolvate or a solvate. Therefore, the crystalline form according to the invention may be an ansolvate or a solvate.

In a preferred embodiment, the crystalline form is an ansolvate.

In a preferred embodiment, the ansolvate form does not contain any solvent.

In another preferred embodiment, the ansolvate form may contain up to 1.5 wt.-% of water.

In another preferred embodiment, the ansolvate form does not contain any impurities.

Impurities in the sense of the present invention may be preferably understood as reagents or decomposition products thereof, which have been employed in the synthesis of the compound according to formula (I) and/or the synthesis of the inventive solid form thereof, or as decomposition or reaction products of (1r,4r)-6'-fluoro-N,N-dimethyl-4-phenyl-4',9'-dihydro-3'H-spiro[cyclohexane-1,1'-pyrano[3,4b]indol]-4-amine or hydrochloric acid or agent employed for the in-situ generation of hydrochloric acid.

In another preferred embodiment, the crystalline form is a solvate. Preferably, the solvate is selected from hydrates, solvates of 1,4-dioxane and solvates of pyridine, or mixtures thereof.

In a preferred embodiment, the solvate form does not contain any impurities.

Another aspect of the present invention relates to a process for the production of the solid form, in particular the crystalline form according to the invention.

In a preferred embodiment, the process comprises the step of
(a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

For the purpose of the specification, "free base" preferably means that the compound according to general formula (I) is not present in form of a salt, particularly not in form of an acid-addition salt.

Conventional solvents known to persons skilled in the art may be used as solvents in a solution or suspension of this type, such as water or organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

In a preferred embodiment, the solution is a solution of hydrogen chloride in an aqueous solvent, hydrochloric acid is particularly preferred.

In another preferred embodiment, the solution is a solution of hydrogen chloride in an organic solvent, especially preferred are alcohols such as ethanol, isopropanol and n-butanol, and ethers such as diethylether, di-isopropylether, tetrahydrofurane, methyl-tetrahydrofurane 1,4-dioxane.

Preferably, the hydrogen-chloride containing solution and the solution of the free base contain the same solvent.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air, nitrogen flow or argon flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine hydrochloride in a solvent.

Conventional solvents known to persons skilled in the art may be used as solvents in a suspension of this type, in particular organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and also N-methyl-2-pyrrolidone, dimethyl formamide and dimethyl sulfoxide; and mixtures thereof. Saturated hydrocarbons, such as n-pentane, n-hexane and n-heptane, and water are less suitable, the compound (1r,4r)-6'-fluoro-N,N-dimethyl-4-phenyl-4',9'-dihydro-3'H-spiro[cyclohexane-1,1'-pyrano[3,4,b]indol]-4-amine hydrochloride being only poorly soluble in these substances.

Preferably, the solvent is selected from the group consisting of dichloromethane, N-methyl-2-pyrrolidone, methanol, dimethyl formamide, and mixtures thereof.

In an especially preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent or solvent mixture, more preferably at a temperature not higher than 80° C., more preferably not higher than 60° C., even more preferably not higher than 40° C., and in particular in a temperature range of 20-40° C.

In a preferred embodiment, the process according to the invention further comprises the step (b-2) evaporating the solvent of the solution obtained in step (a-2).

Suitable methods for evaporating the solvent are known to a person skilled in the art. Preferably, in the process according to the invention, the solvent is evoporated in air, air flow, or inert gas flow, in particular argon or nitrogen flow. However, evaporating the solvent under vacuum, for example by means of a rotary evaporator, is also possible.

Preferably, in the process according to the invention, the solvent is evoporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-aminehydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water.

The amount of the media in which (1r,4r)-6'-fluoro-N,N-dimethyl-4-phenyl-4',9'-dihydro-3'H-spiro[cyclohexane-1, 1'-pyrano[3,4,b]indol]-4-amine hydrochloride is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Furthermore, the amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride, is only poorly soluble, the precipitant or anti-solvent, is preferably selected in such a manner that the dissolved component is completely precipitated or at least up to 90% of the initial amount is precipitated within a time period of at most 90 minutes, more preferably at most 80 minutes, still more preferably at most 70 minutes, and most preferably at most 60 minutes after the anti-solvent has been completely added.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble, i.e. by a vapor diffusion crystallization technique.

In this embodiment, dichloromethane is preferably selected as solvent in step (a-2) and the solution obtained in step (a-2) is preferably exposed to an atmosphere containing hexane.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow. However, depending on the crystalline form to be obtained evaporating the solvent at an elevated temperature, e.g. within the range of from 20° C. to 60° C., is also possible.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride in a solvent.

Conventional solvents known to persons skilled in the art may be used as solvents in a suspension of this type, in particular water and organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

In a preferred embodiment, step (a-3) is carried out at a temperature below or at the boiling point of the respective solvent, preferably at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

A further aspect of the invention relates to a solid form, preferably a crystalline form of (1r,4r)-6'-fluoro-N,N-dimethyl-4-phenyl-4',9'-dihydro-3'H-spiro[cyclohexane-1,1'-pyrano-[3,4,b]indol]-4-amine hydrochloride that is obtainable by the process as described above.

In the following, any reference to a "crystalline form" refers to a crystalline form of (1r,4r)-6'-fluoro-N,N-dimethyl-4-phenyl-4',9'-dihydro-3'H-spiro[cyclohexane-1,1'-pyrano [3,4, b]indol]-4-amine hydrochloride.

A further aspect of the present invention relates to a crystalline form A.

Preferably, the crystalline form A according to the invention has one or more X-ray diffraction peaks selected from the group consisting of 10.8±0.2 (2Θ), 17.0±0.2 (2Θ), 17.5±0.2 (2Θ), 18.9±0.2 (2Θ) and 25.5±0.2 (2Θ). In some preferred embodiments, the crystalline form comprises X-ray diffraction peaks at 17.0±0.2 (2Θ), 18.9±0.2 (2Θ) and 25.5±0.2 (2Θ). In some preferred embodiments, the crystalline form comprises an X-ray diffraction peak at 25.5±0.2 (2Θ).

In some preferred embodiments, crystalline form A comprises X-ray diffraction peaks at 10.8±0.2 (2Θ), 17.0±0.2 (2Θ), 18.9±0.2 (2Θ), 25.5±0.2 (2Θ) and optionally 17.5±0.2 (2Θ).

The crystalline form A according to the invention may additionally have at least one X-ray diffraction peak selected from the group consisting of 8.4±0.2 (2Θ), 20.0±0.2 (2Θ), 20.7±0.2 (2Θ), 24.1±0.2 (2Θ), 27.9±0.2 (2Θ), 30.2±0.2 (2Θ), 30.8±0.2 (2Θ) and 34.3±0.2 (2Θ).

Further, the crystalline form A according to the invention may be characterised in that as well as one or more X-ray diffraction peaks selected from the group consisting of 10.8±0.2 (2Θ), 17.0±0.2 (2Θ), 17.5±0.2 (2Θ), 18.9±0.2 (2Θ) and 25.5±0.2 (2Θ), and optionally one or more X-ray diffraction peaks selected from the group consisting of 8.4±0.2 (2Θ), 20.0±0.2 (2Θ), 20.7±0.2 (2Θ), 24.1±0.2 (2Θ), 27.9±0.2 (2Θ), 30.2±0.2 (2Θ), 30.8±0.2 (2Θ) and 34.3±0.2 (2Θ), it additionally has at least one X-ray diffraction peak selected from the group consisting of 21.6±0.2 (2Θ), 22.3±0.2 (2Θ), 23.6±0.2 (2Θ), 26.3±0.2 (2Θ), 28.4±0.2 (2Θ), 33.7±0.2 (2Θ), and 34.6±0.2 (2Θ).

The crystalline form A according to the invention may further be characterised in that as well as one or more X-ray diffraction peaks selected from the group consisting of 10.8±0.2 (2Θ), 17.0±0.2 (2Θ), 17.5±0.2 (2Θ), 18.9±0.2 (2Θ) and 25.5±0.2 (2Θ), and optionally one or more X-ray diffraction peaks selected from the group consisting of 8.4±0.2 (2Θ), 20.0±0.2 (2Θ), 20.7±0.2 (2Θ), 24.1±0.2 (2Θ), 27.9±0.2 (2Θ), 30.2±0.2 (2Θ), 30.8±0.2 (2Θ) and 34.3±0.2 (2Θ), and optionally one or more X-ray diffraction peaks selected from the group consisting of 21.6±0.2 (2Θ), 22.3±0.2 (2Θ), 23.6±0.2 (2Θ), 26.3±0.2 (2Θ), 28.4±0.2 (2Θ), 33.7±0.2 (2Θ), and 34.6±0.2 (2Θ), it additionally has at least one X-ray diffraction peak selected from the group consisting of 12.3±0.2 (2Θ), 13.1±0.2 (2Θ), 22.6±0.2 (2Θ), 23.3±0.2 (2Θ), 26.8±0.2 (2Θ), 29.2±0.2 (2Θ), 31.5±0.2 (2Θ) and 32.4±0.2 (2Θ).

All 2Θ values refer to an X-ray diffractogram measured using CuKα radiation having a wavelength of 1.54060 Å.

In DSC analyses, the crystalline form A according to the present invention preferably exhibits an endothermal event with a peak temperature at 258-268° C., more preferably at 259-267° C., still more preferably at 260-266° C., yet more preferably at 261-265° C. and in particular at 262-265° C.

Preferably, the crystalline form A according to the present invention further exhibits a further endothermal event, preferably within a temperature range of 210-275° C.

The crystalline form A according to the present invention may further be characterized in that it has one or more Raman bands selected from the group consisting of 1003±2 cm$^{-1}$, 1554±2 cm$^{-1}$, 2958±2 cm$^{-1}$ and 3071±2 cm$^{-1}$.

The crystalline form A according to the present invention may further be characterized in that it has one or more Raman bands selected from the group consisting of 1003±2 cm$^{-1}$, 1554±2 cm$^{-1}$, 2958±2 cm$^{-1}$ and 3071±2 cm$^{-1}$; and/or one or more Raman bands selected from the group consisting of 691±2 cm$^{-1}$, 914±2 cm$^{-1}$, 926±2 cm$^{-1}$, 1034±2 cm$^{-1}$, 1156±2 cm$^{-1}$, 1295±2 cm$^{-1}$, 1316±2 cm$^{-1}$, 1372±2 cm$^{-1}$, 1441±2 cm$^{-1}$, 1470±2 cm$^{-1}$, 1582±2 cm$^{-1}$, 2882±2 cm$^{-1}$, 2907±2 cm$^{-1}$, 2935±2 cm$^{-1}$, 2986±2 cm$^{-1}$, 3020±2 cm$^{-1}$ and 3041±2 cm$^{-1}$.

The crystalline form A according to the present invention may further be characterized in that it has one or more Raman bands selected from the group consisting of 408±2 cm$^{-1}$, 451±2 cm$^{-1}$, 483±2 cm$^{-1}$, 512±2 cm$^{-1}$, 524±2 cm$^{-1}$, 536±2 cm$^{-1}$, 554±2 cm$^{-1}$, 597±2 cm$^{-1}$, 621±2 cm$^{-1}$, 642±2 cm$^{-1}$, 660±2 cm$^{-1}$, 712±2 cm$^{-1}$, 789±2 cm$^{-1}$, 824±2 cm$^{-1}$, 842±2 cm$^{-1}$, 869±2 cm$^{-1}$, 885±2 cm$^{-1}$, 965±2 cm$^{-1}$, 1049±2 cm$^{-1}$, 1061±2 cm$^{-1}$, 1095±2 cm$^{-1}$, 1112±2 cm$^{-1}$, 1128±2 cm$^{-1}$, 1175±2 cm$^{-1}$, 1201±2 cm$^{-1}$, 1208±2 cm$^{-1}$, 1234±2 cm$^{-1}$, 1268±2 cm$^{-1}$, 1353±2 cm$^{-1}$, 1600±2 cm$^{-1}$, 1625±2 cm$^{-1}$, 2542±2 cm$^{-1}$, 2811±2 cm$^{-1}$, 2847±2 cm$^{-1}$, 2858±2 cm$^{-1}$ and 3201±2 cm$^{-1}$.

Another aspect of the present invention relates to a process for the production of the crystalline form A described above.

In a preferred embodiment, the process comprises the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension of this type, in particular water and organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

Preferably, the solvent is selected from the group consisting of alcohols such as methanol, ethanol, n-propanol, iso-propanol and n-butanol; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; chlorinated hydrocarbons such as dichloromethane and chloroform; and mixtures thereof.

Especially preferred are solvents selected from the group consisting of tetrahydrofuran, 1,4-dioxane, acetone, dichloromethane, methanol, ethanol, isopropanol, water, and mixtures thereof, in particular THF/water and acetone/water mixtures.

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

In a preferred embodiment, the solution is a solution of hydrogen chloride in an aqueous solvent, hydrochloric acid is particularly preferred.

In another preferred embodiment, the solution is a solution of hydrogen chloride in an organic solvent, especially preferred are alcohols such as ethanol, isopropanol and n-butanol, and ethers such as diethylether, di-isopropylether, tetrahydrofurane, methyl-tetrahydrofurane 1,4-dioxane.

Preferably, the hydrogen-chloride containing solution and the solution of the free base contain the same solvent.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In a preferred embodiment, the suspension obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

In another preferred embodiment, the suspension obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of
(a-2) dissolving (1r,4r)-6'-fluoro-N,N-dimethyl-4-phenyl-4', 9'-dihydro-3'H-spiro[cyclohexane-1,1'-pyrano[3,4,b]indol]-4-amine hydrochloride in a solvent.

Conventional solvents known to persons skilled in the art may be used as solvents in a suspension of this type, in particular organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and also N-methyl-2-pyrrolidone, dimethyl formamide and dimethyl sulfoxide; and mixtures thereof. Saturated hydrocarbons, such as n-pentane, n-hexane and n-heptane, and water are less suitable, the compound (1r,4r)-6'-fluoro-N,N-dimethyl-4-phenyl-4',9'-dihydro-3'H-spiro[cyclohexane-1,1'-pyrano[3,4,b]indol]-4-amine hydrochloride being only poorly soluble in these substances.

Preferably, the solvent is selected from the group consisting of dichloromethane, N-methyl-2-pyrrolidone, methanol, dimethyl formamide, and mixtures thereof.

In an especially preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step (b-2) evaporating the solvent of the solution obtained in step (a-2).

Suitable methods for evaporating the solvent are known to a person skilled in the art.

Preferably, in the process according to the invention, the solvent is evoporated in air, air flow, or inert gas flow, in particular argon or nitrogen flow. However, evaporating the solvent under vacuum, for example by means of a rotary evaporator, is also possible.

Preferably, in the process according to the invention, the solvent is evoporated at room temperature.

In another preferred embodiment, the process further comprises the step of
(b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; ethers such as tert-butyl methyl ether, diethyl ether and diisopropyl ether; ketones such as acetone, 2-butanone, pentan-2-one, pentan- 3-one, hexan-2-one and hexan-3-one; nitriles such as acetonitril; pyridine, acetic acid and water. Especially preferred are ethyl acetate, acetonitril, acetone and diethyl ether.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes.

Step (b-2') may also be carried out by exposing the solution obtained in step (a-2) to an atmosphere containing a solvent, in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow.

In still another preferred embodiment, the process comprises the step of
(a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride in a solvent.

Conventional solvents known to persons skilled in the art may be used as solvents in a suspension of this type, in particular water and organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

Preferably, the solvent is water.

Preferably, in the process according to the invention, step (a-3) is carried out at a temperature below or at the boiling point of the respective solvent, preferably at a temperature not higher than 80° C., more preferably not higher than 60° C., even more preferably not higher than 40° C., and in particular in a temperature range of 15-35° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

A further aspect of the invention relates to a crystalline form A that is obtainable by the process as described above.

A further aspect of the present invention relates to a crystalline form B.

Preferably, the crystalline form B according to the invention has one or more X-ray diffraction peaks selected from the group consisting of 10.6±0.2 (2Θ), 17.2±0.2 (2Θ), 18.6±0.2 (2Θ), 19.3±0.2 (2Θ), 22.2±0.2 (2Θ), 26.7±0.2 (2Θ) and 29.3±0.2 (2Θ). In some preferred embodiments, the crystalline form comprises X-ray diffraction peaks at 18.6±0.2 (2Θ) and 19.3±0.2 (2Θ). In some preferred embodiments, the crystalline form comprises an X-ray diffraction peak at 18.6±0.2 (2Θ).

In some preferred embodiments, crystalline form B comprises X-ray diffraction peaks at 10.6±0.2 (2Θ), 17.2±0.2 (2Θ), 18.6±0.2 (2Θ), 19.3±0.2 (2Θ), 26.7±0.2 (2Θ), 29.3±0.2 (2Θ) and optionally at 22.2±0.2 (2Θ).

The crystalline form B according to the invention may additionally have at least one X-ray diffraction peak selected from the group consisting of 16.9±0.2 (2Θ), 21.2±0.2 (2Θ), 24.4±0.2 (2Θ), 28.6±0.2 (2Θ), 28.8±0.2 (2Θ), 30.0±0.2 (2Θ), 31.2±0.2 (2Θ) and 31.7±0.2 (2Θ).

Further, the crystalline form B according to the invention may be characterised in that as well as one or more X-ray diffraction peaks selected from the group consisting of 10.6±0.2 (2Θ), 17.2±0.2 (2Θ), 18.6±0.2 (2Θ), 19.3±0.2 (2Θ), 22.2±0.2 (2Θ), 26.7±0.2 (2Θ) and 29.3±0.2 (2Θ), and optionally one or more X-ray diffraction peaks selected from the group consisting of 16.9±0.2 (2Θ), 21.2±0.2 (2Θ), 24.4±0.2 (2Θ), 28.6±0.2 (2Θ), 28.8±0.2 (2Θ), 30.0±0.2 (2Θ), 31.2±0.2 (2Θ) and 31.7±0.2 (2Θ), it additionally has at least one X-ray diffraction peak selected from the group consisting of 8.4±0.2 (2Θ), 11.4±0.2 (2Θ), 12.5±0.2 (2Θ), 15.5±0.2 (2Θ), 20.7±0.2 (2Θ), 21.4±0.2 (2Θ), 25.4±0.2 (2Θ), 27.9±0.2 (2Θ) and 30.7±0.2 (2Θ).

The crystalline form B according to the invention may further be characterised in that as well as one or more X-ray diffraction peaks selected from the group consisting of 10.6±0.2 (2Θ), 17.2±0.2 (2Θ), 18.6±0.2 (2Θ), 19.3±0.2 (2Θ), 22.2±0.2 (2Θ), 26.7±0.2 (2Θ) and 29.3±0.2 (2Θ), and optionally one or more X-ray diffraction peaks selected from the group consisting of 16.9±0.2 (2Θ), 21.2±0.2 (2Θ), 24.4±0.2

(2Θ), 28.6±0.2 (2Θ), 28.8±0.2 (2Θ), 30.0±0.2 (2Θ), 31.2±0.2 (2Θ) and 31.7±0.2 (2Θ), and optionally one or more X-ray diffraction peaks selected from the group consisting of 8.4±0.2 (2Θ), 11.4±0.2 (2Θ), 12.5±0.2 (2Θ), 15.5±0.2 (2Θ), 20.7±0.2 (2Θ), 21.4±0.2 (2Θ), 25.4±0.2 (2Θ), 27.9±0.2 (2Θ) and 30.7±0.2 (2Θ), it additionally has at least one X-ray diffraction peak selected from the group consisting of 14.2±0.2 (2Θ), 27.1±0.2 (2Θ), 28.3±0.2 (2Θ), 32.9±0.2 (2Θ), 33.4±0.2 (2Θ), 33.8±0.2 (2Θ) and 34.7±0.2 (2Θ).

All 2Θ values refer to an X-ray diffractogram measured using CuKα radiation having a wavelength of 1.54060 Å.

In DSC analyses, the crystalline form B according to the present invention preferably exhibits an endothermal event with a peak temperature at 261-271° C., more preferably at 262-270° C., still more preferably at 263-269° C., yet more preferably at 264-268° C. and in particular at 265-268° C.

Preferably, the crystalline form B according to the present invention further exhibits an exothermal event, preferably within a temperature range of 210-265° C.

The crystalline form B according to the present invention may further be characterized in that it has one or more Raman bands selected from the group consisting of 1300±2 $cm^{-1}$, 1569±2 $cm^{-1}$, 1583±2 $cm^{-1}$ and 2992±2 $cm^{-1}$.

The crystalline form B according to the present invention may further be characterized in that it has one or more Raman bands selected from the group consisting of 1300±2 $cm^{-1}$, 1569±2 $cm^{-1}$, 1583±2 $cm^{-1}$ and 2992±2 $cm^{-1}$; and/or one or more Raman bands selected from the group consisting of 183±2 $cm^{-1}$, 919±2 $cm^{-1}$, 1001±2 $cm^{-1}$, 3054±2 $cm^{-1}$ and 3069±2 $cm^{-1}$; and/or one or more Raman bands selected from the group consisting of 160±2 $cm^{-1}$, 208±2 $cm^{-1}$, 491±2 $cm^{-1}$, 683±2 $cm^{-1}$, 1120±2 $cm^{-1}$, 1374±2 $cm^{-1}$, 1436±2 $cm^{-1}$, 1463±2 $cm^{-1}$, 1481±2 $cm^{-1}$, 2870±2 $cm^{-1}$, 2906±2 $cm^{-1}$, 2922±2 $cm^{-1}$, 2931±2 $cm^{-1}$, 2958±2 $cm^{-1}$ and 3034±2 $cm^{-1}$.

The crystalline form B according to the present invention may further be characterized in that it has one or more Raman bands selected from the group consisting of 255±2 $cm^{-1}$, 279±2 $cm^{-1}$, 371±2 $cm^{-1}$, 397±2 $cm^{-1}$, 430±2 $cm^{-1}$, 450±2 $cm^{-1}$, 466±2 $cm^{-1}$, 518±2 $cm^{-1}$, 540±2 $cm^{-1}$, 557±2 $cm^{-1}$, 568±2 $cm^{-1}$, 598±2 $cm^{-1}$, 606±2 $cm^{-1}$, 620±2 $cm^{-1}$, 628±2 $cm^{-1}$, 710±2 $cm^{-1}$, 768±2 $cm^{-1}$, 786±2 $cm^{-1}$, 808±2 $cm^{-1}$, 820±2 $cm^{-1}$, 828±2 $cm^{-1}$, 856±2 $cm^{-1}$, 873±2 $cm^{-1}$, 888±2 $cm^{-1}$, 928±2 $cm^{-1}$, 957±2 $cm^{-1}$, 984±2 $cm^{-1}$, 1028±2 $cm^{-1}$, 1035±2 $cm^{-1}$, 1047±2 $cm^{-1}$, 1073±2 $cm^{-1}$, 1136±2 $cm^{-1}$, 1174±2 $cm^{-1}$, 1199±2 $cm^{-1}$, 1216±2 $cm^{-1}$, 1222±2 $cm^{-1}$, 1265±2 $cm^{-1}$, 1352±2 $cm^{-1}$, 1628±2 $cm^{-1}$ and 2845±2 $cm^{-1}$.

Another aspect of the present invention relates to a process for the production of the crystalline form B described above comprising the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Conventional solvents known to persons skilled in the art may be used as solvents in a solution or suspension of this type, in particular water and organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

In an especially preferred embodiment, the organic solvent is a mixture of acetone and tetrahydrofuran. Preferably, the ratio between acetone and tetrahydrofuran is within the range of from 100:1 to 1:1, more preferably within the range of from 75:1 to 2:1, still more preferably within the range of from 50:1 to 5:1, yet more preferably within the range of from 40:1 to 10:1, most preferably within the range of from 35:1 to 15:1, and in particular within the range of from 30:1 to 15:1 (volume/volume).

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

In a preferred embodiment, the solution is a solution of hydrogen chloride in an organic solvent, especially preferred are alcohols such as ethanol, isopropanol and n-butanol, and ethers such as diethylether, di-isopropylether, tetrahydrofurane, methyl-tetrahydrofurane 1,4-dioxane.

In an especially preferred embodiment, the solution is a solution of hydrogen chloride in an aqueous solvent, hydrochloric acid is particularly preferred.

Preferably, the hydrogen-chloride containing solution and the solution of the free base contain the same solvent.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 hour, preferably at least 4 hours, more preferably at least 6 hours, still more preferably at least 12 hours, yet more preferably at least 18 hours, most preferably at least 1 day, and in particular at least 2 days.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine hydrochloride in a solvent.

Conventional solvents known to persons skilled in the art may be used as solvents in a suspension of this type, in particular organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; chlorinated hydrocarbons such as dichloromethane and chloroform; and also N-methyl-2-pyrrolidone, dimethyl formamide and dimethyl sulfoxide; and mixtures thereof. Saturated hydrocarbons, such as n-pentane, n-hexane and n-heptane, and water are less suitable, the compound (1r,4r)-6'-fluoro-N,N-dimethyl-4-phenyl-4',9'-dihydro-3'H-spiro[cyclohexane-1,1'-pyrano[3,4,b]indol]-4-amine hydrochloride being only poorly soluble in these substances.

Preferably, the solvent is selected from dichloromethane and mixtures of dichloromethane and methanol.

In a preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In an especially preferred embodiment, the process according to the invention further comprises the step (b-2) evaporating the solvent of the solution obtained in step (a-2).

Suitable methods for evaporating the solvent are known to a person skilled in the art. Preferably, in the process according to the invention, the solvent is evoporated in air, air flow, or inert gas flow, in particular argon or nitrogen flow. However, evaporating the solvent under vacuum, for example by means of a rotary evaporator, is also possible.

Preferably, in the process according to the invention, the solvent is evoporated at room temperature.

In another preferred embodiment, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water. Especially preferred media are ethyl acetate and acetonitril.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 90 minutes, more preferably at most 60 minutes, still more preferably at most 30 minutes, even more preferably at most 5 minutes, most preferably at most 60 seconds and in particular at most 10 seconds.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow.

In still another preferred embodiment, the process comprises the step of (a-3) suspending (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride in a solvent.

Conventional solvents known to persons skilled in the art may be used as solvents in a suspension of this type, in particular water and organic solvents selected from the group consisting of alcohols such as methanol, ethanol, n-propanol, iso-propanol and n-butanol; esters such as ethyl acetate, n-propyl acetate, iso-propyl acetate, n-butyl acetate and iso-butyl acetate; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; nitriles such as acetonitril; aromatic hydrocarbons such as toluene; saturated hydrocarbons such as n-pentane, n-hexane and n-heptane; chlorinated hydrocarbons such as dichloromethane and chloroform; and also N-methyl-2-pyrrolidone, dimethyl formamide and dimethyl sulfoxide; and mixtures thereof.

In a preferred embodiment, step (a-3) is carried out at a temperature not higher than 100° C., more preferably not higher than 90° C., still more preferably not higher than 80° C., yet more preferably not higher than 60° C., most preferably not higher than 40° C., and in particular in a temperature range of 15-35° C.

In another preferred embodiment, step (a-3) is carried out in a temperature range of 100-40° C., more preferably 90-50° C., and most preferably 85-60° C.

Preferably, in the process according to the invention, the suspension obtained in step (a-3) is stirred for a time period of at least 2 h, preferably at least 4 h, more preferably at least 8 h, still more preferably at least 12 h, yet more preferably at least 16 h, most preferably at least 24 h, and in particular at least 2 days.

Preferably, the process according to the invention further comprises the step (b-3) separating, preferably filtering off the solid obtained in step (a-3).

Preferably, the process according to the invention further comprises the step (c-3) drying of the solid obtained in step (b-3).

In the process according to the invention, step (c-3) may take place under air or inert gas flow, such as argon or nitrogen flow. However, drying under vacuum, more preferably at a vacuum of 0 to 900 mbar, even more preferably at a vacuum of 1 to 500 mbar, and in particular at a vacuum of 10 to 200 mbar is preferred.

Preferably, in the process according to the invention, step (c-3) takes place in a temperature range from 0 to 60° C., preferably from 10° C. to 50° C. more preferably from 20 to 40° C.

A further aspect of the invention relates to a crystalline form B that is obtainable by the process as described above.

A further aspect of the present invention relates to a crystalline form C.

Preferably, the crystalline form C according to the invention has one or more X-ray diffraction peaks selected from the group consisting of 9.1±0.2 (2Θ), 11.2±0.2 (2Θ), 18.2±0.2 (2Θ), 18.8±0.2 (2Θ), 19.1±0.2 (2Θ), 19.3±0.2 (2Θ), 24.0±0.2 (2Θ), 27.5±0.2 (2Θ) and 28.2±0.2 (2Θ). In some preferred embodiments, the crystalline form comprises X-ray diffraction peaks at 11.2±0.2 (2Θ), 18.2±0.2 (2Θ) and 27.5±0.2 (2Θ). In some preferred embodiments, the crystalline form comprises an X-ray diffraction peak at 18.2±0.2 (2Θ).

In some preferred embodiments, crystalline form C comprises X-ray diffraction peaks at 9.1±0.2 (2Θ), 11.2±0.2 (2Θ), 18.2±0.2 (2Θ), 18.8±0.2 (2Θ), 19.3±0.2 (2Θ), 24.0±0.2 (2Θ), 27.4±0.2 (2Θ), 28.2±0.2 (2Θ) and optionally 19.1±0.2 (2Θ).

The crystalline form C according to the invention may additionally have at least one X-ray diffraction peak selected from the group consisting of 22.4±0.2 (2Θ), 23.8±0.2 (2Θ), 24.3±0.2 (2Θ), 26.1±0.2 (2Θ), 26.4±0.2 (2Θ), 27.9±0.2 (2Θ), 31.6±0.2 (2Θ) and 34.1±0.2 (2Θ).

Further, the crystalline form C according to the invention may be characterised in that as well as one or more X-ray diffraction peaks selected from the group consisting of 9.1±0.2 (2Θ), 11.2±0.2 (2Θ), 18.2±0.2 (2Θ), 18.8±0.2 (2Θ), 19.1±0.2 (2Θ), 19.3±0.2 (2Θ), 24.0±0.2 (2Θ), 27.5±0.2 (2Θ) and 28.2±0.2 (2Θ), and optionally one or more X-ray diffraction peaks selected from the group consisting of 22.4±0.2 (2Θ), 23.8±0.2 (2Θ), 24.3±0.2 (2Θ), 26.1±0.2 (2Θ), 26.4±0.2 (2Θ), 27.9±0.2 (2Θ), 31.6±0.2 (2Θ) and 34.1±0.2 (2Θ), it additionally has at least one X-ray diffraction peak selected from the group consisting of 17.0±0.2 (2Θ), 24.5±0.2 (2Θ), 26.7±0.2 (2Θ), 29.2±0.2 (2Θ), 29.8±0.2 (2Θ), 32.0±0.2 (2Θ), 34.3±0.2 (2Θ) and 34.8±0.2 (2Θ).

The crystalline form C according to the invention may further be characterised in that as well as one or more X-ray diffraction peaks selected from the group consisting of 9.1±0.2 (2Θ), 11.2±0.2 (2Θ), 18.2±0.2 (2Θ), 18.8±0.2 (2Θ), 19.1±0.2 (2Θ), 19.3±0.2 (2Θ), 24.0±0.2 (2Θ), 27.5±0.2 (2Θ) and 28.2±0.2 (2Θ), and optionally one or more X-ray diffraction peaks selected from the group consisting of 22.4±0.2 (2Θ), 23.8±0.2 (2Θ), 24.3±0.2 (2Θ), 26.1±0.2 (2Θ), 26.4±0.2 (2Θ), 27.9±0.2 (2Θ), 31.6±0.2 (2Θ) and 34.1±0.2 (2Θ), and optionally one or more X-ray diffraction peaks selected from the group consisting of 17.0±0.2 (2Θ), 24.5±0.2 (2Θ), 26.7±0.2 (2Θ), 29.2±0.2 (2Θ), 29.8±0.2 (2Θ), 32.0±0.2 (2Θ), 34.3±0.2 (2Θ) and 34.8±0.2 (2Θ), it additionally has at least one X-ray diffraction peak selected from the group consisting of 7.8±0.2 (2Θ), 17.3±0.2 (2Θ), 21.7±0.2 (2Θ) and 23.4±0.2 (2Θ).

All 2Θ values refer to an X-ray diffractogram measured using CuKα radiation having a wavelength of 1.54060 Å.

The crystalline form C according to the present invention may further be characterized in that it has one or more Raman bands selected from the group consisting of 177±2 $cm^{-1}$, 1567±2 $cm^{-1}$ and 1584±2 $cm^{-1}$.

The crystalline form C according to the present invention may further be characterized in that it has one or more Raman bands selected from the group consisting of 177±2 $cm^{-1}$, 1567±2 $cm^{-1}$ and 1584±2 $cm^{-1}$; and/or one or more Raman bands selected from the group consisting of 158±2 $cm^{-1}$, 685±2 $cm^{-1}$, 918±2 $cm^{-1}$, 925±2 $cm^{-1}$, 1000±2 $cm^{-1}$, 1301±2 $cm^{-1}$ and 3072±2 $cm^{-1}$; and/or one or more Raman bands selected from the group consisting of 208±2 $cm^{-1}$, 253±2 $cm^{-1}$, 266±2 $cm^{-1}$, 370±2 $cm^{-1}$, 490±2 $cm^{-1}$, 600±2 $cm^{-1}$, 620±2 $cm^{-1}$, 628±2 $cm^{-1}$, 829±2 $cm^{-1}$, 1028±2 $cm^{-1}$, 1114±2 $cm^{-1}$, 1219±2 $cm^{-1}$, 1374±2 $cm^{-1}$, 1432±2 $cm^{-1}$, 1454±2 $cm^{-1}$, 1464±2 $cm^{-1}$, 1481±2 $cm^{-1}$, 1600±2 $cm^{-1}$ and 2959±2 $cm^{-1}$.

The crystalline form C according to the present invention may further be characterized in that it has one or more Raman bands selected from the group consisting of 322±2 $cm^{-1}$, 395±2 $cm^{-1}$, 429±2 $cm^{-1}$, 471±2 $cm^{-1}$, 516±2 $cm^{-1}$, 538±2 $cm^{-1}$, 567±2 $cm^{-1}$, 710±2 $cm^{-1}$, 772±2 $cm^{-1}$, 786±2 $cm^{-1}$, 889±2 $cm^{-1}$, 954±2 $cm^{-1}$, 986±2 $cm^{-1}$, 1055±2 $cm^{-1}$, 1076±2 $cm^{-1}$, 1136±2 $cm^{-1}$, 1167±2 $cm^{-1}$, 1200±2 $cm^{-1}$, 1267±2 $cm^{-1}$, 1359±2 $cm^{-1}$, 1628±2 $cm^{-1}$, 2842±2 $cm^{-1}$, 2880±2 $cm^{-1}$, 2901±2 $cm^{-1}$, 2927±2 $cm^{-1}$, 2994±2 $cm^{-1}$, 3031±2 $cm^{-1}$ and 3045±2 $cm^{-1}$.

Another aspect of the present invention relates to a process for the production of the crystalline form C described above comprising the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

The solution or suspension preferably contains water. In this embodiment, the solution or suspension preferably further contains a water miscible organic solvent, such as acetone or tetrahydrofuran.

Especially preferred solvents that may be used as solvents for the solution or suspension are mixtures of tetrahydrofuran and water.

In an especially preferred embodiment, the organic solvent is a mixture of water and tetrahydrofuran. Preferably, the ratio between water and tetrahydrofuran is within the range of from 50:1 to 1:50, more preferably within the range of from 30:1 to 1:20, still more preferably within the range of from 20:1 to 1:10, yet more preferably within the range of from 15:1 to 1:5, most preferably within the range of from 10:1 to 1:2, and in particular within the range of from 8:1 to 1:1 (volume/volume).

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

Preferably, the solution is a solution of hydrogen chloride in an aqueous solvent, hydrochloric acid is particularly preferred.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 hour, preferably at least 4 hours, more preferably at least 6 hours, still more preferably at least 12 hours, yet more preferably at least 18 hours, and most preferably at least 1 day.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place at a relative humidity of at least 50%, more preferably at least 60%, still more preferably at least 70%, yet more preferably at least 75%, most preferably at least 79%, and in particular at least 85% or at least 95%.

In another preferred embodiment, step (c-1) takes place under vacuum, preferably at a vacuum of 0 to 900 mbar, even more preferably at a vacuum of 1 to 500 mbar, and in particular at a vacuum of 10 to 200 mbar. In this embodiment, the solid obtained in step (b-1) is exposed to the vacuum for at most 12 h, more preferably at most 8 h, still more preferably at most 6 h, yet more preferably at most 4 h, most preferably at most 2 h, and in particular at most 1 h.

A further aspect of the invention relates to a crystalline form C that is obtainable by the process as described above.

A further aspect of the present invention relates to a crystalline form D.

Preferably, the crystalline form D according to the invention has one or more X-ray diffraction peaks selected from the group consisting of 16.3±0.2 (2Θ), 18.3±0.2 (2Θ), 18.9±0.2 (2Θ), 19.6±0.2 (2Θ), 23.7±0.2 (2Θ), 24.3±0.2 (2Θ), 27.6±0.2 (2Θ) and 28.9±0.2 (2Θ). In some preferred embodiments, the crystalline form comprises X-ray diffraction peaks at 18.3±0.2 (2Θ), 18.9±0.2 (2Θ) and 19.6±0.2 (2Θ). In some preferred embodiments, the crystalline form comprises an X-ray diffraction peak at 18.9±0.2 (2Θ).

In some preferred embodiments, crystalline form D comprises X-ray diffraction peaks at 18.3±0.2 (2Θ), 18.9±0.2 (2Θ), 19.6±0.2 (2Θ), 23.7±0.2 (2Θ), 24.3±0.2 (2Θ), 28.9±0.2 (2Θ), optionally 16.3±0.2 (2Θ) and optionally 27.6±0.2 (2Θ).

The crystalline form D according to the invention may additionally have at least one X-ray diffraction peak selected from the group consisting of 12.9±0.2 (2Θ), 16.9±0.2 (2Θ), 20.2±0.2 (2Θ), 21.6±0.2 (2Θ), 22.0±0.2 (2Θ), 23.3±0.2 (2Θ), 24.7±0.2 (2Θ), 28.6±0.2 (2Θ), 31.3±0.2 (2Θ) and 31.6±0.2 (2Θ).

Further, the crystalline form D according to the invention may be characterised in that as well as one or more X-ray diffraction peaks selected from the group consisting of 16.3±0.2 (2Θ), 18.3±0.2 (2Θ), 18.9±0.2 (2Θ), 19.6±0.2 (2Θ), 23.7±0.2 (2Θ), 24.3±0.2 (2Θ), 27.6±0.2 (2Θ) and 28.9±0.2 (2Θ), and optionally one or more X-ray diffraction peaks selected from the group consisting of 12.9±0.2 (2Θ), 16.9±0.2 (2Θ), 20.2±0.2 (2Θ), 21.6±0.2 (2Θ), 22.0±0.2 (2Θ), 23.3±0.2 (2Θ), 24.7±0.2 (2Θ), 28.6±0.2 (2Θ), 31.3±0.2 (2Θ) and 31.6±0.2 (2Θ), it additionally has at least one X-ray diffraction peak selected from the group consisting of 12.6±0.2 (2Θ), 15.6±0.2 (2Θ), 25.8±0.2 (2Θ), 26.4±0.2 (2Θ), 29.6±0.2 (2Θ), 30.0±0.2 (2Θ) and 33.1±0.2 (2Θ).

The crystalline form D according to the invention may further be characterised in that as well as one or more X-ray diffraction peaks selected from the group consisting of 16.3±0.2 (2Θ), 18.3±0.2 (2Θ), 18.9±0.2 (2Θ), 19.6±0.2 (2Θ), 23.7±0.2 (2Θ), 24.3±0.2 (2Θ), 27.6±0.2 (2Θ) and 28.9±0.2 (2Θ), and optionally one or more X-ray diffraction peaks selected from the group consisting of 12.9±0.2 (2Θ), 16.9±0.2 (2Θ), 20.2±0.2 (2Θ), 21.6±0.2 (2Θ), 22.0±0.2 (2Θ), 23.3±0.2 (2Θ), 24.7±0.2 (2Θ), 28.6±0.2 (2Θ), 31.3±0.2 (2Θ) and 31.6±0.2 (2Θ), and optionally one or more X-ray diffraction peaks selected from the group consisting of 12.6±0.2 (2Θ), 15.6±0.2 (2Θ), 25.8±0.2 (2Θ), 26.4±0.2 (2Θ), 29.6±0.2 (2Θ), 30.0±0.2 (2Θ) and 33.1±0.2 (2Θ), it additionally has at least one X-ray diffraction peak selected from the group consisting of 7.8±0.2 (2Θ), 9.1±0.2 (2Θ), 9.5±0.2 (2Θ), 10.8±0.2 (2Θ), 11.0±0.2 (2Θ) and 14.1±0.2 (2Θ).

All 2Θ values refer to an X-ray diffractogram measured using CuKα radiation having a wavelength of 1.54060 Å.

The crystalline form D according to the present invention may further be characterized in that it has one or more Raman bands selected from the group consisting of 161±2 $cm^{-1}$, 172±2 $cm^{-1}$, 180±2 $cm^{-1}$, 686±2 $cm^{-1}$, 919±2 $cm^{-1}$, 1004±2 $cm^{-1}$, 1299±2 $cm^{-1}$, 1567±2 $cm^{-1}$, 1573±2 $cm^{-1}$, 2912±2 $cm^{-1}$, 2957±2 $cm^{-1}$, 2981±2 $cm^{-1}$ and 3071±2 $cm^{-1}$.

The crystalline form D according to the present invention may further be characterized in that it has one or more Raman bands selected from the group consisting of 161±2 $cm^{-1}$, 172±2 $cm^{-1}$, 180±2 $cm^{-1}$, 686±2 $cm^{-1}$, 919±2 $cm^{-1}$, 1004±2 $cm^{-1}$, 1299±2 $cm^{-1}$, 1567±2 $cm^{-1}$, 1573±2 $cm^{-1}$, 2912±2 $cm^{-1}$, 2957±2 $cm^{-1}$, 2981±2 $cm^{-1}$ and 3071±2 $cm^{-1}$; and/or one or more Raman bands selected from the group consisting of 206±2 $cm^{-1}$, 252±2 $cm^{-1}$, 600±2 $cm^{-1}$, 829±2 $cm^{-1}$, 1308±2 $cm^{-1}$, 1374±2 $cm^{-1}$, 1443±2 $cm^{-1}$, 1466±2 $cm^{-1}$ and 2875±2 cm$^{-1}$; and/or one or more Raman bands selected from the group consisting of 278±2 cm$^{-1}$, 370±2 cm$^{-1}$, 392±2 cm$^{-1}$, 429±2 cm$^{-1}$, 490±2 cm$^{-1}$, 517±2 cm$^{-1}$, 620±2 cm$^{-1}$, 629±2 cm$^{-1}$, 676±2 cm$^{-1}$, 887±2 cm$^{-1}$, 983±2 cm$^{-1}$, 1028±2 cm$^{-1}$, 1035±2 cm$^{-1}$, 1045±2 cm$^{-1}$, 1116±2 cm$^{-1}$, 1161±2 cm$^{-1}$, 1197±2 cm$^{-1}$, 1217±2 cm$^{-1}$, 1263±2 cm$^{-1}$, 1355±2 cm$^{-1}$, 1627±2 cm$^{-1}$, 2845±2 cm$^{-1}$ and 3038±2 cm$^{-1}$.

The crystalline form D according to the present invention may further be characterized in that it has one or more Raman bands selected from the group consisting of 317±2 cm$^{-1}$, 401±2 cm$^{-1}$, 468±2 cm$^{-1}$, 538±2 cm$^{-1}$, 557±2 cm$^{-1}$, 569±2 cm$^{-1}$, 712±2 cm$^{-1}$, 771±2 cm$^{-1}$, 787±2 cm$^{-1}$, 869±2 cm$^{-1}$, 953±2 cm$^{-1}$, 1074±2 cm$^{-1}$, 1134±2 cm$^{-1}$, 1183±2 cm$^{-1}$, 1250±2 cm$^{-1}$ and 1339±2 cm$^{-1}$.

Another aspect of the present invention relates to a process for the production of the crystalline form D described above comprising the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Preferably, the solvent is selected from the group consisting of alcohols such as methanol, ethanol, n-propanol, isopropanol and n-butanol; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; chlorinated hydrocarbons such as dichloromethane and chloroform; and mixtures thereof.

Preferably, the solvent does not contain water.

Especially preferred are solvents selected from the group consisting of toluene, ethanol, n-propanol, isopropanol, n-butanol and 2-butanone.

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

Preferably, the solution is a solution of hydrogen chloride in an organic solvent, especially preferred are alcohols such as ethanol, isopropanol and n-butanol.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In another preferred embodiment, the suspension obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine hydrochloride in a solvent.

Preferably, the solvent is selected from the group consisting of dichloromethane, N-methyl-2-pyrrolidone, methanol, dimethyl formamide, and mixtures thereof.

In an especially preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step (b-2) evaporating the solvent of the solution obtained in step (a-2).

Suitable methods for evaporating the solvent are known to a person skilled in the art.

Preferably, in the process according to the invention, the solvent is evoporated in air, air flow, or inert gas flow, in particular argon or nitrogen flow. However, evaporating the solvent under vacuum, for example by means of a rotary evaporator, is also possible.

Preferably, in the process according to the invention, the solvent is evoporated at room temperature.

In another preferred embodiment, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water.

Especially preferred are tert-butyl methyl ether and diethyl ether.

The amount of the media in which (1r,4r)-6'-fluoro-N,N-dimethyl-4-phenyl-4',9'-dihydro-3'H-spiro[cyclohexane-1, 1'-pyrano[3,4,b]indol]-4-amine hydrochloride is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 60 minutes, more preferably at most 30 minutes, still more preferably at most 20 minutes, yet more preferably at most 10 minutes, most preferably at most 5 minutes, and in particular at most 3 minutes.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

In a preferred embodiment, step (d-2') takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

A further aspect of the invention relates to a crystalline form D that is obtainable by the process as described above.

A further aspect of the present invention relates to a crystalline form E (polymorph E).

Preferably, the crystalline form E according to the invention has one or more X-ray diffraction peaks selected from the group consisting of 9.1±0.2 (2Θ), 17.1±0.2 (2Θ), 17.7±0.2 (2Θ), 19.6±0.2 (2Θ), 21.3±0.2 (2Θ), 22.5±0.2 (2Θ), 23.6±0.2 (2Θ), 24.6±0.2 (2Θ) and 28.8±0.2 (2Θ). In some preferred embodiments, the crystalline form comprises X-ray diffraction peaks at 17.1±0.2 (2Θ), 17.7±0.2 (2Θ) and 19.6±0.2 (2Θ). In some preferred embodiments, the crystalline form comprises an X-ray diffraction peak at 19.6±0.2 (2Θ).

In some preferred embodiments, crystalline form E comprises X-ray diffraction peaks at 9.1±0.2 (2Θ), 17.1±0.2 (2Θ), 17.7±0.2 (2Θ), 19.6±0.2 (2Θ), 21.3±0.2 (2Θ), 22.5±0.2 (2Θ), 23.6±0.2 (2Θ), 24.6±0.2 (2Θ) and optionally 28.8±0.2 (2Θ).

The crystalline form E according to the invention may additionally have at least one X-ray diffraction peak selected from the group consisting of 18.3±0.2 (2Θ), 23.4±0.2 (2Θ), 24.1±0.2 (2Θ), 26.2±0.2 (2Θ), 26.8±0.2 (2Θ), 30.5±0.2 (2Θ) and 31.7±0.2 (2Θ).

Further, the crystalline form E according to the invention may be characterised in that as well as one or more X-ray diffraction peaks selected from the group consisting of 9.1±0.2 (2Θ), 17.1±0.2 (2Θ), 17.7±0.2 (2Θ), 19.6±0.2 (2Θ), 21.3±0.2 (2Θ), 22.5±0.2 (2Θ), 23.6±0.2 (2Θ), 24.6±0.2 (2Θ) and 28.8±0.2 (2Θ), and optionally one or more X-ray diffraction peaks selected from the group consisting of 18.3±0.2 (2Θ), 23.4±0.2 (2Θ), 24.1±0.2 (2Θ), 26.2±0.2 (2Θ), 26.8±0.2 (2Θ), 30.5±0.2 (2Θ) and 31.7±0.2 (2Θ), it additionally has at least one X-ray diffraction peak selected from the group consisting of 15.7±0.2 (2Θ), 18.9±0.2 (2Θ), 20.7±0.2 (2Θ), 25.1±0.2 (2Θ), 27.8±0.2 (2Θ), 30.2±0.2 (2Θ) and 34.8±0.2 (2Θ).

The crystalline form E according to the invention may further be characterised in that as well as one or more X-ray diffraction peaks selected from the group consisting of 9.1±0.2 (2Θ), 17.1±0.2 (2Θ), 17.7±0.2 (2Θ), 19.6±0.2 (2Θ), 21.3±0.2 (2Θ), 22.5±0.2 (2Θ), 23.6±0.2 (2Θ), 24.6±0.2 (2Θ) and 28.8±0.2 (2Θ), and optionally one or more X-ray diffraction peaks selected from the group consisting of 18.3±0.2 (2Θ), 23.4±0.2 (2Θ), 24.1±0.2 (2Θ), 26.2±0.2 (2Θ), 26.8±0.2 (2Θ), 30.5±0.2 (2Θ) and 31.7±0.2 (2Θ), and optionally one or more X-ray diffraction peaks selected from the group consisting of 15.7±0.2 (2Θ), 18.9±0.2 (2Θ), 20.7±0.2 (2Θ), 25.1±0.2 (2Θ), 27.8±0.2 (2Θ), 30.2±0.2 (2Θ) and 34.8±0.2 (2Θ), it additionally has at least one X-ray diffraction peak selected from the group consisting of 8.1±0.2 (2Θ), 10.6±0.2 (2Θ), 11.2±0.2 (2Θ), 11.6±0.2 (2Θ) and 13.3±0.2 (2Θ).

All 2Θ values refer to an X-ray diffractogram measured using CuKα radiation having a wavelength of 1.54060 Å.

The crystalline form E according to the present invention may further be characterized in that it has one or more Raman bands selected from the group consisting of 1569±2 $cm^{-1}$, 2963±2 $cm^{-1}$ and 3069±2 $cm^{-1}$.

The crystalline form E according to the present invention may further be characterized in that it has one or more Raman bands selected from the group consisting of 1569±2 $cm^{-1}$, 2963±2 $cm^{-1}$ and 3069±2 $cm^{-1}$; and/or one or more Raman bands selected from the group consisting of 160±2 $cm^{-1}$, 176±2 $cm^{-1}$, 686±2 $cm^{-1}$, 836±2 $cm^{-1}$, 917±2 $cm^{-1}$, 1003±2 $cm^{-1}$, 1299±2 $cm^{-1}$, 1308±2 $cm^{-1}$ and 1582±2 $cm^{-1}$; and/or one or more Raman bands selected from the group consisting of 211±2 $cm^{-1}$, 253±2 $cm^{-1}$, 369±2 $cm^{-1}$, 491±2 $cm^{-1}$, 599±2 $cm^{-1}$, 1029±2 $cm^{-1}$, 1200±2 $cm^{-1}$, 1220±2 $cm^{-1}$, 1376±2 $cm^{-1}$, 1441±2 $cm^{-1}$, 1465±2 $cm^{-1}$, 2855±2 $cm^{-1}$, 2873±2 $cm^{-1}$, 2889±2 $cm^{-1}$, 2986±2 $cm^{-1}$ and 3048±2 $cm^{-1}$.

The crystalline form E according to the present invention may further be characterized in that it has one or more Raman bands selected from the group consisting of 287±2 $cm^{-1}$, 317±2 cm⁻¹, 395±2 cm⁻¹, 433±2 cm⁻¹, 471±2 cm⁻¹, 517±2 cm⁻¹, 538±2 cm⁻¹, 558±2 cm⁻¹, 568±2 cm⁻¹, 619±2 cm⁻¹, 629±2 cm⁻¹, 676±2 cm⁻¹, 713±2 cm⁻¹, 786±2 cm⁻¹, 854±2 cm⁻¹, 870±2 cm⁻¹, 889±2 cm⁻¹, 952±2 cm⁻¹, 983±2 cm⁻¹, 993±2 cm⁻¹, 1019±2 cm⁻¹, 1047±2 cm⁻¹, 1076±2 cm⁻¹, 1107±2 cm⁻¹, 1117±2 cm⁻¹, 1133±2 cm⁻¹, 1142±2 cm⁻¹, 1166±2 cm⁻¹, 1267±2 cm⁻¹, 1353±2 cm⁻¹, 1494±2 cm⁻¹, 1630±2 cm⁻¹ and 3031±2 cm⁻¹.

Another aspect of the present invention relates to a process for the production of the crystalline form E described above comprising the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

The solution or suspension preferably comprises 1,4-dioxane. Preferably, the solution or suspension comprises 1,4-dioxane in an amount of at least 5 Vol.-%, more preferably at least Vol.-%, still more preferably at least 50 Vol.-%, yet more preferably at least 80 Vol.-%, most preferably at least 90 Vol.-%, and in particular at least 95 Vol.-%, based on the total volume of solvents contained in the solution or suspension. In particular, the solution or suspension contains 1,4-dioxane as the only solvent.

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

Preferably, the solution is a solution of hydrogen chloride in an organic solvent, especially preferred is 1,4-dioxane.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, the suspension obtained in step (a-1) is then stirred for a time period of preferably at most 1 day, preferably at most 4 hours, more preferably at most 60 minutes, still more preferably at most 30 minutes, yet more preferably at most 20 minutes, and most preferably at most 15 minutes, and in particular at most 10 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

Preferably, step (c-1) takes place under air or inert gas flow, such as argon or nitrogen flow.

A further aspect of the invention relates to a crystalline form E that is obtainable by the process as described above.

A further aspect of the present invention relates to a crystalline form F.

Preferably, the crystalline form F according to the invention has one or more X-ray diffraction peaks selected from the group consisting of 11.5±0.2 (2Θ), 14.5±0.2 (2Θ), 18.5±0.2 (2Θ), 19.3±0.2 (2Θ), 27.3±0.2 (2Θ) and 29.1±0.2 (2Θ). In some preferred embodiments, the crystalline form comprises X-ray diffraction peaks at 19.3±0.2 (2Θ) and 29.1±0.2 (2Θ). In some preferred embodiments, the crystalline form comprises an X-ray diffraction peak at 19.3±0.2 (2Θ).

In some preferred embodiments, crystalline form F comprises X-ray diffraction peaks at 14.5±0.2 (2Θ), 18.5±0.2 (2Θ), 19.3±0.2 (2Θ), 27.3±0.2 (2Θ), 29.1±0.2 (2Θ) and optionally 11.5±0.2 (2Θ).

The crystalline form F according to the invention may additionally have at least one X-ray diffraction peak selected from the group consisting of 21.2±0.2 (2Θ), 22.0±0.2 (2Θ), 27.5±0.2 (2Θ), 30.3±0.2 (2Θ) and 31.7±0.2 (2Θ).

Further, the crystalline form F according to the invention may be characterised in that as well as one or more X-ray diffraction peaks selected from the group consisting of 11.5±0.2 (2Θ), 14.5±0.2 (2Θ), 18.5±0.2 (2Θ), 19.3±0.2 (2Θ), 27.3±0.2 (2Θ) and 29.1±0.2 (2Θ), and optionally one or more X-ray diffraction peaks selected from the group consisting of 21.2±0.2 (2Θ), 22.0±0.2 (2Θ), 27.5±0.2 (2Θ), 30.3±0.2 (2Θ) and 31.7±0.2 (2Θ), it additionally has at least one X-ray diffraction peak selected from the group consisting of 16.1±0.2 (2Θ), 16.6±0.2 (2Θ), 19.9±0.2 (2Θ), 20.5±0.2 (2Θ), 23.2±0.2 (2Θ), 26.1±0.2 (2Θ), 26.5±0.2 (2Θ), and 30.7±0.2 (2Θ).

The crystalline form F according to the invention may further be characterised in that as well as one or more X-ray diffraction peaks selected from the group consisting of 11.5±0.2 (2Θ), 14.5±0.2 (2Θ), 18.5±0.2 (2Θ), 19.3±0.2 (2Θ), 27.3±0.2 (2Θ) and 29.1±0.2 (2Θ), and optionally one or more X-ray diffraction peaks selected from the group consisting of 21.2±0.2 (2Θ), 22.0±0.2 (2Θ), 27.5±0.2 (2Θ), 30.3±0.2 (2Θ) and 31.7±0.2 (2Θ), and optionally one or more X-ray diffraction peaks selected from the group consisting of 16.1±0.2 (2Θ), 16.6±0.2 (2Θ), 19.9±0.2 (2Θ), 20.5±0.2 (2Θ), 23.2±0.2 (2Θ), 26.1±0.2 (2Θ), 26.5±0.2 (2Θ), and 30.7±0.2 (2Θ), it additionally has at least one X-ray diffraction peak selected from the group consisting of 9.9±0.2 (2Θ), 10.5±0.2 (2Θ), 17.4±0.2 (2Θ), 24.5±0.2 (2Θ), 28.2±0.2 (2Θ), 32.0±0.2 (2Θ), 33.0±0.2 (2Θ) and 34.6±0.2 (2Θ).

All 2Θ values refer to an X-ray diffractogram measured using CuKα radiation having a wavelength of 1.54060 Å.

The crystalline form F according to the present invention may further be characterized in that it has one or more Raman bands selected from the group consisting of 160±2 cm⁻¹, 1295±2 cm⁻¹, 1573±2 cm⁻¹, 1585±2 cm⁻¹, 2979±2 cm⁻¹ and 3070±2 cm⁻¹.

The crystalline form F according to the present invention may further be characterized in that it has one or more Raman bands selected from the group consisting of 160±2 cm⁻¹, 1295±2 cm⁻¹, 1573±2 cm⁻¹, 1585±2 cm⁻¹, 2979±2 cm⁻¹ and 3070±2 cm⁻¹; and/or one or more Raman bands selected from the group consisting of 174±2 cm⁻¹, 206±2 cm⁻¹, 917±2 cm⁻¹, 1003±2 cm⁻¹ and 2954±2 cm⁻¹; and/or one or more Raman bands selected from the group consisting of 254±2 cm⁻¹, 598±2 cm⁻¹, 683±2 cm⁻¹, 1030±2 cm⁻¹, 1110±2 cm⁻¹, 1217±2 cm⁻¹, 1434±2 cm⁻¹, 1458±2 cm⁻¹, 1468±2 cm⁻¹, 2895±2 cm⁻¹, 2942±2 cm⁻¹ and 3029±2 cm⁻¹.

The crystalline form F according to the present invention may further be characterized in that it has one or more Raman bands selected from the group consisting of 273±2 cm⁻¹, 367±2 cm⁻¹, 390±2 cm⁻¹, 436±2 cm⁻¹, 488±2 cm⁻¹, 515±2 cm$^{-1}$, 538±2 cm$^{-1}$, 568±2 cm$^{-1}$, 620±2 cm$^{-1}$, 707±2 cm$^{-1}$, 769±2 cm$^{-1}$, 786±2 cm$^{-1}$, 829±2 cm$^{-1}$, 888±2 cm$^{-1}$, 980±2 cm$^{-1}$, 1047±2 cm$^{-1}$, 1132±2 cm$^{-1}$, 1170±2 cm$^{-1}$, 1201±2 cm$^{-1}$, 1264±2 cm$^{-1}$, 1368±2 cm$^{-1}$, 1486±2 cm$^{-1}$, 1629±2 cm$^{-1}$ and 2840±2 cm$^{-1}$.

Another aspect of the present invention relates to a process for the production of the crystalline form F described above comprising the step of (a-1) precipitating the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine from a solution or suspension of the free base.

Preferably, the solvent is selected from the group consisting of alcohols such as methanol, ethanol, n-propanol, isopropanol and n-butanol; ketones such as acetone, 2-butanone, pentan-2-one, pentan-3-one, hexan-2-one and hexan-3-one; ethers such as tert-butyl methyl ether, diethylether, tetrahydrofuran, diisopropylether and 1,4-dioxane; chlorinated hydrocarbons such as dichloromethane and chloroform; and mixtures thereof.

Preferably, the solvent does not contain water.

Step (a-1) may be carried out by the addition of hydrogen chloride.

In a preferred embodiment, the hydrogen chloride is added in form of hydrogen chloride gas.

In another preferred embodiment, the hydrogen chloride is produced in situ by means of a reaction, e.g. by the addition of trimethylsilyl chloride to an aqueous solution.

In still another preferred embodiment, the hydrogen chloride is in form of a solution.

Preferably, the solution is a solution of hydrogen chloride in an organic solvent, especially preferred are alcohols such as ethanol, isopropanol and n-butanol.

Preferably, the solution contains the hydrogen chloride in a concentration within the range of from 0.01 mol/L to 15 mol/L, more preferably within the range of from 0.02 mol/L to 12.5 mol/L, still more preferably within the range of from 0.05 mol/L to 10 mol/L, yet more preferably within the range of from 0.1 mol/L to 7.5 mol/L, most preferably within the range of from 0.2 mol/L to 10 mol/L, and in particular within the range of from 0.3 mol/L to 5 mol/L.

Preferably, the hydrogen chloride is added to the solution or suspension of the free base in molar excess.

Preferably, in the process according to the invention, step (a-1) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, in the process according to the invention, the suspension obtained in step (a-1) is stirred for a time period of at least 1 minute, preferably at least 2 minutes, more preferably at least 3 minutes, still more preferably at least 5 minutes, yet more preferably at least 10 minutes, most preferably at least 20 minutes, and in particular at least 30 minutes.

In another preferred embodiment, the suspension obtained in step (a-1) is stirred for a time period of at most 1 day, preferably at most 12 hours, more preferably at most 6 hours, still more preferably at most 2 hours, yet more preferably at most 60 minutes, and most preferably at most 45 minutes, and in particular at most 30 minutes.

Preferably, the process according to the invention further comprises the step (b-1) separating, preferably filtering off the solid obtained in step (a-1).

Preferably, the process according to the invention further comprises the step (c-1) drying of the solid obtained in step (b-1).

In a preferred embodiment, step (c-1) takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

Preferably, in the process according to the invention, step (c-1) takes place in a temperature range from 0 to 60° C., preferably from 10° C. to 50° C. more preferably from 20 to 40° C.

In another preferred embodiment, the process comprises the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine hydrochloride in a solvent.

Preferably, the solvent is selected from the group consisting of dichloromethane, N-methyl-2-pyrrolidone, methanol, dimethyl formamide, and mixtures thereof.

In an especially preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

In a preferred embodiment, the process according to the invention further comprises the step (b-2) evaporating the solvent of the solution obtained in step (a-2).

Suitable methods for evaporating the solvent are known to a person skilled in the art.

Preferably, in the process according to the invention, the solvent is evoporated in air, air flow, or inert gas flow, in particular argon or nitrogen flow. However, evaporating the solvent under vacuum, for example by means of a rotary evaporator, is also possible.

Preferably, in the process according to the invention, the solvent is evoporated at room temperature.

In another preferred embodiment, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble ("anti-solvent") to the solution obtained in step (a-2). Said medium is preferably selected from the group consisting of esters such as ethyl acetate, n-propyl acetate, iso-propyl acetate, n-butyl acetate and iso-butyl acetate; ethers such as tert-butyl methyl ether, diethyl ether and diisopropyl ether; ketones such as acetone, 2-butanone, pentan-2-one, pentan-3-one, hexan-2-one and hexan-3-one; nitriles such as acetonitril; pyridine, acetic acid and water.

Especially preferred are iso-butyl acetate and diethyl ether.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble, the precipitant or anti-solvent, is preferably selected in such a manner that upon its addition precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

The precipitation of the dissolved component preferably begins either immediately after the precipitant, preferably the total amount of the precipitant, has been added or alternatively with a delay of 2 seconds to 120 minutes. Preferably, the precipitation of the dissolved component begins within a time period of at most 60 minutes, more preferably at most 30 minutes, still more preferably at most 20 minutes, yet more preferably at most 10 minutes, most preferably at most 5 minutes, and in particular at most 3 minutes.

Preferably, in the process according to the invention, after step (b-2) or respectively (b-2'), all other steps are carried out at a temperature between 40 and 0° C., preferably between 35 and 5° C., more preferably between 25 and 15° C.

Preferably, in the process according to the invention, the suspension obtained in step (b-2') is stirred for a time period of at least 1 minute, preferably at least 2 minutes, more preferably at least 3 minutes, and most preferably at least 5 minutes.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

In a preferred embodiment, step (d-2') takes place under air or inert gas flow, such as argon or nitrogen flow.

In another preferred embodiment, step (c-1) takes place under vacuum, more preferably at a vacuum of 0 to 900 mbar, even more preferably at a vacuum of 1 to 500 mbar, and in particular at a vacuum of 10 to 200 mbar.

A further aspect of the invention relates to a crystalline form F that is obtainable by the process as described above.

A further aspect of the present invention relates to a crystalline form G.

Preferably, the crystalline form G according to the invention has one or more X-ray diffraction peaks selected from the group consisting of 21.4±0.2 (2Θ), 24.5±0.2 (2Θ), 25.2±0.2 (2Θ), 26.8±0.2 (2Θ), 30.5±0.2 (2Θ), 31.8±0.2 (2Θ) and 33.0±0.2 (2Θ). In some preferred embodiments, the crystalline form comprises X-ray diffraction peaks at 21.4±0.2 (2Θ) and 26.8±0.2 (2Θ). In some preferred embodiments, the crystalline form comprises an X-ray diffraction peak at 26.8±0.2 (2Θ).

The crystalline form G according to the invention may additionally have at least one X-ray diffraction peak selected from the group consisting of 13.3±0.2 (2Θ), 14.2±0.2 (2Θ), 21.8±0.2 (2Θ), 28.6±0.2 (2Θ), 30.0±0.2 (2Θ) and 31.3±0.2 (2Θ).

Further, the crystalline form G according to the invention may be characterised in that as well as one or more X-ray diffraction peaks selected from the group consisting of 21.4±0.2 (2Θ), 24.5±0.2 (2Θ), 25.2±0.2 (2Θ), 26.8±0.2 (2Θ), 30.5±0.2 (2Θ), 31.8±0.2 (2Θ) and 33.0±0.2 (2Θ), and optionally one or more X-ray diffraction peaks selected from the group consisting of 13.3±0.2 (2Θ), 14.2±0.2 (2Θ), 21.8±0.2 (2Θ), 28.6±0.2 (2Θ), 30.0±0.2 (2Θ) and 31.3±0.2 (2Θ), it additionally has at least one X-ray diffraction peak selected from the group consisting of 18.6±0.2 (2Θ), 26.2±0.2 (2Θ), 27.4±0.2 (2Θ), 34.2±0.2 (2Θ) and 34.8±0.2 (2Θ).

All 2Θ values refer to an X-ray diffractogram measured using CuKα radiation having a wavelength of 1.54060 Å.

The crystalline form G according to the present invention may further be characterized in that it has one or more Raman bands selected from the group consisting of 274±2 $cm^{-1}$, 642±2 $cm^{-1}$, 1028±2 $cm^{-1}$, 3053±2 $cm^{-1}$ and 3077±2 $cm^{-1}$.

The crystalline form G according to the present invention may further be characterized in that it has one or more Raman bands selected from the group consisting of 200±2 $cm^{-1}$, 293±2 $cm^{-1}$, 445±2 $cm^{-1}$, 560±2 $cm^{-1}$, 623±2 $cm^{-1}$, 654±2 $cm^{-1}$, 700±2 $cm^{-1}$, 774±2 $cm^{-1}$, 835±2 $cm^{-1}$, 846±2 $cm^{-1}$, 894±2 $cm^{-1}$, 986±2 $cm^{-1}$, 1005±2 $cm^{-1}$, 1070±2 $cm^{-1}$, 1146±2 $cm^{-1}$, 1193±2 $cm^{-1}$, 1242±2 $cm^{-1}$, 1304±2 $cm^{-1}$, 1361±2 $cm^{-1}$, 1422±2 $cm^{-1}$, 1446±2 $cm^{-1}$, 1512±2 $cm^{-1}$, 1582±2 $cm^{-1}$, 1636±2 $cm^{-1}$, 2986±2 $cm^{-1}$, 3006±2 $cm^{-1}$, 3019±2 $cm^{-1}$, 3089±2 $cm^{-1}$ and 3164±2 $cm^{-1}$.

Another aspect of the present invention relates to a process for the production of the crystalline form G described above comprising the step of (a-2) dissolving (1r,4r)-6'-fluoro-N,N-dimethyl-4-phenyl-4',9'-dihydro-3'H-spiro[cyclohexane-1,1'-pyrano[3,4,b]indol]-4-amine hydrochloride in a solvent.

Preferably, the solvent is selected from the group consisting of dichloromethane, N-methyl-2-pyrrolidone, methanol, dimethyl formamide, and mixtures thereof.

In an especially preferred embodiment, the organic solvent is a mixture of dichloromethane and methanol. Preferably, the ratio between dichloromethane and methanol is within the range of from 10:1 to 1:10, more preferably within the range of from 7:1 to 1:5, still more preferably within the range of from 6:1 to 1:3, yet more preferably within the range of from 5:1 to 1:1, most preferably within the range of from 4:1 to 2:1, and in particular within the range of from 3.5:1 to 2.5:1 (volume/volume).

Preferably, in the process according to the invention, step (a-2) is carried out at a temperature below or at the boiling point of the respective solvent, preferably at a temperature not higher than 80° C., more preferably not higher than 60° C., even more preferably not higher than 40° C., and in particular in a temperature range of 20-40° C.

Preferably, the process further comprises the step of (b-2') precipitating (1r,4r)-6'-fluoro-N,N-dimethyl-4-phenyl-4',9'-dihydro-3'H-spiro[cyclo-hexane-1,1'-pyrano[3,4,b]indol]-4-amine hydrochloride from the solution obtained in step (a-2).

Suitable methods of precipitation are known to a person skilled in the art. In the process according to the invention, step (b-2') may be carried out by reducing the volume of the solution obtained in step (a-2) and/or by cooling of the solution, preferably to a temperature of at most 15° C., more preferably at most 10° C., even more preferably at most 4-8° C. and/or by cooling of the solution, preferably to a temperature of at least 10° C., more preferably at least 30° C., even more preferably at least 60° C. below the temperature according to step (a-2).

In a preferred embodiment, step (b-2') is carried out by the addition of a medium in which (1r,4r)-6'-fluoro-N,N-dimethyl-4-phenyl-4',9'-dihydro-3'H-spiro[cyclohexane-1,1'-pyrano-[3,4,b]indol]-4-amine hydrochloride is only poorly soluble (anti-solvent) to the solution obtained in step (a-2).

Preferably, said medium is pyridine.

The amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble, the precipitant or anti-solvent, is preferably selected in such a manner that within a time period of up to 2 days, preferably up to one day, precipitation of the dissolved component begins.

The total amount of the media in which (1r,4r)-6'-fluoro-N,N-dimethyl-4-phenyl-4',9'-dihydro-3'H-spiro[cyclohexane-1,1'-pyrano[3,4,b]indol]-4-amine hydrochloride is only poorly soluble may also be divided into several portions, preferably two or three portions. In this embodiment, the precipitation of the dissolved component preferably begins after the addition of the last portion.

Preferably, in the process according to the invention, after step (b-2) or respectively (b-2'), all other steps are carried out at a temperature between 40 and 0° C., preferably between 35 and 5° C., more preferably between 25 and 15° C.

Preferably, the process according to the invention further comprises the step (c-2') separating, preferably filtering off the precipitate obtained in step (b-2').

Preferably, the process according to the invention further comprises the step (d-2') drying of the solid obtained in step (c-2').

Preferably, in the process according to the invention, step (d-2') takes place under air or inert gas flow, such as argon or nitrogen flow.

A further aspect of the invention relates to a crystalline form G that is obtainable by the process as described above.

In some embodiments, the solid forms of the present invention make it possible to obtain (1r,4r)-6'-fluoro-N,N-dimethyl-4-phenyl-4',9'-dihydro-3'H-spiro[cyclohexane-1,1'-pyrano-[3,4,b]indol]-4-amine in form of the hydrochloride with high yields and purity. These forms are further distinguished in that they have fundamentally different properties, which may provide advantages.

In some embodiments, the solid forms of the present invention are characterized by higher ease-of-handling and allow for more precise (or even exact) metering of the active ingredient.

In some embodiments, it has been surprisingly found that (1r,4r)-6'-fluoro-N,N-dimethyl-4-phenyl-4',9'-dihydro-3'H-spiro[cyclohexane-1,1'-pyrano[3,4,b]indol]-4-amine hydrochloride is capable of forming four ansolvate forms (crystalline forms A, B, D and F), a hydrate (crystalline form C) and two different solvates with organic solvents (crystalline forms E and G).

In some embodiments, it has been surprisingly found that crystalline forms A, D and E or mixtures thereof are obtained by crystallization techniques with short equilibration times. In some embodiments, it has been surprisingly found that crystalline form A represents the most dominant form obtainable by these fast crystallization techniques.

In some embodiments, it has been found that crystalline form A is not hygroscopic. In some embodiments, it has been found that crystalline form A may be obtained from crystalline form C by drying.

In some embodiments, it has been found that crystalline form B is obtained by slower crystallization techniques, such as suspension equilibration. In some embodiments, it has surprisingly been found that crystalline forms A, B, C, D and F may be converted into crystalline form B by these slower crystallization techniques. In some embodiments, it has been found that crystalline form B represents the thermodynamically most stable form at room temperature.

Mixtures of the crystalline forms A, B, C, D, E, F and G, preferably mixtures of two or three of these crystalline forms, are also included within the scope of the present invention.

For example, mixtures of crystalline forms A and C may be obtained from crystalline form C by a partial loss of hydrate water or mixtures of crystalline forms A and B may be obtained from suspensions containing crystalline form A by partial suspension equilibration.

In a preferred embodiment, the crystalline form according to the invention is subsequently converted into an amorphous form.

In another aspect the present invention relates to a solid form, in particular a crystalline form and/or an amorphous form as described herein for use in the treatment of pain.

In another aspect the present invention relates to methods of treating pain, comprising administering a solid form as described herein to a patient in need thereof (for example, a patient who has been diagnosed with a pain disorder).

In another aspect the present invention relates to methods of treating pain, comprising administering a pharmaceutical composition that comprises a solid form as described herein to a patient in need thereof (for example, a patient who has been diagnosed with a pain disorder). The term pain as used herein preferably includes but is not limited to pain selected from the group consisting of inflammatory pain, postoperative pain, neuropathic pain, diabetic neuropathic pain, acute pain, chronic pain, visceral pain, migraine pain and cancer pain. In some preferred embodiments, the solid form, in particular the crystalline form and/or the amorphous form according to the invention is for use in the treatment of acute, visceral, neuropathic or chronic pain (cf. WO 2008/040481).

In another aspect the present invention relates to a pharmaceutical composition comprising a solid form, in particular a crystalline form and/or an amorphous form as described herein and optionally one or more suitable additives and/or adjuvants such as described below.

In some preferred embodiments, the pharmaceutical composition comprises between about 0.001% by weight and about 40% by weight of one or more of the solid forms, in particular crystalline forms and/or amorphous forms described herein. In some preferred embodiments, the pharmaceutical composition comprises between about 0.001% by weight and about 20% by weight of one or more of the solid forms, in particular crystalline forms and/or amorphous forms described herein. In some preferred embodiments, the pharmaceutical composition comprises between about 0.001% by weight and about 10% by weight of one or more of the solid forms, in particular crystalline forms and/or amorphous forms described herein. In some preferred embodiments, the pharmaceutical composition comprises between about 0.001% by weight and about 5% by weight of one or more of the solid forms, in particular crystalline forms and/or amorphous forms described herein. In some preferred embodiments, the pharmaceutical composition comprises between about 0.001% by weight and about 1% by weight of one or more of the solid forms, in particular crystalline forms and/or amorphous forms described herein. In some preferred embodiments, the pharmaceutical composition comprises between about 0.01% by weight and about 1% by weight of one or more of the solid forms, in particular crystalline forms and/or amorphous forms described herein.

Suitable methods for determining the content of the hydrochloric acid salt of (1r,4r)-6'-fluoro-N,N-dimethyl-4-phenyl-4',9'-dihydro-3'H-spiro[cyclohexane-1,1'-pyrano[3,4,b]indol]-4-amine are known to those skilled in the art and include e.g. XRPD, elemental analysis, Raman spectroscopy, infrared spectroscopy, chromatographic methods, NMR spectroscopy, thermal analysis, electrophoresis, atom absorption spectroscopy, energy dispersive X-ray spectroscopy thermal methods comprise, among others, e.g. DSC, TGA, modulated temperature DSC, high-speed DSC, melting point, hot-stage XRPD, hot-stage microscopy, heat of solution, microthermal analysis, calorimetry, micro-calorimetry.

Preferably the pharmaceutical composition may be used for the treatment of pain.

In still another aspect the present invention relates to a medicament comprising a solid form, in particular a crystalline form and/or an amorphous form as described herein. In a preferred embodiment, the medicament is a solid drug form. The medicament is preferably manufactured for oral administration. However, other forms of administration are also possible, e.g. for buccal, sublingual, transmucosal, rectal, intralumbal, intraperitoneal, transdermal, intravenous, intramuscular, intragluteal, intracutaneous and subcutaneous application.

Depending on the configuration, the medicament (dosage form) preferably contains suitable additives and/or adjuvants. Suitable additives and/or adjuvants in the sense of the invention are all substances known to a person skilled in the art for the formation of galenic formulations. The choice of these adjuvants and also the quantities to be used are dependent on how the medication is to be administered, i.e. orally, intravenously, intraperitoneally, intradermally, intramuscularly, intranasally, buccally or locally.

In some preferred embodiments, the dosage form comprises 40±35 µg, more preferably 40±30 µg, still more preferably 40±25 µg, yet more preferably 40±20 µg, even more preferably 40±15 µg, most preferably 40±10 µg, and in particular 40±5 µg of one or more of the crystalline forms described herein. In some other preferred embodiments, the dosage form comprises 400±375 µg or 400±350 µg, more preferably 400±300 µg, still more preferably 400±250 µg, yet more preferably 400±200 µg, even more preferably 400±150 µg, most preferably 40±100 µg, and in particular 400±50 µg of one or more of the crystalline forms described herein.

Preparations suitable for oral administration are those in the form of tablets, chewable tablets, lozenges, capsules, granules, drops, liquids or syrups, and those suitable for parenteral, topical and inhalatory, administration are solutions, suspensions, easily reconstituted dry preparations and sprays. A further possibility is suppositories for rectal administration. The application in a depot in dissolved form, a patch or a plaster, possibly with the addition of agents promoting skin penetration, are examples of suitable percutaneous forms of administration.

Examples of adjuvants and additives for oral forms of application are disintegrants, lubricants, binders, fillers, mould release agents, possibly solvents, flavourings, sugar, in particular carriers, diluents, colouring agents, antioxidants etc.

Waxes or fatty acid esters, amongst others, can be used for suppositories and carrier substances, preservatives, suspension aids etc. can be used for parenteral forms of application.

Adjuvants can be, for example: water, ethanol, 2-propanol, glycerine, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl-cellulose, cellulose acetate, shellac, cetyl alcohol, polyvinylpyrrolidone, paraffins, waxes, natural and synthetic rubbers, acacia gum, alginates, dextran, saturated and unsaturated fatty acids, stearic acid, magnesium stearate, zinc stearate, glyceryl stearate, sodium lauryl sulfate, edible oils, sesame oil, coconut oil, peanut oil, soybean oil, lecithin, sodium lactate, polyoxyethylene and propylene fatty acid esters, sorbitane fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidon, agar and bentonite.

The production of these medicaments and pharmaceutical compositions is conducted using means, devices, methods and processes that are well known in the art of pharmaceutical technology, as described, for example, in "*Remington's Pharmaceutical Sciences*", A. R. Gennaro, 17th ed., Mack Publishing Company, Easton, Pa. (1985), in particular in part 8, chapters 76 to 93.

Thus, for example, for a solid formulation such as a tablet, the active substance of the drug can be granulated with a pharmaceutical carrier substance, e.g. conventional tablet constituents such as cornstarch, lactose, saccharose, sorbitol, talc, magnesium stearate, dicalcium phosphate or pharmaceutically acceptable rubbers, and pharmaceutical diluents such as water, for example, in order to form a solid composition that contains the active substance in a homogenous dispersion. Homogenous dispersion is understood here to mean that the active substances are uniformly dispersed throughout the composition, so that this can be readily divided into identically effective standard dosage forms such as tablets, capsules, lozenges. The solid composition is then divided into standard dosage forms. The tablets or pills can also be coated or otherwise compounded to prepare a slow release dosage form. Suitable coating agents include polymeric acids and mixtures of polymeric acids with materials such as shellac, cetyl alcohol and/or cellulose acetate, for example.

In one embodiment of the present invention the solid form, in particular the crystalline form and/or the amorphous form as described herein is present in immediate release form.

In another embodiment of the present invention the solid form, in particular the crystalline form and/or the amorphous form as described herein is at least partially present in controlled-release form. In particular, the active ingredient can be released slowly from preparations that can be applied orally, rectally or percutaneously.

The medicament can preferably be manufactured for administration once daily, twice daily (bid), or three times daily, the once daily or twice daily administration (bid) being preferred.

The term controlled release as used herein refers to any type of release other than immediate release such as delayed release, sustained release, slow release, extended release and the like. These terms are well known to any person skilled in the art as are the means, devices, methods and processes for obtaining such type of release.

In another embodiment of the present invention
the medicament is manufactured for oral administration; and/or
the medicament is a solid and/or compressed and/or film-coated drug form; and/or
the medicament releases the solid form, in particular the crystalline form and/or the amorphous form as described herein slowly from a matrix; and/or
the medicament contains the solid form, in particular the crystalline form and/or the amorphous form in a quantity of 0.001 to 99.999% by wt., more preferred 0.1 to 99.9% by wt., still more preferred 1.0 to 99.0% by wt., even more preferred 2.5 to 80% by wt., most preferred 5.0 to 50% by wt. and in particular 7.5 to 40% by wt., based on the total weight of the medicament; and/or the medicament contains a pharmaceutically compatible carrier and/or pharmaceutically compatible adjuvants; and/or the medicament has a total mass in the range of 25 to 2000 mg, more preferred 50 to 1800 mg, still more preferred 60 to 1600 mg, more preferred 70 to 1400 mg, most preferred 80 to 1200 mg and in particular 100 to 1000 mg; and/or the medicament is selected from the group comprising tablets, capsules, pellets and granules.

The medicament can be provided as a simple tablet and as a coated tablet (e.g. as film-coated tablet or lozenge). The tablets are usually round and biconvex, but oblong forms are also possible. Granules, spheres, pellets or microcapsules, which are contained in sachets or capsules or are compressed to form disintegrating tablets, are also possible.

In yet another one of its aspects, the present invention relates to the use of the solid form, in particular the crystalline form and/or the amorphous form as described herein for the production of a medicament. Preferably said medicament is suitable for the treatment of pain.

In still another one of its aspects, the present invention relates to the use of the solid form, in particular the crystalline form and/or the amorphous form as described herein for the treatment of pain.

Furthermore, the present invention relates to a method for treating pain in a patient, preferably in a mammal, which comprises administering an effective amount of a solid form, in particular a crystalline form and/or an amorphous form as described herein to a patient.

EXAMPLES

The following examples serve to explain the invention in more detail, but should not be interpreted as restrictive.

The following abbreviations are used in the examples:
iBuOAc iso-butyl acetate
1BuOH n-butanol (1-butanol)
DMSO dimethylsulfoxid
EtOAc ethyl acetate
EtOH ethanol
h hour(s)
IPE diisopropyl ether
MeCN acetonitril
MEK 2-butanone
MeOH methanol
min minute(s)
NMP N-methyl-2-pyrrolidone
1PrOH n-propanol (1-propanol)
2PrOH iso-propanol (2-propanol)
RT room temperature, preferably 20-25° C.
sec seconds
TBME tert-butyl methyl ether
THF tetrahydrofuran
NMR nuclear magnetic resonance spectroscopy
PXRD powder x-ray diffraction
XRPD x-ray powder diffraction
SCXRD single crystal x-ray diffraction
FT Raman Fourier-Transform Raman spectroscopy
TG-FTIR thermogravimetry coupled with Fourier-Transform infrared spectroscopy
DSC differential scanning calorimetry
DVS dynamic vapour sorption Unless otherwise specified, solvent mixtures are always volume/volume.

Synthesis of (1r,4r)-6'-fluoro-N,N-dimethyl-4-phenyl-4',9'-dihydro-3'H-spiro[cyclohexane-1,1'-pyrano[3,4,b]indol]-4-amine (4-(dimethylamino)-4-phenylcyclohexanone (3 g, 13.82 mmol), 2-(5-fluoro-1H-indol-3-yl)ethanol (2.47 g, 13.82 mmol) and 150 mL dichloromethane were charged to a flask at 0° C. A solution of trifluoromethane sulfonic acid trimethylsilylester (3 mL, 15.5 mmol) in 3 mL dichloromethane were added quickly. The reaction mixture changed color to violet and the temperature rose to 10° C. The reaction mixture was cooled in an ice bath and stirred for 20 min. Meanwhile a solid precipitated. The ice bath was removed and the reaction mixture was stirred for 3 to 3.5 hours at room temperature. Subsequently 50 mL of NaOH (1N) were added and the reaction mixture was stirred further 10 min. The colour changed to yellow and a solid precipitated. In order to complete the precipitation the reaction mixture (two liquid phases) was stirred for further 20 min while cooled in an ice bath. Eventually the solid was filtered out. The resulting solid (4.2 g) was subsequently recrystallized in 800 mL 2-Propanol. Yield: 3.5 g.

To enhance the yield, the liquid (Water and Dichloromethane) filtrate was separated. The aqueous solution with extracted 3 times with 20 mL Dichloromethane. The organic phases were united and dried with $MgSO_4$ and subsequently the solvent was stripped off until dryness. The resulting solid (1.7 g) was subsequently recrystallized under reflux in 800 mL 2-Propanol.

A) Synthesis of Crystalline Form A 303 mg (1r,4r)-6'-fluoro-N,N-dimethyl-4-phenyl-4',9'-dihydro-3'H-spiro[cyclohexane-1,1'-pyrano[3,4,b]indol]-4-amine were dissolved in 50 mL acetone and 2 mL THF. 1.6 mL of hydrochloric acid (0.5 M in $H_2O$) was added. The salt precipitated out after short time of stirring. The resulting suspension was stirred for 1 day at RT. The resulting solids were filtered out and dried in air. A crystalline solid of crystalline form A was obtained and characterized by NMR, PXRD, FT Raman, TG-FTIR, DSC, elemental analysis and DVS (cf. Section "Analysis").

B) Synthesis of Crystalline Form B 3.07 g (1r,4r)-6'-fluoro-N,N-dimethyl-4-phenyl-4',9'-dihydro-3'H-spiro[cyclohexane-1,1'-pyrano[3,4,b]indol]-4-amine were suspended in 520 mL acetone/THF 25:1 (v/v). Only a small amount of solid remained. 18 mL of hydrochloric acid (0.5 M in $H_2O$) were slowly added and the formation of further precipitate was observed. The suspension was stirred for 5 days at RT. The resulting solids were filtered out and dried for 1.5 h under vacuum. A crystalline solid (2.35 g, 70%) of crystalline form B was obtained and characterized by NMR, PXRD, FT Raman, TG-FTIR, DSC, elemental analysis and DVS (cf. Section "Analysis").

The purity of the compound was determined by HPLC and was found to be >99.9%. The impurity peak that typically is present in the HPLC spectrum of the free base was found to be below the detection limit in this sample. Therefore, converting the free base into the hydrochloric acid addition salt and subsequent crystallization of the resulting hydrochloride salt apparently purifies the compound.

Example 1

Acid-Base Reaction Experiments (1r,4r)-6'-fluoro-N,N-dimethyl-4-phenyl-4',9'-dihydro-3'H-spiro[cyclohexane-1,1'-pyrano-[3,4,b]indol]-4-amine (in form of the free base) was dissolved or suspended in different solvents at RT. In case that a turbid solution was obtained, the solution was filtered. Then hydrochloric acid was added to the solution. The resulting suspension was stirred at RT for different times. The resulting solids were filtered out, dried under different conditions (vacuum, nitrogen flow or at different relative humidities) and characterized by PXRD and/or FT Raman.

The detailed experimental conditions and results are summarized in the table here below. For characterization details of the obtained forms see Section "Analysis".

TABLE 1

| Ex. | solvent(s) | amount free base/ amount solvent | HCl solution | stirring time | drying | outcome[1] (crystall. form) | remarks |
|---|---|---|---|---|---|---|---|
| 1-1 | acetone/THF 25:1 (v/v) | 3.07 g/520 mL | 0.5M in H$_2$O, 18 mL | 5 days | vacuum | B | |
| 1-2 | acetone/THF 17:1 (v/v) | 205 mg/36 mL | 0.5M in H$_2$O, 0.94 mL | 1 h | vacuum | A, B | |
| 1-3 | acetone/THF 17:1 (v/v) | 202 mg/36 mL | 0.5M in H$_2$O, 1.07 mL | 6 days | vacuum | B | after 1 h: A; after 6 days: B |
| 1-4 | THF/H$_2$O 1:1 (v/v) | 206 mg/14.5 mL | 0.5M in H$_2$O, 1.1 mL | 1 h | vacuum | "H" | mixture containing C |
| 1-5 | 1,4-dioxane | 197 mg/14.5 mL | 0.5M in H$_2$O, 1.1 mL | 0.5 h | vacuum | A, B | |
| 1-6 | THF | 80 mg/7 mL | 0.5M in H$_2$O, 0.49 mL | 3 min | N$_2$ flow | A | |
| 1-7 | CH$_2$Cl$_2$ | 83 mg/25 mL | 1.25M in EtOH, 0.21 mL | 1 h | N$_2$ flow | A | |
| 1-8 | toluene | 56 mg/37 mL | 1.25M in EtOH, 0.14 mL | 10 min | N$_2$ flow | D | |
| 1-9 | 1BuOH | 89 mg/35 mL | 3M in 1BuOH, 0.09 mL | 1 h | N$_2$ flow | D | |
| 1-10 | MEK | 108 mg/21 mL | 3M in 1BuOH, 0.11 mL | 5 min | N$_2$ flow | D | |
| 1-11 | 1,4-dioxane | 83 mg/8 mL | 4M in dioxane, 0.07 mL | 5 min | N$_2$ flow, then vacuum | E | converts to E, A, D upon drying |
| 1-12 | MeOH | 106 mg/35 mL | 1.25M in EtOH, 0.26 mL | 1 h | N$_2$ flow | A | |
| 1-13 | THF/H$_2$O[2] 1:1.1 (v/v) | 102 mg/16 mL | 0.5M in H$_2$O, 0.62 mL | 1 h | vacuum | C (wet), then A (dry) | converts to A upon drying |
| 1-14 | THF/H$_2$O[2] 1:1.1 (v/v) | 202 mg/32 mL | 0.5M in H$_2$O, 1.2 mL | 2 days | at 97% r.h., then vacuum | C (wet), A (dry) | |
| 1-15 | THF/H$_2$O[2] 1:1.1 (v/v) | 196 mg/32 mL | 0.5M in H$_2$O, 1.2 mL | 2 days | at 75.5% r.h. | A, C | |
| 1-16 | THF/H$_2$O[2] 1:7.4 (v/v) | 80 mg/39.3 mL | 0.5M in H$_2$O, 0.48 mL | 2 days | at 79.5% r.h. | C, A | |
| 1-17 | THF/H$_2$O[2] 1:7.4 (v/v) | 79 mg/39.3 mL | 0.5M in H$_2$O, 0.48 mL | 2 days | at 54.5% r.h. | A, C | |
| 1-18 | 2PrOH | 202 mg/10 mL | 1.25M in 2PrOH, 0.49 mL | 4 days | N$_2$ flow | A | |
| 1-19 | 2PrOH | 490 mg/10 mL | 1.25M in 2PrOH, 1.2 mL | 2.5 h | vacuum | mixture of known forms or new form | |
| 1-20 | THF | 415 mg/35 mL | 0.5M in H$_2$O, 2.51 mL | 0.5 h | vacuum | A | |

[1] determined by PXRD and/or FT Raman; bold: main component in mixture
[2] the sample was dissolved in THF and a small amount of H$_2$O, then the rest of the H$_2$O was added as precipitant It becomes evident from the above table that in experiments with long suspension equilibration times, mainly form B was obtained, whereas forms A, D and E were found in experiments with short equilibration times. Form C is probably a hydrate and was only found in experiments containing substantial amounts of water. It converts to crystalline form A upon drying. The amorphous form was not observed.

Example 2

Fast Precipitation Experiments

Three stock solutions were prepared as follows:

Stock solution a: 110 mg crystalline form B was suspended in 40 mL NMP. The suspension was stirred for 2 h. The remaining small amount of precipitate was removed by filtration.

Stock solution b: 254 mg crystalline form B was suspended in 40 mL CH$_2$Cl$_2$/MeOH 3:1 (v/v). The suspension was stirred for 1 day. The remaining small amount of precipitate was removed by filtration.

Stock solution c: 246 mg crystalline form B was suspended in 40 mL CH$_2$Cl$_2$/MeOH 3:1 (v/v). The suspension was stirred for 3 days. The remaining small amount of precipitate was removed by filtration.

In each precipitation experiment 10 mL of stock solution were quickly added to 10 mL of an anti-solvent. In some cases another portion of anti-solvent (20 mL) was added subsequently.

The resulting suspension was stirred at RT for a while. The resulting solid was filtered out, dried (at air or nitrogen flow) and characterized by PXRD and/or FT Raman.

The detailed experimental conditions and results are summarized in the table here below. For characterization details of the obtained forms see Section "Analysis".

TABLE 2

| Ex. | stock solution | anti-solvent | stirring time | drying | outcome[1] (crystall. form) |
|---|---|---|---|---|---|
| 2-1 | a | water (10 mL) | 15 min, then stored in the fridge for 2 weeks | — | not enough precipitate for analysis |
| 2-2 | a | EtOAc, (10 mL) | 15 min, then stored in the fridge for 1 month | air | A |
| 2-3 | b | EtOAc (10 mL + 20 mL) | 10 min | N₂ flow | F, B |
| 2-4 | b | MeCN (10 mL + 20 mL) | 1 h | N₂ flow | A, B |
| 2-5 | b | acetone (10 mL + 20 mL) | 1 h | N₂ flow | A |
| 2-6 | b | TBME (10 mL + 20 mL) | 5 min | N₂ flow | D |
| 2-7 | c | diethyl ether (10 mL + 20 mL) | 5 min | N₂ flow | D, F (and A) |
| 2-8 | c | iBuOAc (10 mL + 20 mL) | 5 min | N₂ flow | F |
| 2-9 | c | aceticacid (10 mL + 20 mL) | 1 day, then stored in the fridge for 15 days | — | noprecipitation (solutionslightlyturbid) |
| 2-10 | c | pyridine (10 mL + 20 mL) | 1 day | N₂ flow | G |

[1]bold: main component in mixture

It becomes evident from the above table that by means of the fast precipitation technique mainly forms A, D, F and G were obtained. In some samples small amounts of form B were found in mixture with A or F. The amorphous form was not observed.

Example 3

Suspension Equilibration Experiments

The following experiments were designed to identify (thermodynamically) more stable polymorphs. In each suspension equilibration experiment the starting material was suspended in the solvent and stirred for several days. The resulting solid was filtered out, dried (under vacuumor at air) and characterized by PXRD and/or FT Raman.

The detailed experimental conditions and results are summarized in the table here below. For characterization details of the obtained forms see Section "Analysis".

It becomes evident from the above table that, with one exception, always crystalline form B was obtained. Even mixtures of crystalline forms A, B, C, D and F converted to crystalline form B, indicating that crystalline form B is the most stable ansolvate form at RT. Only a suspension of crystalline form A in water did not convert to another form within 7 days. This is probably because the solubility of crystalline form A in water is very low (1.21 mg/L), i.e. the equilibration time is very long.

Example 4

Vapor Diffusion Experiments

These experiments were designed to grow single crystals of the forms suitable for SCXRD. In each experiment, an undersaturated solution of crystalline form B was prepared

TABLE 3

| Ex. | starting material: form | solvent(s) | amount starting material/ amount solvent | stirring time, T/° C. | drying | outcome (crystall. form) |
|---|---|---|---|---|---|---|
| 3-1 | A | H₂O | 200 mg/2 mL | 7 days, RT | vacuum | A |
| 3-2 | B | NMP | 71 mg/3 mL | 4 days, RT | vacuum | B |
| 3-3 | B | CH₂Cl₂ | 55 mg/3 mL | 4 days, RT | air | B |
| 3-4 | B | NMP/water 1:1 (v/v) | 64 mg/3 mL | 4 days, RT | vacuum | B |
| 3-5 | B | NMP/water 3:1 (v/v) | 64 mg/3 mL | 4 days, RT | vacuum | B |
| 3-6 | B | NMP | 88 mg/3 mL | 1 day, 80° C. | vacuum | B |
| 3-7 | B | EtOH | 93 mg/3 mL | 3 days, 70° C. | vacuum | B |
| 3-8 | B | DMSO | 170 mg/5 mL | 4 days, RT | vacuum | B |
| 3-9 | A, B | acetone/THF/water | 150 mg/ 3 mL/120 µL/108 µL | 4 days, RT | vacuum | B |
| 3-10 | A, B, C, D, F | CH₂Cl₂/MeOH 3:1 (v/v) | (60/60/40/40/10) mg/3 mL[1] | 4 days, RT | vacuum | B |
| 3-11 | A, B, C, D, F | acetone/THF 17:1 (v/v) | (45/80/40/30/10) mg/ 3 mL[1] | 4 days, RT | vacuum | B |
| 3-12 | B | H₂O | product of exp. 3-11/ 3 mL | 9 days, RT | air | B |

[1]The solvent mixture was saturated with crystalline form B prior to adding to the mixture of the other polymorphs and exposed to an atmosphere containing the antisolvent. The diffusion processes lower the solubility and subsequent crystallization occurs.

Two solvent/anti-solvent systems at two different temperatures were used.

Preparation of a stock solution for experiments 4-1) and 4-2):

110 mg crystalline form B was suspended in 40 mL NMP. The resulting suspension was stirred for 2 hours at RT and the remaining small amount of solid was removed by filtration (0.20 μm).

Preparation of a stock solution for experiments 4-3) and 4-4):

29 mg crystalline form B was suspended in 20 mL $CH_2Cl_2$. The resulting suspension was stirred for 2 hours at RT and the remaining large amount of solid was removed by filtration (0.20 μm).

In each vapor diffusion experiment, 10 mL of the respective stock solution were exposed to an atmosphere containing the anti-solvent at different temperatures (RT or 4° C.) for different times. The resulting solids were analyzed by SCXRD. From the SCXRD data the corresponding PXRD pattern was calculated and compared to the measured PXRD spectra of the different crystalline forms (as obtained from the other experiments).

The detailed experimental conditions and results are summarized in the table here below. For characterization details of the obtained forms see Section "Analysis".

TABLE 4

| Ex. | starting material: form | solvent/anti-solvent | T/° C. | time | outcome | crystalline form[1] |
|---|---|---|---|---|---|---|
| 4-1 | B | NMP/EtOH | RT | weeks | no precipitation | — |
| 4-2 | B | NMP/EtOH | 4° C. | weeks | no precipitation | — |
| 4-3 | B | $CH_2Cl_2$/hexane | RT | days | precipitation of a white solid after 1 day | A |
| 4-4 | B | $CH_2Cl_2$/hexane | 4° C. | weeks | precipitation after 2 weeks | D[2] |

[1]as determined by comparison of the calculated PXRD spectrum with measured PXRD spectra of the crystalline forms (as obtained from other experiments);
[2]see comment below.

The sample of experiment 4-3) most likely corresponds to crystalline form A. The calculated PXRD pattern of sample 4-4) resembles the measured PXRD pattern of crystalline form D. However, due to the fact that the SCXRD and PXRD experiment were performed at different temperatures, it is not possible to say with high certainty that this sample indeed corresponds to crystalline form D.

Example 5

Evaporation Experiment

An undersaturated solution of crystalline form B was prepared by dissolving 46 mg crystalline form B in 40 mL $CH_2Cl_2$. The solvent was evaporated under vacuum in 45 minutes. The remaining solid was dried for 2 hours under vacuum. Crystalline form B was obtained.

Example 6

The effect of mechanical stress from grinding with an agate mortar was analyzed.

6-1) A sample of crystalline form A was grinded in an agate mortar for 10 min. The resulting solid was characterized by PXRD. Except for a slightly increased background signal probably due to the higher bulk density after grinding, no significant difference compared to the PXRD spectrum before grinding was observed. No additional peaks were observed after grinding, i.e. crystalline form A does not convert to another form upon grinding for 10 minutes to a significant extent.

6-2) A sample of crystalline form B was grinded in an agate mortar for 10 min. The resulting solid was characterized by PXRD. Except for a slightly increased background signal probably due to the higher bulk density after grinding and a slightly broadening of the peaks probably due to a reduction of the crystallite size upon grinding, no significant difference compared to the PXRD spectrum before grinding was observed. No additional peaks were observed after grinding, i.e. crystalline form B does not convert to another form upon grinding for 10 minutes to a significant extent.

Analysis—NMR

The $^1$H-NMR spectra of crystalline forms A, B and C complied with the structure of (1r,4r)-6'-fluoro-N,N-dimethyl-4-phenyl-4',9'-dihydro-3'H-spiro[cyclohexane-1,1'-pyrano[3,4,b]indol]-4-amine hydrochloride. The $^1$H-NMR spectra show peak shifts compared to the spectrum of the free base, also indicating the salt formation.

Analysis—Elemental Analysis

Form A

The result of the elemental composition analysis is given in Table 5. It confirms the salt formation.

TABLE 5

| Element | Found | Calculated |
|---|---|---|
| C | 69.05 | 69.47 |
| H | 6.82 | 6.80 |
| N | 6.69 | 6.75 |
| O | 4.23 | 3.86 |
| Cl | 8.53 | 8.54 |
| F | 4.70 | 4.58 |

Form B

The result of the elemental composition analysis is given in Table 6. It confirms the salt formation.

TABLE 6

| Element | Found | Calculated[1] | Calculated[2] |
|---|---|---|---|
| C | 68.37 | 69.47 | 69.16 |
| H | 6.66 | 6.80 | 6.82 |
| N | 6.60 | 6.75 | 6.72 |
| O | 3.92 | 3.86 | 4.23 |
| Cl | 9.21 | 8.54 | 8.51 |
| F | 4.62 | 4.58 | 4.56 |

[1]Calculated assuming no water is present;
[2]Calculated assuming 0.44% water is present.

Form C

Elemental composition analysis was performed with a sample of Ex. 1-4, i.e. on a mixture containing mainly C and something else. The result of the elemental composition analysis is given in Table 7. It does not comply with the assumed stoichiometry. However, the sample lost weight during the experiment, i.e. an exact weighting out for the elemental analysis was not possible.

TABLE 7

| Element | Found | Calculated[1] | Calculated[2] |
|---|---|---|---|
| C | 54.21 | 69.47 | 46.16 |
| H | 7.25 | 6.80 | 8.27 |
| N | 5.25 | 6.75 | 4.49 |
| O | 18.21 | 3.86 | 32.37 |
| Cl | 6.93 | 8.54 | 5.68 |
| F | 3.42 | 4.58 | 3.04 |

[1] Calculated assuming no water is present;
[2] Calculated assuming 33.56% water is present.

Analysis—XRPD (X-Ray Powder Diffraction)

XRPD analyses were carried out in transmission geometry with a Philips X'pert PW 3040 X-ray powder diffractometer, monochromatised CuKα radiation being used by means of a germanium monochrystal. d-distances were calculated from the 2θ values, the wavelength of 1.54060 Å being taken as basis. The d-value analysis was performed with the software EVA version 10, 0, 0, 0. The CuKα$_2$ was removed by the software and only lines up to 35° 2θ were listed. In general, the 2θ values have an error rate of ±0.20 in 2θ. The experimental error in the d-distance values is therefore dependent on the location of the peak. D-distance values can be calculated from 2θ values using Bragg's law. The samples were measured without any special treatment other than the application of slight pressure to get a flat surface. An ambient air atmosphere was used. To avoid contamination of the equipment, the samples were sealed with capton foil.

Crystalline Form A

FIG. 1a shows the PXRD pattern of crystalline form A. Table 8 shows the peak list for crystalline form A. The uncertainty in the 2θ values is ±0.20 in 2θ; rel. I is the relative intensity of the respective peaks. Maximum relative intensity is 100.

TABLE 8

| 2θ | d value Å | Intensity Cps | rel. I % |
|---|---|---|---|
| 8.4 | 10.5 | 505 | 46 |
| 10.8 | 8.2 | 782 | 72 |
| 12.3 | 7.2 | 54 | 5 |
| 13.1 | 6.8 | 76 | 7 |
| 17.0 | 5.2 | 955 | 87 |
| 17.5 | 5.1 | 592 | 54 |
| 18.9 | 4.7 | 942 | 86 |
| 20.0 | 4.4 | 347 | 32 |
| 20.7 | 4.3 | 437 | 40 |
| 21.6 | 4.1 | 262 | 24 |
| 22.3 | 4.0 | 185 | 17 |
| 22.6 | 3.9 | 158 | 14 |
| 23.3 | 3.8 | 151 | 14 |
| 23.6 | 3.8 | 161 | 15 |
| 24.1 | 3.7 | 270 | 25 |
| 25.5 | 3.5 | 1094 | 100 |
| 26.3 | 3.4 | 223 | 20 |
| 26.8 | 3.3 | 151 | 14 |
| 27.9 | 3.2 | 311 | 29 |
| 28.4 | 3.1 | 238 | 22 |
| 29.2 | 3.1 | 150 | 14 |
| 30.2 | 3.0 | 290 | 27 |
| 30.8 | 2.9 | 302 | 28 |
| 31.5 | 2.8 | 86 | 8 |
| 32.4 | 2.8 | 158 | 14 |
| 33.7 | 2.7 | 194 | 18 |
| 34.3 | 2.6 | 430 | 39 |
| 34.6 | 2.6 | 261 | 24 |

Crystalline Form B

FIG. 1b shows the PXRD pattern of crystalline form B. Table 9 shows the peak list for crystalline form B. The uncertainty in the 2θ values is ±0.20 in 2θ; rel. I is the relative intensity of the respective peaks. Maximum relative intensity is 100.

TABLE 9

| 2θ | d value Å | Intensity Cps | rel. I % |
|---|---|---|---|
| 8.4 | 10.5 | 177 | 6 |
| 10.6 | 8.4 | 535 | 17 |
| 11.4 | 7.8 | 183 | 6 |
| 12.5 | 7.1 | 182 | 6 |
| 14.2 | 6.2 | 168 | 5 |
| 15.5 | 5.7 | 208 | 7 |
| 16.9 | 5.2 | 311 | 10 |
| 17.2 | 5.2 | 609 | 19 |
| 18.6 | 4.8 | 3206 | 100 |
| 19.3 | 4.6 | 732 | 23 |
| 20.7 | 4.3 | 245 | 8 |
| 21.2 | 4.2 | 335 | 10 |
| 21.4 | 4.1 | 181 | 6 |
| 22.2 | 4.0 | 470 | 15 |
| 24.4 | 3.7 | 318 | 10 |
| 25.4 | 3.5 | 186 | 6 |
| 26.7 | 3.3 | 618 | 19 |
| 27.1 | 3.3 | 154 | 5 |
| 27.9 | 3.2 | 197 | 6 |
| 28.3 | 3.2 | 156 | 5 |
| 28.6 | 3.1 | 360 | 11 |
| 28.8 | 3.1 | 390 | 12 |
| 29.3 | 3.0 | 580 | 18 |
| 30.0 | 3.0 | 308 | 10 |
| 30.7 | 2.9 | 243 | 8 |
| 31.2 | 2.9 | 405 | 13 |
| 31.7 | 2.8 | 386 | 12 |
| 32.9 | 2.7 | 162 | 5 |
| 33.4 | 2.7 | 129 | 4 |
| 33.8 | 2.7 | 117 | 4 |
| 34.7 | 2.6 | 170 | 5 |

Crystalline form C

Figure 1C:
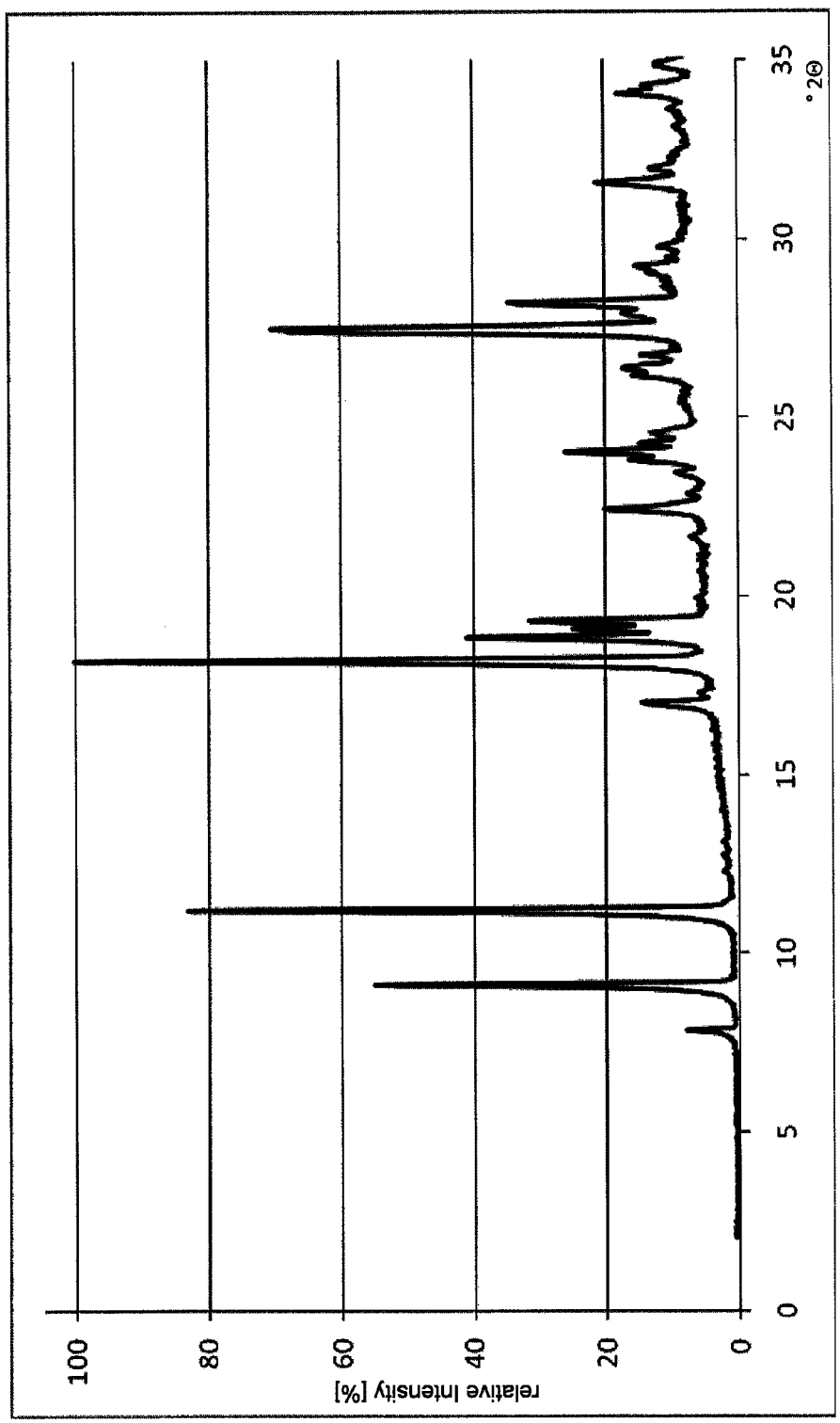

FIG. 1c shows the PXRD pattern of crystalline form C. Table 10 shows the peak list for crystalline form C. The uncertainty in the 2θ values is ±0.20 in 2θ; rel. I is the relative intensity of the respective peaks. Maximum relative intensity is 100.

TABLE 10

| 2θ | d value Å | Intensity Cps | rel. I % |
|---|---|---|---|
| 7.8 | 11.3 | 147 | 8 |
| 9.1 | 9.7 | 967 | 52 |
| 11.2 | 7.9 | 1521 | 82 |
| 17.0 | 5.2 | 265 | 14 |
| 17.3 | 5.1 | 107 | 6 |
| 18.2 | 4.9 | 1867 | 100 |
| 18.8 | 4.7 | 785 | 42 |
| 19.1 | 4.7 | 469 | 25 |
| 19.3 | 4.6 | 565 | 30 |
| 21.7 | 4.1 | 132 | 7 |
| 22.4 | 4.0 | 369 | 20 |
| 23.4 | 3.8 | 160 | 9 |
| 23.8 | 3.7 | 292 | 16 |
| 24.0 | 3.7 | 500 | 27 |
| 24.3 | 3.7 | 278 | 15 |
| 24.5 | 3.6 | 221 | 12 |
| 26.1 | 3.4 | 291 | 16 |
| 26.4 | 3.4 | 315 | 17 |
| 26.7 | 3.3 | 253 | 14 |
| 27.5 | 3.3 | 1283 | 69 |
| 27.9 | 3.2 | 310 | 17 |
| 28.2 | 3.2 | 644 | 35 |
| 29.2 | 3.1 | 266 | 14 |
| 29.8 | 3.0 | 220 | 12 |
| 31.6 | 2.8 | 395 | 21 |

TABLE 10-continued

| 2θ | d value Å | Intensity Cps | rel. I % |
|---|---|---|---|
| 32.0 | 2.8 | 249 | 13 |
| 34.1 | 2.6 | 346 | 19 |
| 34.3 | 2.6 | 265 | 14 |
| 34.8 | 2.6 | 225 | 12 |

Crystalline Form D

FIG. 1d shows the PXRD pattern of crystalline form D. Table 11 shows the peak list for crystalline form D. The uncertainty in the 2θ values is ±0.2° in 2θ; rel. I is the relative intensity of the respective peaks. Maximum relative intensity is 100.

TABLE 11

| 2θ | d value Å | Intensity Cps | rel. I % |
|---|---|---|---|
| 7.8 | 11.3 | 72 | 9 |
| 9.1 | 9.7 | 75 | 10 |
| 9.5 | 9.3 | 75 | 10 |
| 10.8 | 8.2 | 55 | 7 |
| 11.0 | 8.0 | 51 | 7 |
| 12.6 | 7.0 | 128 | 17 |
| 12.9 | 6.9 | 186 | 24 |
| 14.1 | 6.3 | 72 | 9 |
| 15.6 | 5.7 | 93 | 12 |
| 16.3 | 5.4 | 232 | 30 |
| 16.9 | 5.3 | 181 | 24 |
| 18.3 | 4.8 | 422 | 55 |
| 18.9 | 4.7 | 772 | 100 |
| 19.6 | 4.5 | 561 | 73 |
| 20.2 | 4.4 | 185 | 24 |
| 21.6 | 4.1 | 177 | 23 |
| 22.0 | 4.0 | 185 | 24 |
| 23.3 | 3.8 | 169 | 22 |
| 23.7 | 3.8 | 313 | 41 |
| 24.3 | 3.7 | 248 | 32 |
| 24.7 | 3.6 | 169 | 22 |
| 25.8 | 3.5 | 141 | 18 |
| 26.4 | 3.4 | 148 | 19 |
| 27.6 | 3.2 | 233 | 30 |
| 28.6 | 3.1 | 176 | 23 |
| 28.9 | 3.1 | 242 | 31 |
| 29.6 | 3.0 | 112 | 15 |
| 30.0 | 3.0 | 127 | 16 |
| 31.3 | 2.9 | 175 | 23 |
| 31.6 | 2.8 | 162 | 21 |
| 33.1 | 2.7 | 110 | 14 |

Crystalline Form E

FIG. 1e shows the PXRD pattern of crystalline form E. Table 12 shows the peak list for crystalline form E. The uncertainty in the 2θ values is ±0.2° in 2θ; rel. I is the relative intensity of the respective peaks. Maximum relative intensity is 100.

TABLE 12

| 2θ | d value Å | Intensity Cps | rel. I % |
|---|---|---|---|
| 8.1 | 10.9 | 66 | 7 |
| 9.1 | 9.7 | 267 | 29 |
| 10.6 | 8.3 | 41 | 4 |
| 11.2 | 7.9 | 91 | 10 |
| 11.6 | 7.6 | 52 | 6 |
| 13.3 | 6.6 | 123 | 13 |
| 15.7 | 5.7 | 159 | 17 |
| 17.1 | 5.2 | 508 | 55 |
| 17.7 | 5.0 | 649 | 70 |
| 18.3 | 4.9 | 190 | 21 |

TABLE 12-continued

| 2θ | d value Å | Intensity Cps | rel. I % |
|---|---|---|---|
| 18.9 | 4.7 | 154 | 17 |
| 19.6 | 4.5 | 926 | 100 |
| 20.7 | 4.3 | 158 | 17 |
| 21.3 | 4.2 | 288 | 31 |
| 22.5 | 4.0 | 277 | 30 |
| 23.4 | 3.8 | 191 | 21 |
| 23.6 | 3.8 | 306 | 33 |
| 24.1 | 3.7 | 206 | 22 |
| 24.6 | 3.6 | 312 | 34 |
| 25.1 | 3.5 | 160 | 17 |
| 26.2 | 3.4 | 198 | 21 |
| 26.8 | 3.3 | 182 | 20 |
| 27.8 | 3.2 | 150 | 16 |
| 28.8 | 3.1 | 244 | 26 |
| 30.2 | 3.0 | 141 | 15 |
| 30.5 | 2.9 | 198 | 21 |
| 31.7 | 2.8 | 194 | 21 |
| 34.8 | 2.6 | 174 | 19 |

Crystalline Form F

Figure 1F:
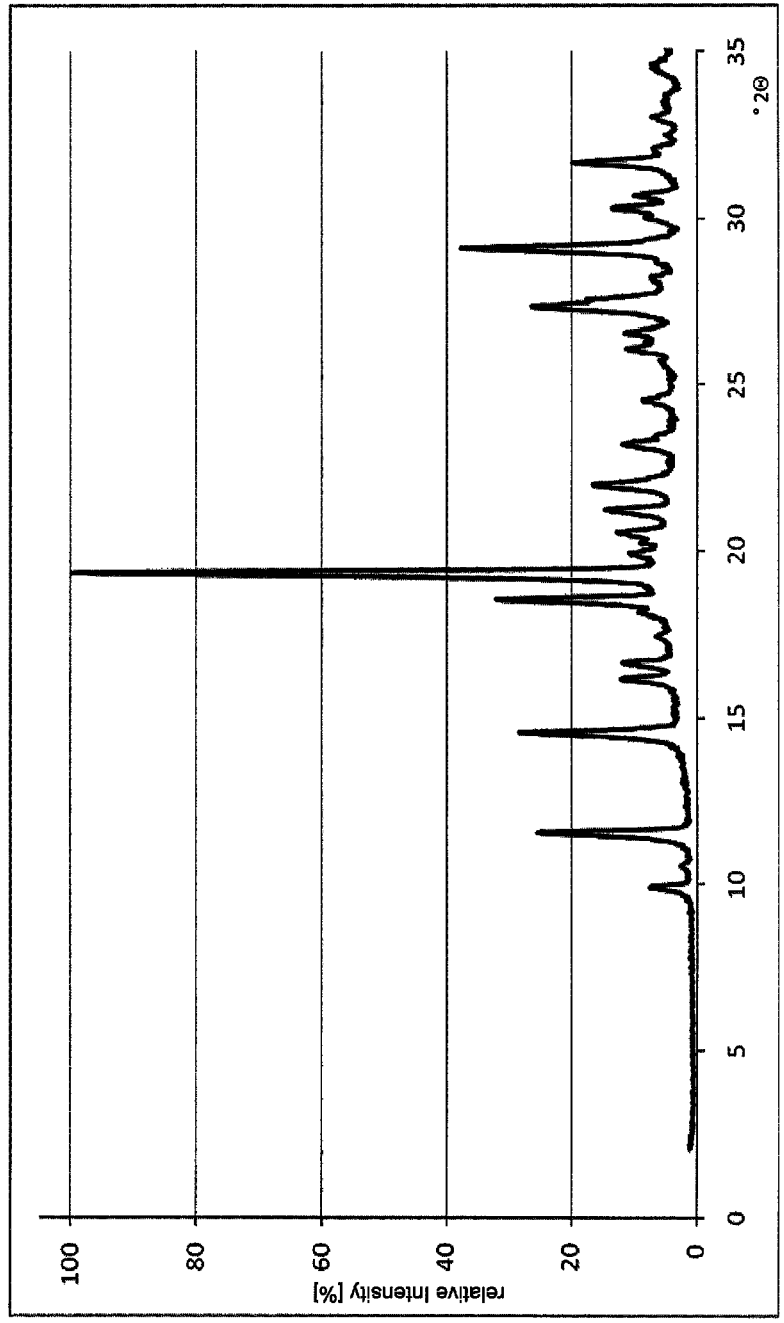

FIG. 1f shows the PXRD pattern of crystalline form F. Table 13 shows the peak list for crystalline form F. The uncertainty in the 2θ values is ±0.2° in 2θ; rel. I is the relative intensity of the respective peaks. Maximum relative intensity is 100.

TABLE 13

| 2θ | d value Å | Intensity Cps | rel. I % |
|---|---|---|---|
| 9.9 | 8.9 | 130 | 9 |
| 10.5 | 8.4 | 44 | 3 |
| 11.5 | 7.7 | 390 | 26 |
| 14.5 | 6.1 | 444 | 29 |
| 16.1 | 5.5 | 190 | 12 |
| 16.6 | 5.3 | 182 | 12 |
| 17.4 | 5.1 | 104 | 7 |
| 18.5 | 4.8 | 495 | 32 |
| 19.3 | 4.6 | 1529 | 100 |
| 19.9 | 4.5 | 164 | 11 |
| 20.5 | 4.3 | 203 | 13 |
| 21.2 | 4.2 | 225 | 15 |
| 22.0 | 4.1 | 262 | 17 |
| 23.2 | 3.8 | 189 | 12 |
| 24.5 | 3.6 | 141 | 9 |
| 26.1 | 3.4 | 186 | 12 |
| 26.5 | 3.4 | 195 | 13 |
| 27.3 | 3.3 | 421 | 28 |
| 27.5 | 3.2 | 257 | 17 |
| 28.2 | 3.2 | 115 | 8 |
| 29.1 | 3.1 | 630 | 41 |
| 30.3 | 3.0 | 228 | 15 |
| 30.7 | 2.9 | 162 | 11 |
| 31.7 | 2.8 | 328 | 22 |
| 32.0 | 2.8 | 105 | 7 |
| 33.0 | 2.7 | 100 | 7 |
| 34.6 | 2.6 | 92 | 6 |

Crystalline Form G

FIG. 1g shows the PXRD pattern of crystalline form G. Table 14 shows the peak list for crystalline form G. The uncertainty in the 2θ values is ±0.2° in 2θ; rel. I is the relative intensity of the respective peaks. Maximum relative intensity is 100.

TABLE 14

| 2θ | d value Å | Intensity Cps | rel. I % |
|---|---|---|---|
| 13.3 | 6.6 | 151 | 16 |
| 14.2 | 6.2 | 138 | 15 |
| 18.6 | 4.8 | 131 | 14 |
| 21.4 | 4.2 | 637 | 67 |
| 21.8 | 4.1 | 215 | 23 |
| 24.5 | 3.6 | 299 | 31 |
| 25.2 | 3.5 | 235 | 25 |
| 26.2 | 3.4 | 119 | 12 |
| 26.8 | 3.3 | 955 | 100 |
| 27.4 | 3.3 | 60 | 6 |
| 28.6 | 3.1 | 140 | 15 |
| 30.0 | 3.0 | 215 | 23 |
| 30.5 | 2.9 | 274 | 29 |
| 31.3 | 2.9 | 181 | 19 |
| 31.8 | 2.8 | 244 | 26 |
| 33.0 | 2.7 | 271 | 28 |
| 34.2 | 2.6 | 57 | 6 |
| 34.8 | 2.6 | 93 | 10 |

Analysis—FT Raman Spectroscopy (Fourier-Transform Raman Spectroscopy)

FT Raman spectra were recorded on a Bruker RFS100 Raman spectrometer (Nd-YAG 100 mW laser, excitation 1064 nm, laser power 100 mW, Ge detector, 64 scans, 25-3500 cm$^{-1}$, resolution 2 cm$^{-1}$).

Figure 2C:
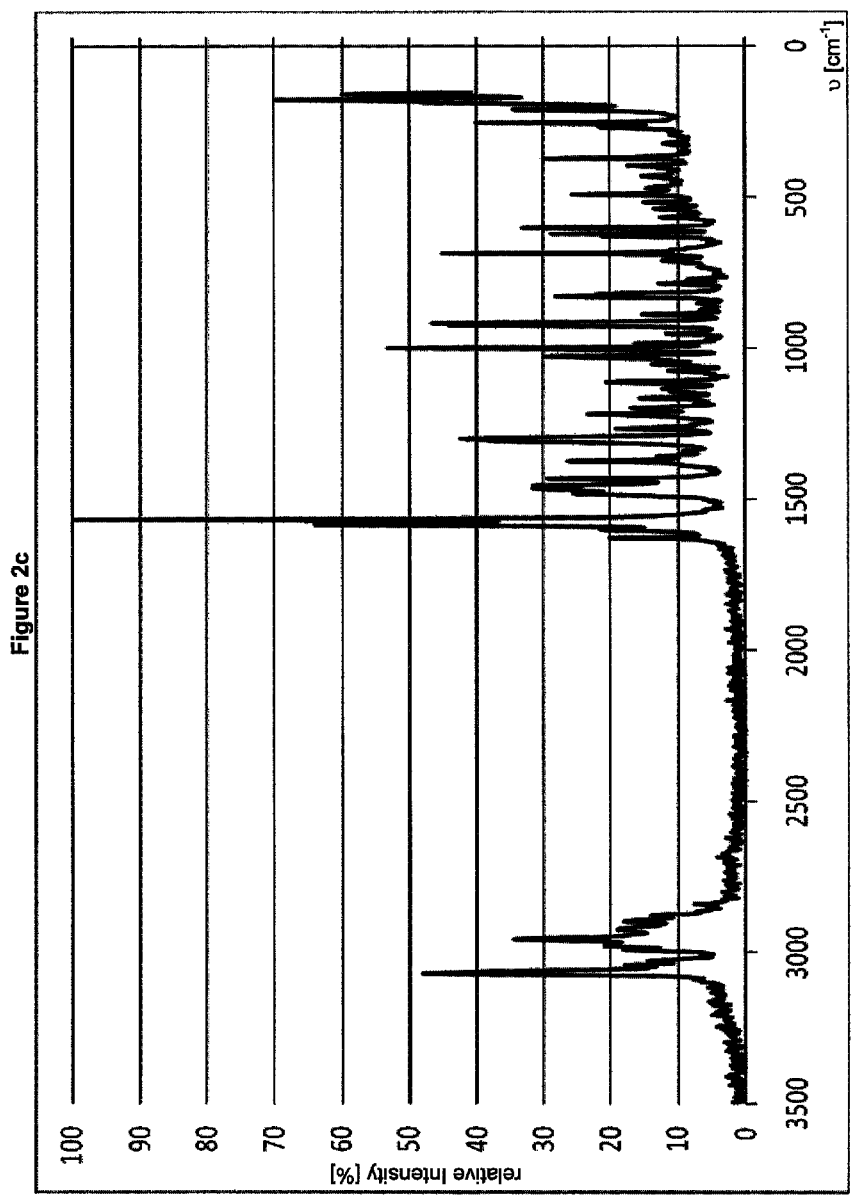
Figure 2G:
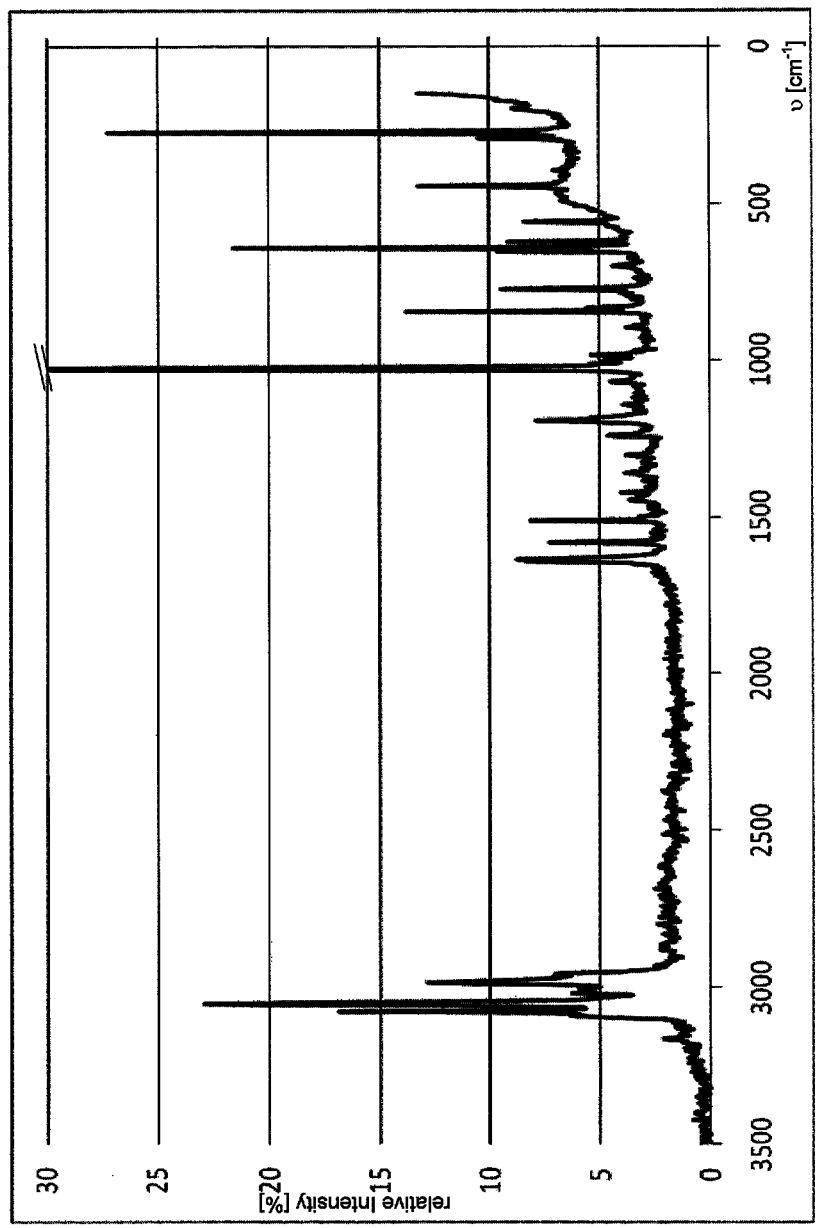

FIG. 2a shows the Raman spectra of crystalline form A.
FIG. 2b shows the Raman spectra of crystalline form B.
FIG. 2c shows the Raman spectra of crystalline form C.
FIG. 2d shows the Raman spectra of crystalline form D.
FIG. 2e shows the Raman spectra of crystalline form E.
FIG. 2f shows the Raman spectra of crystalline form F.
FIG. 2g shows the Raman spectra of crystalline form G.

Raman peak tables were generated using the software OPUS, version 3.1, build: 3, 0, 17 (20010216). The sensitivity of the peak picking function was chosen in a way that most of the peaks were found (typically between 0.5% to 3%). Features which were accidentally attributed to peaks and which were obviously noise, were removed by hand. Peaks are listed in a spectral region between 3200 cm$^{-1}$ and 150 cm$^{-1}$. For the intensity classification, the absolute intensity was used and the most intense peak was scaled to 100%. The classification is as follow: very strong (vs): I>80%; strong (s): 80%≥I>60%; medium (m): 60%≥I>40%; weak (w): 40%≥I>20%; and very weak (vw): 20%≥I.

Crystalline Form A 3201 (vw); 3071 (m); 3041 (w); 3020 (vw); 2986 (w); 2958 (s); 2935 (w); 2907 (w); 2882 (w); 2858 (vw); 2847 (vw); 2811 (vw); 2542 (vw); 1625 (vw); 1600 (vw); 1582 (w); 1554 (vs); 1470 (w); 1441 (w); 1372 (w); 1353 (vw); 1316 (w); 1295 (w); 1268 (vw); 1234 (vw); 1208 (vw); 1201 (vw); 1175 (vw); 1156 (w); 1128 (vw); 1112 (vw); 1095 (vw); 1061 (vw); 1049 (vw); 1034 (w); 1003 (m); 965 (vw); 926 (w); 914 (w); 885 (vw); 869 (vw); 842 (vw); 824 (vw); 789 (vw); 712 (vw); 691 (w); 660 (vw); 642 (vw); 621 (vw); 597 (vw); 554 (vw); 536 (vw); 524 (vw); 512 (vw); 483 (vw); 451 (vw); 408 (vw).

Crystalline Form B 3069 (m); 3054 (m); 3034 (w); 2992 (s); 2958 (w); 2931 (w); 2922 (w); 2906 (w); 2870 (w); 2845 (vw); 1628 (vw); 1583 (s); 1569 (vs); 1481 (vw); 1463 (vw); 1436 (vw); 1374 (w); 1352 (vw); 1300 (s); 1265 (vw); 1222 (vw); 1216 (vw); 1199 (vw); 1174 (vw); 1136 (vw); 1120 (vw); 1073 (vw); 1047 (vw); 1035 (vw); 1028 (vw); 1001 (m); 984 (vw); 957 (vw); 928 (vw); 919 (vw); 888 (vw); 873 (vw); 856 (vw); 828 (vw); 820 (vw); 808 (vw); 786 (vw); 768 (vw); 710 (vw); 683 (w); 628 (vw); 620 (vw); 606 (vw); 598 (vw); 568 (vw); 557 (vw); 540 (vw); 518 (vw); 491 (w); 466 (vw); 450 (vw); 430 (vw); 397 (vw); 371 (vw); 279 (vw); 255 (vw); 208 (w); 183 (m); 160 (w).

Crystalline Form C 3072 (m); 3045 (vw); 3031 (vw); 2994 (vw); 2959 (w); 2927 (vw); 2901 (vw); 2880 (vw); 2842 (vw); 1628 (vw); 1600 (w); 1584 (s); 1567 (vs); 1481 (w); 1464 (w); 1454 (w); 1432 (w); 1374 (w); 1359 (vw); 1301 (m); 1267 (vw); 1219 (w); 1200 (vw); 1167 (vw); 1136 (vw); 1114 (w); 1076 (vw); 1055 (vw); 1028 (w); 1000 (m); 986 (vw); 954 (vw); 925 (m); 918 (m); 889 (vw); 829 (w); 786 (vw); 772 (vw); 710 (vw); 685 (m); 628 (w); 620 (w); 600 (w); 567 (vw); 538 (vw); 516 (vw); 490 (w); 471 (vw); 429 (vw); 395 (vw); 370 (w); 322 (vw); 266 (w); 253 (w); 208 (w); 177 (s); 158 (m).

Crystalline Form D 3071 (vs); 3038 (w); 2981 (s); 2957 (vs); 2912 (s); 2875 (m); 2845 (w); 1627 (w); 1573 (vs); 1567 (vs); 1466 (m); 1443 (m); 1374 (m); 1355 (w); 1339 (vw); 1308 (m); 1299 (s); 1263 (w); 1250 (vw); 1217 (w); 1197 (w); 1183 (vw); 1161 (w); 1134 (vw); 1116 (w); 1074 (vw); 1045 (w); 1035 (w); 1028 (w); 1004 (s); 983 (w); 953 (vw); 919 (s); 887 (w); 869 (vw); 829 (m); 787 (vw); 771 (vw); 712 (vw); 686 (s); 676 (w); 629 (w); 620 (w); 600 (m); 569 (vw); 557 (vw); 538 (vw); 517 (w); 490 (w); 468 (vw); 429 (w); 401 (vw); 392 (w); 370 (w); 317 (vw); 278 (w); 252 (m); 206 (m); 180 (vs); 172 (vs); 161 (vs).

Crystalline Form E 3069 (vs); 3048 (w); 3031 (vw); 2986 (w); 2963 (s); 2889 (w); 2873 (w); 2855 (w); 1630 (vw); 1582 (m); 1569 (vs); 1494 (vw); 1465 (w); 1441 (w); 1376 (w); 1353 (vw); 1308 (m); 1299 (m); 1267 (vw); 1220 (w); 1200 (w); 1166 (vw); 1142 (vw); 1133 (vw); 1117 (vw); 1107 (vw); 1076 (vw); 1047 (vw); 1029 (w); 1019 (vw); 1003 (m); 993 (vw); 983 (vw); 952 (vw); 917 (m); 889 (vw); 870 (vw); 854 (vw); 836 (m); 786 (vw); 713 (vw); 686 (m); 676 (vw); 629 (vw); 619 (vw); 599 (w); 568 (vw); 558 (vw); 538 (vw); 517 (vw); 491 (w); 471 (vw); 433 (vw); 395 (vw); 369 (vw); 317 (vw); 287 (vw); 253 (w); 211 (w); 176 (m); 160 (m).

Crystalline Form F 3070 (vs), 3029 (w), 2979 (s), 2954 (m), 2942 (w), 2895 (w), 2840 (vw), 1629 (vw), 1585 (vs), 1573 (s), 1486 (vw), 1468 (w), 1458 (w), 1434 (w), 1368 (vw), 1295 (s), 1264 (vw), 1217 (w), 1201 (vw), 1170 (vw), 1132 (vw), 1110 (w), 1047 (vw), 1030 (w), 1003 (m), 980 (vw), 917 (m), 888 (vw), 829 (vw), 786 (vw), 769 (vw), 707 (vw), 683 (w), 620 (vw), 598 (w), 568 (vw), 538 (vw), 515 (vw), 488 (vw), 436 (vw), 390 (vw), 367 (vw), 273 (vw), 254 (w), 206 (m), 174 (m), 160 (s).

Crystalline Form G 3164 (vw); 3089 (vw); 3077 (vw); 3053 (w); 3019 (vw); 3006 (vw); 2986 (vw); 1636 (vw); 1582 (vw); 1512 (vw); 1446 (vw); 1422 (vw); 1361 (vw); 1304 (vw); 1242 (vw); 1193 (vw); 1146 (vw); 1070 (vw); 1028 (vs); 1005 (vw); 986 (vw); 894 (vw); 846 (vw); 835 (vw); 774 (vw); 700 (vw); 654 (vw); 642 (vw); 623 (vw); 560 (vw); 445 (vw); 293 (vw); 274 (w); 200 (vw).

Analysis—DSC

Differential Scanning Calorimetry (DSC): device reference Perkin Elmer DSC 7. Unless otherwise specified, the samples were weighed in a sealed gold crucible. The measurement took place in a nitrogen flow in a temperature range from −50° C. up to 350° C. with a heating rate of 10° C./min. The temperatures specified in relation to DSC analyses are, unless otherwise specified, the temperatures of the peak maxima.

In the following tables, "ΔH" means "specific heat", and "peak" means that a thermal event was observed at the temperature with the given peak temperature.

TABLE 15

| | DSC |
|---|---|
| Crystalline form A | broad event: 239° C., ΔH = 32 J/g<br>peak, 263° C., ΔH = 188 J/g |
| Crystalline form B | event (broad), >210° C., ΔH = −51 J/g, overlapping with:<br>peak, 266° C., ΔH = 153 J/g |

Analysis—TG-FTIR

Thermogravimetric analysis coupled with Fourier transform infrared spectra (TG-FTIR) were recorded with a Netzsch Thermo-Microwaage TG 209 and a Bruker FT-IR spectrometer Vector 22 (aluminium crucible (open or with micro-aperture), nitrogen atmosphere, heating rate 10° C./min, 25 up to 350° C.).

TG-FTIR analyses performed with a sample of crystalline form A showed no significant weight loss (−0.06%) within the temperature range from 50° C. to 250° C. indicating that crystalline form A does not contain any enclosed solvent (i.e. is an ansolvate).

TG-FTIR analyses performed with a sample of crystalline form B showed a weight loss of about 0.5% within the temperature range from RT to 250° C. The weight loss is attributable to water. Decomposition was observed above 270° C. Based on these measurements crystalline form B is an ansolvate.

TG-FTIR analyses performed with a sample of crystalline form C showed a weight loss of 24.7%. The weight loss was strongest at around 115° C. and attributable to water (heptahydrate: 23.3%; octahydrate: 25.8%). Decomposition was observed above 270° C. Based on these measurements crystalline form C is a hydrate.

TG-FTIR analyses performed with samples of crystalline form D showed a weight loss of 1.1-1.4% within the temperature range from RT to 240° C. The weight loss is attributable to water. Decomposition was observed above 270° C. Based on these measurements crystalline form D is an ansolvate.

TG-FTIR analyses performed with a sample of crystalline form E showed a weight loss of 15.1% within the temperature range from RT to 200° C. The weight loss is strongest at 110° C. and is attributable to dioxane (monosolvate: 17.5%). Decomposition was observed above 270° C.

TG-FTIR analyses performed with a sample of crystalline form F showed a weight loss of about 0.2% within the temperature range from RT to 250° C. The weight loss is attributable to water. Decomposition was observed above 270° C. Based on these measurements crystalline form F is an ansolvate.

TG-FTIR analyses performed with a sample of crystalline form G showed a weight loss of 7.4% within the temperature range from 70° C. to 200° C. The weight loss is strongest at around 170° C. and is attributable to water. A sharp, stepwise weight loss of 45.2% was observed at around 280° C. and is attributable to pyridine. This step is well above the boiling point of pyridine (115° C.) indicating that the pyridine is strongly bound. No decomposition is observed up to 350° C.

Analysis—Dynamic Vapour Sorption (DVS)

Crystalline forms A and B were characterized by dynamic vapour sorption (DVS) using a Projekt Messtechnik SPS 11-100 n multi sample vapour sorption analyzer. For the DVS analysis, each sample was placed in a AI crucible and allowed to equilibrate at 50% r.h. (relative humidity) before starting a pre-defined humidity program during which the change in weight of the sample is determined.

Although hygroscopicity was measured in a slightly different manner, it was classified according to the European Pharmacopoeia as follows: very hygroscopic (vh): increase of the mass ≥15%; hygroscopic (h): increase of the mass is less than 15% and equal or greater than 2%; slightly hygroscopic (sh): increase of the mass is less than 2% and equal or greater than 0.2%; not hygroscopic (nh): increase of the mass is less than 0.2%; deliquescent (d): sufficient water is absorbed to form a liquid.

Crystalline Form A

DVS with two cycles was performed on a sample of crystalline form A according to the following program: 2 h at 50% r.h.; 50% r.h.→0% r.h. (10%/h); 5 h at 0% r.h.; 0→95% r.h. (5%/h); 3 h at 95% r.h.; 95→50% (10%/h), and 2 h at 50% r.h.

The DVS showed two reversible cycles with no significant mass changes (Δm<0.2%).

Another sample of crystalline form A was stored at RT and 85% r.h. for 24 h for hygroscopicity testing. The sample was found to be not hygroscopic (Δm=0%).

Crystalline Form B

DVS was performed on a sample of crystalline form B according to the following program: 2 h at 50% r.h.; 50% r.h.→0% r.h. (2.5%/h); 10 h at 0% r.h.; 0→95% r.h. (2.5%/h); 10 h at 95% r.h.; 95→50% (2.5%/h), and 2 h at 50% r.h.

The sample showed a strong (and stepwise) water uptake above 74% r.h (up to a water content of approx. 15.4%). Lowering the humidity led to a complete loss of water, which was completed at about 50% r.h., i.e. a hysteresis was observed, indicating hydrate formation.

To further elucidate this, a suspension equilibration experiment of crystalline form B in water was performed.

A sample of crystalline form B was suspended for several days in water at RT and a Raman spectrum was measured in the wet state. Surprisingly no conversion of crystalline form B was observed.

In two control experiments, crystalline form B was stored for more than 2 weeks at 75.5% r.h. at RT and at 97% r.h. at RT, respectively, and the samples were analyzed by FT-Raman spectroscopy. No conversion was observed. Consequently, the DVS measurement was repeated. The data were in agreement with the first DVS experiment. The sample was checked before and after the DVS measurement by FT-Raman spectroscopy. No conversion was observed.

Hence an experiment was performed where a sample of crystalline form B was stored for about 3 weeks at 97% r.h. at RT and FT-Raman and TGFT-IR measurements were performed at the same time. FT-Raman showed no conversion, whereas TG-FTIR showed a water content of about 19% water and about 3% DMSO (the DMSO comes from the initial preparation of the sample). These results show that crystalline form B indeed takes up water above 75% r.h., but that this water uptake is not detectable by means of Raman spectroscopy.

Analysis—Solubility in Water

The aqueous solubility was determined in bidest $H_2O$ from saturated solutions (24 h equilibration time, RT). The concentration was measured by HPLC and the pH of the saturated solutions was determined.

TABLE 16

| | solubility [mg/L] | resulting pH |
|---|---|---|
| free base | <0.30 | 8.4 |
| hydrochloride | 1.21 | 2.7 |

It becomes evident from the solubility data that formation of the hydrochloride salt improves the aqueous solubility of the compound.

Analysis—Physical and Chemical Stability

In this experiment the physical and chemical stability of (1r,4r)-6'-fluoro-N,N-dimethyl-4-phenyl-4',9'-dihydro-3'H-spiro[cyclohexane-1,1'-pyrano[3,4,b]indol]-4-amine hydrochloride (in the form of crystalline form A) was compared to that of the free base.

The stability tests were performed under two conditions. The samples were stored for four weeks at 75% r.h. at 40° C. in open vials and one week at 80° C. in closed vials. The purity was determined by HPLC. The results are summarized in Table 17.

TABLE 17

| | Ref. Purity [area %] | 4 weeks at 40° C., 75% r.h. | | 1 week at 80° C. | |
|---|---|---|---|---|---|
| | | Purity [area %] | PXRD | Purity [area %] | PXRD |
| free base | 99.7 | 99.5 | new peaks and peak shifts | 99.7 | new peaks and peak shifts |
| hydrochloride | 100.0 | 100.0 | no change | 100.0 | no change |

The hydrochloride salt showed no significant degradation after stability testing, whereas the free base showed clearly changes.

Analysis—Single Crystal Diffraction

Measurements were realized using MoKα-radiation (λ=0.71073 Å) and a Bruker AXS D8-Goniometer equipped with a SMART APEX-CCD detector at 100K.

Crystal data of crystalline forms A and D are summarized in the following tables 18-31.

Crystalline form A

TABLE 18

Crystal data and structure refinement for crystalline form A.

| | |
|---|---|
| Empirical formula | $C_{24}H_{28}ClFN_2O$ |
| Formula weight | 414.93 |
| Temperature | 100(2) K |
| Wavelength | .71073 Å |
| Crystal system | Triclinic |
| Space group | P$\bar{1}$ |
| Unit cell dimensions | a = 9.485(2) A alpha = 75.571(6) deg. |
| | b = 10.776(2) A beta = 67.652(6) deg. |
| | c = 11.369(2) A gamma = 78.606(7) deg. |
| Volume | 1034.0(3) Å$^3$ |
| Z | 2 |
| V/Z | 517.0(2) Å$^3$ |

TABLE 18-continued

Crystal data and structure refinement for crystalline form A.

| | |
|---|---|
| Density (calculated) | 1.333 Mg/m$^3$ |
| Absorption coefficient | 0.212 mm$^{-1}$ |
| F(000) | 440 |
| Crystal size | .20 × .07 × .02 mm |
| Theta range for data collection | 2.34 to 27.07 deg. |
| Index ranges | $-12 \leq h \leq 12, -13 \leq k \leq 13,$ $-14 \leq l \leq 14$ |
| Reflections collected | 18649 |
| Independent reflections | 4409 [R(int) = 0.0922] |
| Absorption correction | None |
| Refinement method | Full-matrix least-squares on F$^2$ |
| Data/restraints/parameters | 4409/0/264 |
| Goodness-of-fit on F$^2$ | 1.066 |
| Final R indices [I > 2sigma(I)] | R1 = 0.0715, wR2 = 0.1693 |
| R indices (all data) | R1 = 0.1021, wR2 = 0.1856 |
| Largest diff. peak and hole | .810 and −.384 e × Å$^{-3}$ |
| Filled space | 69.9% |

TABLE 19

Atomic coordinates (×10$^4$) (i.e. (×10$^\wedge$4)) and equivalent isotropic displacement parameters ($^2$×10$^3$) (i.e. ($^\wedge$2 × 10$^\wedge$3)) for crystalline form A. U(eq) is defined as one third of the trace of the orthogonalized Uij tensor.

| | x | y | z | U(eq) |
|---|---|---|---|---|
| F(1) | 3095(2) | 10783(2) | −3774(2) | 27(1) |
| O(1) | 3966(2) | 3410(2) | −2026(2) | 18(1) |
| N(1) | 2372(3) | 6215(2) | −366(2) | 14(1) |
| N(2) | 1248(3) | 3254(3) | 3385(3) | 16(1) |
| C(1) | 2867(4) | 9645(3) | −2888(3) | 20(1) |
| C(2) | 3302(4) | 8523(3) | −3339(3) | 18(1) |
| C(3) | 3094(3) | 7372(3) | −2407(3) | 16(1) |
| C(4) | 2441(3) | 7459(3) | −1082(3) | 15(1) |
| C(5) | 2953(3) | 5361(3) | −1211(3) | 14(1) |
| C(6) | 3148(3) | 3903(3) | −848(3) | 14(1) |
| C(7) | 3484(4) | 4031(3) | −3095(3) | 18(1) |
| C(8) | 3982(4) | 5374(3) | −3592(3) | 18(1) |
| C(9) | 3387(3) | 6031(3) | −2461(3) | 15(1) |
| C(10) | 1648(3) | 3302(3) | −133(3) | 15(1) |
| C(11) | 910(3) | 3444(3) | 1279(3) | 14(1) |
| C(12) | 2000(3) | 2851(3) | 2042(3) | 14(1) |
| C(13) | 2243(4) | 2905(4) | 4192(3) | 26(1) |
| C(14) | −279(4) | 2814(3) | 4177(3) | 23(1) |
| C(15) | 3485(3) | 3509(3) | 1350(3) | 14(1) |
| C(16) | 4214(3) | 3393(3) | −63(3) | 16(1) |
| C(17) | 2273(3) | 1380(3) | 2235(3) | 15(1) |
| C(22) | 1112(4) | 658(3) | 2404(3) | 17(1) |
| C(21) | 1350(4) | −672(3) | 2589(3) | 19(1) |
| C(20) | 2767(4) | −1324(3) | 2584(3) | 20(1) |
| C(19) | 3936(4) | −624(3) | 2415(3) | 22(1) |
| C(18) | 3682(4) | 704(3) | 2252(3) | 20(1) |
| C(23) | 1989(4) | 8624(3) | −658(3) | 19(1) |
| C(24) | 2199(4) | 9738(3) | −1584(3) | 19(1) |
| Cl(1) | 692(1) | 6169(1) | 2716(1) | 19(1) |

TABLE 20A

| bond lengths [Å] and angles [deg] | | bond lengths [Å] and angles [deg] |
|---|---|---|
| Bond lengths [Å] and angles [deg] for crystalline form A. | | |
| F(1)—C(1) | 1.375(4) | |
| O(1)—C(7) | 1.424(4) | |
| O(1)—C(6) | 1.442(3) | |
| N(1)—C(5) | 1.382(4) | |
| N(1)—C(4) | 1.383(4) | |
| N(1)—H(1) | .8800 | |
| N(2)—C(14) | 1.483(4) | |
| N(2)—C(13) | 1.491(4) | |
| N(2)—C(12) | 1.551(4) | |
| C(11)—C(12) | 1.541(4) | |
| C(11)—H(11A) | .9900 | |
| C(11)—H(11B) | .9900 | |
| C(12)—C(17) | 1.528(4) | |
| C(12)—C(15) | 1.542(4) | |
| C(13)—H(13A) | .9800 | |
| C(13)—H(13B) | .9800 | |
| C(13)—H(13C) | .9800 | |
| C(14)—H(14A) | .9800 | |

TABLE 20A-continued

| | bond lengths [Å] and angles [deg] | | bond lengths [Å] and angles [deg] |
|---|---|---|---|
| N(2)—H(2) | .9300 | C(14)—H(14B) | .9800 |
| C(1)—C(2) | 1.358(5) | C(14)—H(14C) | .9800 |
| C(1)—C(24) | 1.395(5) | C(15)—C(16) | 1.516(4) |
| C(2)—C(3) | 1.409(4) | C(15)—H(15A) | .9900 |
| C(2)—H(2A) | .9500 | C(15)—H(15B) | .9900 |
| C(3)—C(4) | 1.414(4) | C(16)—H(16A) | .9900 |
| C(3)—C(9) | 1.429(4) | C(16)—H(16B) | .9900 |
| C(4)—C(23) | 1.387(4) | C(17)—C(18) | 1.395(4) |
| C(5)—C(9) | 1.368(4) | C(17)—C(22) | 1.400(4) |
| C(5)—C(6) | 1.514(4) | C(22)—C(21) | 1.381(4) |
| C(6)—C(10) | 1.526(4) | C(22)—H(22) | .9500 |
| C(6)—C(16) | 1.530(4) | C(21)—C(20) | 1.387(5) |
| C(7)—C(8) | 1.515(4) | C(21)—H(21) | .9500 |
| C(7)—H(7A) | .9900 | C(20)—C(19) | 1.389(5) |
| C(7)—H(7B) | .9900 | C(20)—H(20) | .9500 |
| C(8)—C(9) | 1.488(4) | C(19)—C(18) | 1.381(5) |
| C(8)—H(8A) | .9900 | C(19)—H(19) | .9500 |
| C(8)—H(8B) | .9900 | C(18)—H(18) | .9500 |
| C(10)—C(11) | 1.522(4) | C(23)—C(24) | 1.376(5) |
| C(10)—H(10A) | .9900 | C(23)—H(23) | .9500 |
| C(10)—H(10B) | .9900 | C(24)—H(24) | .9500 |

Table 20B: (Table 20A continued) Bond lengths [Å] and angles [deg] for crystalline form A.

| | | | |
|---|---|---|---|
| C(7)—O(1)—C(6) | 115.4(2) | C(12)—C(11)—H(11B) | 109.3 |
| C(5)—N(1)—C(4) | 108.6(3) | H(11A)—C(11)—H(11B) | 107.9 |
| C(5)—N(1)—H(1) | 125.7 | C(17)—C(12)—C(11) | 112.7(2) |
| C(4)—N(1)—H(1) | 125.7 | C(17)—C(12)—C(15) | 113.7(2) |
| C(14)—N(2)—C(13) | 108.9(3) | C(11)—C(12)—C(15) | 107.7(2) |
| C(14)—N(2)—C(12) | 115.2(2) | C(17)—C(12)—N(2) | 109.2(2) |
| C(13)—N(2)—C(12) | 114.3(2) | C(11)—C(12)—N(2) | 107.1(2) |
| C(14)—N(2)—H(2) | 105.9 | C(15)—C(12)—N(2) | 106.1(2) |
| C(13)—N(2)—H(2) | 105.9 | N(2)—C(13)—H(13A) | 109.5 |
| C(12)—N(2)—H(2) | 105.9 | N(2)—C(13)—H(13B) | 109.5 |
| C(2)—C(1)—F(1) | 118.2(3) | H(13A)—C(13)—H(13B) | 109.5 |
| C(2)—C(1)—C(24) | 125.0(3) | N(2)—C(13)—H(13C) | 109.5 |
| F(1)—C(1)—C(24) | 116.8(3) | H(13A)—C(13)—H(13C) | 109.5 |
| C(1)—C(2)—C(3) | 116.9(3) | H(13B)—C(13)—H(13C) | 109.5 |
| C(1)—C(2)—H(2A) | 121.6 | N(2)—C(14)—H(14A) | 109.5 |
| C(3)—C(2)—H(2A) | 121.6 | N(2)—C(14)—H(14B) | 109.5 |
| C(2)—C(3)—C(4) | 118.4(3) | H(14A)—C(14)—H(14B) | 109.5 |
| C(2)—C(3)—C(9) | 134.7(3) | N(2)—C(14)—H(14C) | 109.5 |
| C(4)—C(3)—C(9) | 106.9(3) | H(14A)—C(14)—H(14C) | 109.5 |
| N(1)—C(4)—C(23) | 129.3(3) | H(14B)—C(14)—H(14C) | 109.5 |
| N(1)—C(4)—C(3) | 107.6(3) | C(16)—C(15)—C(12) | 112.3(2) |
| C(23)—C(4)—C(3) | 123.1(3) | C(16)—C(15)—H(15A) | 109.2 |
| C(9)—C(5)—N(1) | 109.7(3) | C(12)—C(15)—H(15A) | 109.2 |
| C(9)—C(5)—C(6) | 123.7(3) | C(16)—C(15)—H(15B) | 109.2 |
| N(1)—C(5)—C(6) | 126.6(3) | C(12)—C(15)—H(15B) | 109.2 |
| O(1)—C(6)—C(5) | 107.7(2) | H(15A)—C(15)—H(15B) | 107.9 |
| O(1)—C(6)—C(10) | 109.2(2) | C(15)—C(16)—C(6) | 114.4(2) |
| C(5)—C(6)—C(10) | 114.5(2) | C(15)—C(16)—H(16A) | 108.7 |
| O(1)—C(6)—C(16) | 103.0(2) | C(6)—C(16)—H(16A) | 108.7 |
| C(5)—C(6)—C(16) | 112.9(3) | C(15)—C(16)—H(16B) | 108.7 |
| C(10)—C(6)—C(16) | 108.9(2) | C(6)—C(16)—H(16B) | 108.7 |
| O(1)—C(7)—C(8) | 109.5(3) | H(16A)—C(16)—H(16B) | 107.6 |
| O(1)—C(7)—H(7A) | 109.8 | C(18)—C(17)—C(22) | 117.4(3) |
| C(8)—C(7)—H(7A) | 109.8 | C(18)—C(17)—C(12) | 121.5(3) |
| O(1)—C(7)—H(7B) | 109.8 | C(22)—C(17)—C(12) | 121.1(3) |
| C(8)—C(7)—H(7B) | 109.8 | C(21)—C(22)—C(17) | 121.3(3) |
| H(7A)—C(7)—H(7B) | 108.2 | C(21)—C(22)—H(22) | 119.4 |
| C(9)—C(8)—C(7) | 106.8(3) | C(17)—C(22)—H(22) | 119.4 |
| C(9)—C(8)—H(8A) | 110.4 | C(22)—C(21)—C(20) | 120.4(3) |
| C(7)—C(8)—H(8A) | 110.4 | C(22)—C(21)—H(21) | 119.8 |
| C(9)—C(8)—H(8B) | 110.4 | C(20)—C(21)—H(21) | 119.8 |
| C(7)—C(8)—H(8B) | 110.4 | C(21)—C(20)—C(19) | 119.2(3) |
| H(8A)—C(8)—H(8B) | 108.6 | C(21)—C(20)—H(20) | 120.4 |
| C(5)—C(9)—C(3) | 107.2(3) | C(19)—C(20)—H(20) | 120.4 |
| C(5)—C(9)—C(8) | 122.2(3) | C(18)—C(19)—C(20) | 120.1(3) |
| C(3)—C(9)—C(8) | 130.5(3) | C(18)—C(19)—H(19) | 119.9 |
| C(11)—C(10)—C(6) | 113.7(2) | C(20)—C(19)—H(19) | 119.9 |
| C(11)—C(10)—H(10A) | 108.8 | C(19)—C(18)—C(17) | 121.6(3) |
| C(6)—C(10)—H(10A) | 108.8 | C(19)—C(18)—H(18) | 119.2 |
| C(11)—C(10)—H(10B) | 108.8 | C(17)—C(18)—H(18) | 119.2 |
| C(6)—C(10)—H(10B) | 108.8 | C(24)—C(23)—C(4) | 117.6(3) |
| H(10A)—C(10)—H(10B) | 107.7 | C(24)—C(23)—H(23) | 121.2 |
| C(10)—C(11)—C(12) | 111.7(2) | C(4)—C(23)—H(23) | 121.2 |

TABLE 20A-continued

| bond lengths [Å] and angles [deg] | | bond lengths [Å] and angles [deg] | |
|---|---|---|---|
| C(10)—C(11)—H(11A) | 109.3 | C(23)—C(24)—C(1) | 119.0(3) |
| C(12)—C(11)—H(11A) | 109.3 | C(23)—C(24)—H(24) | 120.5 |
| C(10)—C(11)—H(11B) | 109.3 | C(1)—C(24)—H(24) | 120.5 |

TABLE 21

Hydrogen coordinates ($\times 10^4$) (i.e. ($\times 10^{\char`^}4$)) and isotropic displacement parameters ($^2 \times 10^3$) (i.e. ($^{\char`^}2 \times 10^{\char`^}3$)) for crystalline form A.

| | x | y | z | U(eq) |
|---|---|---|---|---|
| H(1) | 2017 | 6003 | 485 | 17 |
| H(2) | 1085 | 4151 | 3215 | 20 |
| H(2A) | 3728 | 8515 | −4241 | 21 |
| H(7A) | 2354 | 4086 | −2820 | 22 |
| H(7B) | 3945 | 3524 | −3794 | 22 |
| H(8A) | 5115 | 5327 | −3969 | 22 |
| H(8B) | 3554 | 5854 | −4268 | 22 |
| H(10A) | 915 | 3709 | −585 | 18 |
| H(10B) | 1848 | 2373 | −170 | 18 |
| H(11A) | −39 | 3015 | 1686 | 17 |
| H(11B) | 622 | 4371 | 1322 | 17 |
| H(13A) | 1674 | 3156 | 5035 | 40 |
| H(13B) | 3160 | 3357 | 3752 | 40 |
| H(13C) | 2548 | 1971 | 4321 | 40 |
| H(14A) | −164 | 1874 | 4452 | 35 |
| H(14B) | −950 | 3061 | 3661 | 35 |
| H(14C) | −732 | 3217 | 4943 | 35 |
| H(15A) | 3247 | 4433 | 1409 | 17 |
| H(15B) | 4226 | 3111 | 1797 | 17 |
| H(16A) | 4571 | 2474 | −112 | 20 |
| H(16B) | 5126 | 3870 | −467 | 20 |
| H(22) | 141 | 1090 | 2392 | 20 |
| H(21) | 539 | −1143 | 2719 | 23 |
| H(20) | 2937 | −2238 | 2696 | 24 |
| H(19) | 4911 | −1060 | 2411 | 26 |
| H(18) | 4488 | 1169 | 2148 | 24 |
| H(23) | 1551 | 8652 | 239 | 22 |
| H(24) | 1892 | 10557 | −1338 | 23 |

TABLE 22

Anisotropic displacement parameters ($^2 \times 10^3$) (i.e. ($^{\char`^}2 \times 10^{\char`^}3$)) for crystalline form A. The anisotropic displacement factor exponent takes the form: $-2\pi^2 [h^2 a^{*2} U_{11} + \ldots + 2 h k a^* b^* U_{12}]$.

| | U11 | U22 | U33 | U23 | U13 | U12 |
|---|---|---|---|---|---|---|
| F(1) | 35(1) | 18(1) | 24(1) | 5(1) | −8(1) | −7(1) |
| O(1) | 15(1) | 19(1) | 15(1) | −5(1) | 0(1) | 0(1) |
| N(1) | 12(1) | 14(1) | 12(1) | −2(1) | 1(1) | −4(1) |
| N(2) | 14(1) | 18(1) | 14(1) | −4(1) | −2(1) | −3(1) |
| C(1) | 15(2) | 19(2) | 22(2) | 4(1) | −8(1) | −4(1) |
| C(2) | 14(2) | 23(2) | 15(2) | −2(1) | −5(1) | −3(1) |
| C(3) | 7(1) | 21(2) | 16(2) | −3(1) | 0(1) | −5(1) |
| C(4) | 10(1) | 20(2) | 14(2) | −1(1) | −2(1) | −6(1) |
| C(5) | 10(1) | 16(2) | 16(2) | −5(1) | −2(1) | −3(1) |
| C(6) | 13(2) | 15(2) | 12(2) | −5(1) | 1(1) | −4(1) |
| C(7) | 19(2) | 21(2) | 14(2) | −7(1) | −1(1) | −4(1) |
| C(8) | 15(2) | 22(2) | 15(2) | −6(1) | −1(1) | −2(1) |
| C(9) | 10(1) | 18(2) | 17(2) | −4(1) | −3(1) | −2(1) |
| C(10) | 11(2) | 19(2) | 15(2) | −5(1) | −3(1) | −3(1) |
| C(11) | 11(1) | 16(2) | 13(2) | −2(1) | 0(1) | −5(1) |
| C(12) | 12(2) | 15(2) | 13(2) | −5(1) | 1(1) | −3(1) |
| C(13) | 26(2) | 36(2) | 18(2) | −8(2) | −9(2) | −2(2) |
| C(14) | 20(2) | 29(2) | 16(2) | −8(1) | 6(1) | −12(1) |
| C(15) | 11(1) | 15(2) | 14(2) | −2(1) | −2(1) | −4(1) |
| C(16) | 8(1) | 18(2) | 18(2) | −1(1) | 0(1) | −4(1) |
| C(17) | 15(2) | 19(2) | 10(2) | −3(1) | −4(1) | −2(1) |
| C(22) | 14(2) | 18(2) | 18(2) | −4(1) | −4(1) | −2(1) |
| C(21) | 19(2) | 19(2) | 18(2) | −4(1) | −2(1) | −7(1) |
| C(20) | 21(2) | 13(2) | 21(2) | −1(1) | −3(1) | −3(1) |
| C(19) | 16(2) | 17(2) | 31(2) | −6(1) | −6(1) | 0(1) |
| C(18) | 16(2) | 20(2) | 22(2) | −3(1) | −6(1) | −3(1) |
| C(23) | 15(2) | 22(2) | 19(2) | −7(1) | −4(1) | −4(1) |
| C(24) | 16(2) | 16(2) | 26(2) | −5(1) | −7(1) | −2(1) |
| Cl(1) | 21(1) | 16(1) | 16(1) | −5(1) | 0(1) | −5(1) |

TABLE 23

Conformation of crystalline form A.

| bond | distance | angle with plane normal | orientation |
|---|---|---|---|
| C(6)—O(1) | 1.442(4) | 56.69(19) | Bi |
| C(6)—C(5) | 1.514(5) | 15.7(2) | Ax |
| C(12)—N(2) | 1.552(4) | 61.96(18) | Eq |
| C(12)—C(17) | 1.528(5) | 8.9(2) | Ax |

TABLE 24

Geometry of hydrogen bonds of crystalline form A.

| bond | D-H | H...A | D...A | D-H...A |
|---|---|---|---|---|
| N(1)—H(1)...Cl(1) | 0.88 | 2.40 | 3.243(2) | 161 |
| N(2)—H(2)...Cl(1) | 0.93 | 2.10 | 3.030(3) | 176 |

Crystalline Form D

TABLE 25

Crystal data and structure refinement for crystalline form D.

| | |
|---|---|
| Empirical formula | $C_{24}H_{28}ClFN_2O$ |
| Formula weight | 414.93 |
| Temperature | 100(2) K |
| Wavelength | .71073 Å |
| Crystal system | Triclinic |
| Space group | $P\bar{1}$ |
| Unit cell dimensions | a = 9.8311(18) Å alpha = 82.551(6) deg. |
| | b = 11.478(2) Å beta = 82.940(5) deg. |
| | c = 18.532(4) Å gamma = 77.804(5) deg. |
| Volume | 2016.9(7) Å$^3$ |
| Z | 4 |
| V/Z | 504.2(2) Å$^3$ |
| Density (calculated) | 1.367 Mg/m$^3$ |
| Absorption coefficient | 0.217 mm$^{-1}$ |
| F(000) | 880 |
| Crystal size | 0.41 × 0.26 × 0.01 mm |
| Theta range for data collection | 1.11 to 26.00 deg. |
| Index ranges | −12 ≤ h ≤ 12, −14 ≤ k ≤ 14, −22 ≤ l ≤ 22 |
| Reflections collected | 45689 |
| Independent reflections | 7820 [R(int) = 0.2049] |

TABLE 25-continued

Crystal data and structure refinement for crystalline form D.

| | |
|---|---|
| Absorption correction | None |
| Refinement method | Full-matrix least-squares on $F^2$ |
| Data/restraints/parameters | 7820/0/528 |
| Goodness-of-fit on $F^2$ | 1.221 |
| Final R indices [I > 2sigma(I)] | R1 = 0.0882, wR2 = 0.2351 |
| R indices (all data) | R1 = 0.1378, wR2 = 0.2546 |
| Largest diff. peak and hole | 1.459 and −.412 e × Å$^{-3}$ |
| Filled space | 71.3% |

TABLE 26

Atomic coordinates (×10$^4$) (i.e. (×10^4)) and equivalent isotropic displacement parameters ($^2$×10$^3$) (i.e. (^2 × 10^3)) for crystalline form D. U(eq) is defined as one third of the trace of the orthogonalized Uij tensor.

| | x | y | z | U(eq) |
|---|---|---|---|---|
| F(1) | 8490(4) | −5596(3) | 6582(2) | 43(1) |
| O(1) | 6891(4) | 1279(3) | 6127(2) | 27(1) |
| N(1) | 5045(5) | −1239(4) | 6431(3) | 26(1) |
| N(2) | 2051(5) | 2500(4) | 6182(3) | 27(1) |
| C(1) | 7608(7) | −4517(5) | 6557(3) | 32(2) |
| C(2) | 8149(6) | −3518(6) | 6404(3) | 29(1) |
| C(3) | 7195(6) | −2407(5) | 6370(3) | 25(1) |
| C(4) | 5754(6) | −2410(5) | 6493(3) | 27(1) |
| C(5) | 6014(6) | −509(5) | 6270(3) | 26(1) |
| C(6) | 5630(6) | 822(5) | 6161(3) | 28(1) |
| C(7) | 8058(6) | 654(5) | 5693(3) | 29(1) |
| C(8) | 8564(6) | −612(5) | 6023(3) | 30(1) |
| C(9) | 7325(5) | −1180(5) | 6227(3) | 23(1) |
| C(16) | 4882(6) | 1268(5) | 5485(3) | 28(1) |
| C(15) | 4283(6) | 2604(5) | 5404(3) | 28(1) |
| C(12) | 3353(6) | 3071(5) | 6074(3) | 25(1) |
| C(13) | 1107(6) | 2896(6) | 5592(3) | 32(2) |
| C(14) | 1189(6) | 2627(6) | 6904(3) | 30(1) |
| C(11) | 4216(6) | 2649(5) | 6731(3) | 26(1) |
| C(10) | 4732(6) | 1314(5) | 6836(3) | 23(1) |
| C(17) | 2849(6) | 4429(5) | 5974(3) | 26(1) |
| C(18) | 2377(6) | 5072(5) | 6575(3) | 27(1) |

TABLE 26-continued

Atomic coordinates (×10$^4$) (i.e. (×10^4)) and equivalent isotropic displacement parameters ($^2$×10$^3$) (i.e. (^2 × 10^3)) for crystalline form D. U(eq) is defined as one third of the trace of the orthogonalized Uij tensor.

| | x | y | z | U(eq) |
|---|---|---|---|---|
| C(19) | 1906(6) | 6292(5) | 6480(3) | 30(1) |
| C(20) | 1917(6) | 6912(5) | 5793(4) | 31(2) |
| C(21) | 2390(6) | 6299(6) | 5199(4) | 32(2) |
| C(22) | 2856(6) | 5068(5) | 5285(3) | 30(1) |
| C(23) | 5283(6) | −3470(5) | 6656(3) | 30(1) |
| C(24) | 6196(6) | −4523(6) | 6689(3) | 31(1) |
| F(2) | 198(4) | 14652(5) | 2162(2) | 45(1) |
| O(2) | 2429(4) | 8182(4) | 1151(2) | 30(1) |
| N(3) | 2095(4) | 11297(4) | 286(3) | 26(1) |
| N(4) | 3568(4) | 8466(4) | −1366(2) | 23(1) |
| C(25) | 682(6) | 13826(6) | 1686(3) | 35(2) |
| C(26) | 848(6) | 12634(6) | 1928(3) | 32(2) |
| C(27) | 1346(5) | 11817(6) | 1411(3) | 26(1) |
| C(28) | 1640(6) | 12261(5) | 679(3) | 27(1) |
| C(29) | 2082(6) | 10262(5) | 747(3) | 26(1) |
| C(30) | 2486(6) | 9043(5) | 513(3) | 24(1) |
| C(31) | 1346(8) | 8440(7) | 1689(4) | 58(2) |
| C(32) | 1470(7) | 9567(6) | 2049(3) | 39(2) |
| C(33) | 1608(6) | 10553(6) | 1443(3) | 28(1) |
| C(34) | 4017(5) | 8803(5) | 176(3) | 23(1) |
| C(35) | 4432(5) | 7618(5) | −151(3) | 24(1) |
| C(36) | 3496(6) | 7448(5) | −715(3) | 24(1) |
| C(37) | 2633(6) | 8431(6) | −1937(3) | 31(1) |
| C(38) | 5006(6) | 8497(5) | −1714(3) | 27(1) |
| C(39) | 2002(6) | 7662(5) | −342(3) | 25(1) |
| C(40) | 1533(6) | 8837(5) | −21(3) | 27(1) |
| C(41) | 3941(6) | 6257(5) | −1012(3) | 24(1) |
| C(42) | 5350(6) | 5720(5) | −1144(3) | 25(1) |
| C(43) | 5733(6) | 4630(6) | −1412(3) | 31(2) |
| C(44) | 4754(7) | 4030(6) | −1563(3) | 33(2) |
| C(45) | 3365(6) | 4521(6) | −1436(3) | 30(1) |
| C(46) | 2979(6) | 5619(5) | −1176(3) | 29(1) |
| C(47) | 1452(5) | 13465(5) | 450(3) | 28(1) |
| C(48) | 957(6) | 14273(6) | 956(3) | 32(2) |
| Cl(1) | 8139(2) | 119(1) | 3698(1) | 30(1) |
| Cl(2) | 7143(2) | 8800(1) | 1398(1) | 33(1) |

TABLE 27A

Bond lengths [Å] and angles [deg] for crystalline form D.

| bond lengths [Å] and angles [deg] | | bond lengths [Å] and angles [deg] | | bond lengths [Å] and angles [deg] | |
|---|---|---|---|---|---|
| F(1)—C(1) | 1.353(6) | C(14)—H(14C) | .9800 | C(30)—C(34) | 1.539(7) |
| O(1)—C(7) | 1.433(6) | C(11)—C(10) | 1.504(8) | C(31)—C(32) | 1.564(10) |
| O(1)—C(6) | 1.437(7) | C(11)—H(11A) | .9900 | C(31)—H(31A) | .9900 |
| N(1)—C(4) | 1.375(7) | C(11)—H(11B) | .9900 | C(31)—H(31B) | .9900 |
| N(1)—C(5) | 1.379(8) | C(10)—H(10A) | .9900 | C(32)—C(33) | 1.503(9) |
| N(1)—H(1) | .8800 | C(10)—H(10B) | .9900 | C(32)—H(32A) | .9900 |
| N(2)—C(13) | 1.485(7) | C(17)—C(22) | 1.387(8) | C(32)—H(32B) | .9900 |
| N(2)—C(14) | 1.499(7) | C(17)—C(18) | 1.395(8) | C(34)—C(35) | 1.517(8) |
| N(2)—C(12) | 1.538(7) | C(18)—C(19) | 1.374(8) | C(34)—H(34A) | .9900 |
| N(2)—H(2) | .9300 | C(18)—H(18) | .9500 | C(34)—H(34B) | .9900 |
| C(1)—C(2) | 1.346(9) | C(19)—C(20) | 1.375(9) | C(35)—C(36) | 1.530(8) |
| C(1)—C(24) | 1.381(9) | C(19)—H(19) | .9500 | C(35)—H(35A) | .9900 |
| C(2)—C(3) | 1.414(8) | C(20)—C(21) | 1.364(9) | C(35)—H(35B) | .9900 |
| C(2)—H(2A) | .9500 | C(20)—H(20) | .9500 | C(36)—C(41) | 1.499(8) |
| C(3)—C(4) | 1.408(8) | C(21)—C(22) | 1.385(8) | C(36)—C(39) | 1.529(7) |
| C(3)—C(9) | 1.429(8) | C(21)—H(21) | .9500 | C(37)—H(37A) | .9800 |
| C(4)—C(23) | 1.376(9) | C(22)—H(22) | .9500 | C(37)—H(37B) | .9800 |
| C(5)—C(9) | 1.354(8) | C(23)—C(24) | 1.343(8) | C(37)—H(37C) | .9800 |
| C(5)—C(6) | 1.488(8) | C(23)—H(23) | .9500 | C(38)—H(38A) | .9800 |
| C(6)—C(16) | 1.507(8) | C(24)—H(24) | .9500 | C(38)—H(38B) | .9800 |
| C(6)—C(10) | 1.537(7) | F(2)—C(25) | 1.351(7) | C(38)—H(38C) | .9800 |
| C(7)—C(8) | 1.507(8) | O(2)—C(31) | 1.378(8) | C(39)—C(40) | 1.504(8) |
| C(7)—H(7A) | .9900 | O(2)—C(30) | 1.442(7) | C(39)—H(39A) | .9900 |
| C(7)—H(7B) | .9900 | N(3)—C(28) | 1.369(7) | C(39)—H(39B) | .9900 |
| C(8)—C(9) | 1.486(8) | N(3)—C(29) | 1.372(7) | C(40)—H(40A) | .9900 |

TABLE 27A-continued

| | | | | | |
|---|---|---|---|---|---|
| C(8)—H(8A) | .9900 | N(3)—H(3) | .8800 | C(40)—H(40B) | .9900 |
| C(8)—H(8B) | .9900 | N(4)—C(38) | 1.486(7) | C(41)—C(46) | 1.395(9) |
| C(16)—C(15) | 1.517(8) | N(4)—C(37) | 1.493(7) | C(41)—C(42) | 1.398(8) |
| C(16)—H(16A) | .9900 | N(4)—C(36) | 1.574(7) | C(42)—C(43) | 1.367(8) |
| C(16)—H(16B) | .9900 | N(4)—H(4) | .9300 | C(42)—H(42) | .9500 |
| C(15)—C(12) | 1.534(8) | C(25)—C(26) | 1.366(9) | C(43)—C(44) | 1.370(9) |
| C(15)—H(15A) | .9900 | C(25)—C(48) | 1.399(9) | C(43)—H(43) | .9500 |
| C(15)—H(15B) | .9900 | C(26)—C(27) | 1.400(8) | C(44)—C(45) | 1.367(8) |
| C(12)—C(17) | 1.527(8) | C(26)—H(26) | .9500 | C(44)—H(44) | .9500 |
| C(12)—C(11) | 1.538(8) | C(27)—C(28) | 1.404(8) | C(45)—C(46) | 1.370(8) |
| C(13)—H(13A) | .9800 | C(27)—C(33) | 1.413(9) | C(45)—H(45) | .9500 |
| C(13)—H(13B) | .9800 | C(28)—C(47) | 1.372(8) | C(46)—H(46) | .9500 |
| C(13)—H(13C) | .9800 | C(29)—C(33) | 1.375(8) | C(47)—C(48) | 1.378(8) |
| C(14)—H(14A) | .9800 | C(29)—C(30) | 1.478(8) | C(47)—H(47) | .9500 |
| C(14)—H(14B) | .9800 | C(30)—C(40) | 1.515(8) | C(48)—H(48) | .9500 |

Table 27B: (Table 27A continued) Bond lengths [Å] and angles [deg] for crystalline form D.

| | bond lengths [Å] and angles [deg] | | bond lengths [Å] and angles [deg] |
|---|---|---|---|
| C(7)—O(1)—C(6) | 114.6(4) | C(31)—O(2)—C(30) | 117.6(5) |
| C(4)—N(1)—C(5) | 108.2(5) | C(28)—N(3)—C(29) | 109.1(5) |
| C(4)—N(1)—H(1) | 125.9 | C(28)—N(3)—H(3) | 125.4 |
| C(5)—N(1)—H(1) | 125.9 | C(29)—N(3)—H(3) | 125.4 |
| C(13)—N(2)—C(14) | 108.3(4) | C(38)—N(4)—C(37) | 109.8(4) |
| C(13)—N(2)—C(12) | 114.0(5) | C(38)—N(4)—C(36) | 114.0(4) |
| C(14)—N(2)—C(12) | 115.5(5) | C(37)—N(4)—C(36) | 112.8(4) |
| C(13)—N(2)—H(2) | 106.1 | C(38)—N(4)—H(4) | 106.6 |
| C(14)—N(2)—H(2) | 106.1 | C(37)—N(4)—H(4) | 106.6 |
| C(12)—N(2)—H(2) | 106.1 | C(36)—N(4)—H(4) | 106.6 |
| C(2)—C(1)—F(1) | 118.7(6) | F(2)—C(25)—C(26) | 119.9(6) |
| C(2)—C(1)—C(24) | 124.5(6) | F(2)—C(25)—C(48) | 116.1(6) |
| F(1)—C(1)—C(24) | 116.8(6) | C(26)—C(25)—C(48) | 124.0(6) |
| C(1)—C(2)—C(3) | 117.2(6) | C(25)—C(26)—C(27) | 117.5(6) |
| C(1)—C(2)—H(2A) | 121.4 | C(25)—C(26)—H(26) | 121.2 |
| C(3)—C(2)—H(2A) | 121.4 | C(27)—C(26)—H(26) | 121.2 |
| C(4)—C(3)—C(2) | 118.6(6) | C(26)—C(27)—C(28) | 118.7(6) |
| C(4)—C(3)—C(9) | 106.7(5) | C(26)—C(27)—C(33) | 134.0(6) |
| C(2)—C(3)—C(9) | 134.8(5) | C(28)—C(27)—C(33) | 107.3(5) |
| N(1)—C(4)—C(23) | 131.3(5) | N(3)—C(28)—C(47) | 129.9(6) |
| N(1)—C(4)—C(3) | 107.9(5) | N(3)—C(28)—C(27) | 107.5(5) |
| C(23)—C(4)—C(3) | 120.8(5) | C(47)—C(28)—C(27) | 122.6(6) |
| C(9)—C(5)—N(1) | 110.2(5) | N(3)—C(29)—C(33) | 109.0(5) |
| C(9)—C(5)—C(6) | 126.4(5) | N(3)—C(29)—C(30) | 124.4(5) |
| N(1)—C(5)—C(6) | 123.4(5) | C(33)—C(29)—C(30) | 126.6(5) |
| O(1)—C(6)—C(5) | 107.7(4) | O(2)—C(30)—C(29) | 108.7(4) |
| O(1)—C(6)—C(16) | 111.3(5) | O(2)—C(30)—C(40) | 109.4(5) |
| C(5)—C(6)—C(16) | 112.3(5) | C(29)—C(30)—C(40) | 112.0(5) |
| O(1)—C(6)—C(10) | 104.4(5) | O(2)—C(30)—C(34) | 105.7(4) |
| C(5)—C(6)—C(10) | 110.7(5) | C(29)—C(30)—C(34) | 110.7(5) |
| C(16)—C(6)—C(10) | 110.1(4) | C(40)—C(30)—C(34) | 110.2(4) |
| O(1)—C(7)—C(8) | 112.5(5) | O(2)—C(31)—C(32) | 110.5(6) |
| O(1)—C(7)—H(7A) | 109.1 | O(2)—C(31)—H(31A) | 109.5 |
| C(8)—C(7)—H(7A) | 109.1 | C(32)—C(31)—H(31A) | 109.5 |
| O(1)—C(7)—H(7B) | 109.1 | O(2)—C(31)—H(31B) | 109.5 |
| C(8)—C(7)—H(7B) | 109.1 | C(32)—C(31)—H(31B) | 109.5 |
| H(7A)—C(7)—H(7B) | 107.8 | H(31A)—C(31)—H(31B) | 108.1 |
| C(9)—C(8)—C(7) | 107.9(5) | C(33)—C(32)—C(31) | 107.4(5) |
| C(9)—C(8)—H(8A) | 110.1 | C(33)—C(32)—H(32A) | 110.2 |
| C(7)—C(8)—H(8A) | 110.1 | C(31)—C(32)—H(32A) | 110.2 |
| C(9)—C(8)—H(8B) | 110.1 | C(33)—C(32)—H(32B) | 110.2 |
| C(7)—C(8)—H(8B) | 110.1 | C(31)—C(32)—H(32B) | 110.2 |
| H(8A)—C(8)—H(8B) | 108.4 | H(32A)—C(32)—H(32B) | 108.5 |
| C(5)—C(9)—C(3) | 107.1(5) | C(29)—C(33)—C(27) | 107.1(5) |
| C(5)—C(9)—C(8) | 121.0(5) | C(29)—C(33)—C(32) | 119.2(6) |
| C(3)—C(9)—C(8) | 131.9(5) | C(27)—C(33)—C(32) | 133.7(5) |
| C(6)—C(16)—C(15) | 114.5(5) | C(35)—C(34)—C(30) | 112.6(5) |
| C(6)—C(16)—H(16A) | 108.6 | C(35)—C(34)—H(34A) | 109.1 |
| C(15)—C(16)—H(16A) | 108.6 | C(30)—C(34)—H(34A) | 109.1 |
| C(6)—C(16)—H(16B) | 108.6 | C(35)—C(34)—H(34B) | 109.1 |
| C(15)—C(16)—H(16B) | 108.6 | C(30)—C(34)—H(34B) | 109.1 |
| H(16A)—C(16)—H(16B) | 107.6 | H(34A)—C(34)—H(34B) | 107.8 |
| C(16)—C(15)—C(12) | 114.7(5) | C(34)—C(35)—C(36) | 115.1(4) |
| C(16)—C(15)—H(15A) | 108.6 | C(34)—C(35)—H(35A) | 108.5 |
| C(12)—C(15)—H(15A) | 108.6 | C(36)—C(35)—H(35A) | 108.5 |
| C(16)—C(15)—H(15B) | 108.6 | C(34)—C(35)—H(35B) | 108.5 |
| C(12)—C(15)—H(15B) | 108.6 | C(36)—C(35)—H(35B) | 108.5 |
| H(15A)—C(15)—H(15B) | 107.6 | H(35A)—C(35)—H(35B) | 107.5 |

TABLE 27A-continued

| | | | |
|---|---|---|---|
| C(17)—C(12)—C(15) | 112.1(5) | C(41)—C(36)—C(39) | 113.5(5) |
| C(17)—C(12)—C(11) | 112.8(5) | C(41)—C(36)—C(35) | 112.9(4) |
| C(15)—C(12)—C(11) | 106.4(4) | C(39)—C(36)—C(35) | 106.2(4) |
| C(17)—C(12)—N(2) | 107.4(4) | C(41)—C(36)—N(4) | 108.6(4) |
| C(15)—C(12)—N(2) | 108.3(5) | C(39)—C(36)—N(4) | 107.4(4) |
| C(11)—C(12)—N(2) | 109.8(5) | C(35)—C(36)—N(4) | 107.9(4) |
| N(2)—C(13)—H(13A) | 109.5 | N(4)—C(37)—H(37A) | 109.5 |
| N(2)—C(13)—H(13B) | 109.5 | N(4)—C(37)—H(37B) | 109.5 |
| H(13A)—C(13)—H(13B) | 109.5 | H(37A)—C(37)—H(37B) | 109.5 |
| N(2)—C(13)—H(13C) | 109.5 | N(4)—C(37)—H(37C) | 109.5 |
| H(13A)—C(13)—H(13C) | 109.5 | H(37A)—C(37)—H(37C) | 109.5 |
| H(13B)—C(13)—H(13C) | 109.5 | H(37B)—C(37)—H(37C) | 109.5 |
| N(2)—C(14)—H(14A) | 109.5 | N(4)—C(38)—H(38A) | 109.5 |
| N(2)—C(14)—H(14B) | 109.5 | N(4)—C(38)—H(38B) | 109.5 |
| H(14A)—C(14)—H(14B) | 109.5 | H(38A)—C(38)—H(38B) | 109.5 |
| N(2)—C(14)—H(14C) | 109.5 | N(4)—C(38)—H(38C) | 109.5 |
| H(14A)—C(14)—H(14C) | 109.5 | H(38A)—C(38)—H(38C) | 109.5 |
| H(14B)—C(14)—H(14C) | 109.5 | H(38B)—C(38)—H(38C) | 109.5 |
| C(10)—C(11)—C(12) | 113.6(5) | C(40)—C(39)—C(36) | 114.9(5) |
| C(10)—C(11)—H(11A) | 108.9 | C(40)—C(39)—H(39A) | 108.5 |
| C(12)—C(11)—H(11A) | 108.9 | C(36)—C(39)—H(39A) | 108.5 |
| C(10)—C(11)—H(11B) | 108.9 | C(40)—C(39)—H(39B) | 108.5 |
| C(12)—C(11)—H(11B) | 108.9 | C(36)—C(39)—H(39B) | 108.5 |
| H(11A)—C(11)—H(11B) | 107.7 | H(39A)—C(39)—H(39B) | 107.5 |
| C(11)—C(10)—C(6) | 112.9(5) | C(39)—C(40)—C(30) | 113.9(5) |
| C(11)—C(10)—H(10A) | 109.0 | C(39)—C(40)—H(40A) | 108.8 |
| C(6)—C(10)—H(10A) | 109.0 | C(30)—C(40)—H(40A) | 108.8 |
| C(11)—C(10)—H(10B) | 109.0 | C(39)—C(40)—H(40B) | 108.8 |
| C(6)—C(10)—H(10B) | 109.0 | C(30)—C(40)—H(40B) | 108.8 |
| H(10A)—C(10)—H(10B) | 107.8 | H(40A)—C(40)—H(40B) | 107.7 |
| C(22)—C(17)—C(18) | 117.6(5) | C(46)—C(41)—C(42) | 115.9(5) |
| C(22)—C(17)—C(12) | 121.5(5) | C(46)—C(41)—C(36) | 122.2(5) |
| C(18)—C(17)—C(12) | 120.9(5) | C(42)—C(41)—C(36) | 121.9(5) |
| C(19)—C(18)—C(17) | 120.6(6) | C(43)—C(42)—C(41) | 121.0(6) |
| C(19)—C(18)—H(18) | 119.7 | C(43)—C(42)—H(42) | 119.5 |
| C(17)—C(18)—H(18) | 119.7 | C(41)—C(42)—H(42) | 119.5 |
| C(18)—C(19)—C(20) | 121.1(6) | C(42)—C(43)—C(44) | 121.3(6) |
| C(18)—C(19)—H(19) | 119.5 | C(42)—C(43)—H(43) | 119.3 |
| C(20)—C(19)—H(19) | 119.5 | C(44)—C(43)—H(43) | 119.3 |
| C(21)—C(20)—C(19) | 119.1(6) | C(45)—C(44)—C(43) | 119.5(6) |
| C(21)—C(20)—H(20) | 120.4 | C(45)—C(44)—H(44) | 120.3 |
| C(19)—C(20)—H(20) | 120.4 | C(43)—C(44)—H(44) | 120.3 |
| C(20)—C(21)—C(22) | 120.5(6) | C(44)—C(45)—C(46) | 119.3(6) |
| C(20)—C(21)—H(21) | 119.7 | C(44)—C(45)—H(45) | 120.4 |
| C(22)—C(21)—H(21) | 119.7 | C(46)—C(45)—H(45) | 120.4 |
| C(21)—C(22)—C(17) | 121.1(6) | C(45)—C(46)—C(41) | 123.0(6) |
| C(21)—C(22)—H(22) | 119.5 | C(45)—C(46)—H(46) | 118.5 |
| C(17)—C(22)—H(22) | 119.5 | C(41)—C(46)—H(46) | 118.5 |
| C(24)—C(23)—C(4) | 120.3(6) | C(28)—C(47)—C(48) | 119.0(6) |
| C(24)—C(23)—H(23) | 119.8 | C(28)—C(47)—H(47) | 120.5 |
| C(4)—C(23)—H(23) | 119.8 | C(48)—C(47)—H(47) | 120.5 |
| C(23)—C(24)—C(1) | 118.7(6) | C(47)—C(48)—C(25) | 118.2(6) |
| C(23)—C(24)—H(24) | 120.7 | C(47)—C(48)—H(48) | 120.9 |
| C(1)—C(24)—H(24) | 120.7 | C(25)—C(48)—H(48) | 120.9 |

TABLE 28

Hydrogen coordinates (×10⁴) (i.e. (×10^4)) and isotropic displacement parameters (²×10³) (i.e. (² × 10^3)) for crystalline form D.

| | x | y | z | U(eq) |
|---|---|---|---|---|
| H(1) | 4131 | −997 | 6486 | 32 |
| H(2) | 2379 | 1682 | 6164 | 32 |
| H(2A) | 9130 | −3559 | 6323 | 35 |
| H(7A) | 8834 | 1095 | 5640 | 34 |
| H(7B) | 7785 | 636 | 5199 | 34 |
| H(8A) | 9231 | −1065 | 5665 | 36 |
| H(8B) | 9045 | −609 | 6461 | 36 |
| H(16A) | 4111 | 833 | 5493 | 34 |
| H(16B) | 5544 | 1071 | 5050 | 34 |
| H(15A) | 3729 | 2795 | 4978 | 33 |
| H(15B) | 5067 | 3038 | 5299 | 33 |
| H(13A) | 420 | 2378 | 5638 | 48 |
| H(13B) | 1659 | 2845 | 5115 | 48 |
| H(13C) | 621 | 3726 | 5634 | 48 |
| H(14A) | 848 | 3479 | 6962 | 45 |
| H(14B) | 1763 | 2252 | 7300 | 45 |
| H(14C) | 391 | 2233 | 6922 | 45 |
| H(11A) | 5030 | 3047 | 6664 | 32 |
| H(11B) | 3635 | 2904 | 7180 | 32 |
| H(10A) | 3919 | 916 | 6949 | 28 |
| H(10B) | 5292 | 1111 | 7260 | 28 |
| H(18) | 2380 | 4664 | 7055 | 32 |
| H(19) | 1567 | 6714 | 6895 | 35 |
| H(20) | 1600 | 7757 | 5733 | 38 |
| H(21) | 2399 | 6719 | 4722 | 39 |
| H(22) | 3186 | 4654 | 4866 | 36 |
| H(23) | 4308 | −3458 | 6745 | 36 |
| H(24) | 5877 | −5257 | 6802 | 37 |
| H(3) | 2355 | 11336 | −187 | 31 |
| H(4) | 3240 | 9190 | −1170 | 28 |

TABLE 28-continued

Hydrogen coordinates (×10⁴) (i.e. (×10^4)) and isotropic displacement parameters (²×10³) (i.e. (^2 x 10^3)) for crystalline form D.

| | x | y | z | U(eq) |
|---|---|---|---|---|
| H(26) | 633 | 12369 | 2428 | 38 |
| H(31A) | 1367 | 7744 | 2067 | 69 |
| H(31B) | 443 | 8591 | 1475 | 69 |
| H(32A) | 628 | 9812 | 2389 | 47 |
| H(32B) | 2300 | 9385 | 2328 | 47 |
| H(34A) | 4156 | 9460 | −210 | 28 |
| H(34B) | 4637 | 8802 | 559 | 28 |
| H(35A) | 4426 | 6960 | 251 | 28 |
| H(35B) | 5402 | 7544 | −385 | 28 |
| H(37A) | 2661 | 9118 | −2308 | 46 |
| H(37B) | 1673 | 8467 | −1709 | 46 |
| H(37C) | 2951 | 7685 | −2167 | 46 |
| H(38A) | 5396 | 7747 | −1930 | 41 |
| H(38B) | 5595 | 8591 | −1344 | 41 |
| H(38C) | 4976 | 9174 | −2097 | 41 |
| H(39A) | 1356 | 7621 | −703 | 30 |
| H(39B) | 1925 | 7004 | 54 | 30 |
| H(40A) | 582 | 8868 | 233 | 32 |
| H(40B) | 1478 | 9496 | −424 | 32 |
| H(42) | 6051 | 6119 | −1047 | 30 |
| H(43) | 6698 | 4282 | −1494 | 37 |
| H(44) | 5039 | 3278 | −1755 | 39 |
| H(45) | 2675 | 4105 | −1527 | 36 |
| H(46) | 2011 | 5962 | −1104 | 34 |
| H(47) | 1661 | 13737 | −50 | 33 |
| H(48) | 806 | 15112 | 812 | 39 |

TABLE 29

Anisotropic displacement parameters (²×10³) (i.e. (^2 x 10^3)) for crystalline form D. The anisotropic displacement factor exponent takes the form: −2 pi^2 [h^2 a*^2 U11 + ... + 2 h k a* b* U12].

| | U11 | U22 | U33 | U23 | U13 | U12 |
|---|---|---|---|---|---|---|
| F(1) | 40(2) | 27(2) | 57(3) | −6(2) | −2(2) | 8(2) |
| O(1) | 16(2) | 34(2) | 27(2) | −6(2) | 7(2) | 1(2) |
| N(1) | 16(3) | 31(3) | 28(3) | −4(2) | 7(2) | 0(2) |
| N(2) | 20(3) | 27(3) | 29(3) | −4(2) | 3(2) | 3(2) |
| C(1) | 32(4) | 25(3) | 34(4) | −4(3) | −7(3) | 8(3) |
| C(2) | 20(3) | 35(4) | 28(3) | −5(3) | 0(3) | 3(3) |
| C(3) | 19(3) | 29(3) | 23(3) | −7(3) | −1(2) | 5(2) |
| C(4) | 23(3) | 34(4) | 19(3) | −3(3) | 3(2) | 3(3) |
| C(5) | 29(3) | 31(3) | 16(3) | −3(3) | 3(2) | −2(3) |
| C(6) | 16(3) | 34(4) | 29(3) | −2(3) | 3(2) | −2(3) |
| C(7) | 22(3) | 35(4) | 28(3) | 0(3) | 1(2) | −5(3) |
| C(8) | 19(3) | 31(3) | 37(4) | −8(3) | 1(3) | 2(3) |
| C(9) | 10(3) | 33(4) | 22(3) | −5(2) | 2(2) | 3(2) |
| C(16) | 28(3) | 30(3) | 23(3) | −5(3) | 6(3) | −3(3) |
| C(15) | 26(3) | 28(3) | 25(3) | −4(3) | 2(2) | 0(3) |
| C(12) | 19(3) | 29(3) | 24(3) | −1(3) | 3(2) | −1(2) |
| C(13) | 28(3) | 38(4) | 28(3) | −2(3) | −2(3) | −3(3) |
| C(14) | 21(3) | 37(4) | 29(3) | −4(3) | 2(3) | 0(3) |
| C(11) | 21(3) | 32(3) | 24(3) | −10(3) | 5(2) | −1(3) |
| C(10) | 19(3) | 34(3) | 14(3) | −2(2) | −2(2) | 0(2) |
| C(17) | 13(3) | 27(3) | 37(4) | −7(3) | 3(2) | 2(2) |
| C(18) | 18(3) | 29(3) | 33(3) | −4(3) | −2(2) | −2(3) |
| C(19) | 17(3) | 35(4) | 35(4) | −7(3) | −2(3) | 1(3) |
| C(20) | 11(3) | 24(3) | 55(4) | −6(3) | 0(3) | 6(2) |
| C(21) | 17(3) | 35(4) | 41(4) | 3(3) | −1(3) | −1(3) |
| C(22) | 22(3) | 30(3) | 33(4) | −3(3) | 1(3) | 1(3) |
| C(23) | 18(3) | 36(4) | 34(4) | −7(3) | 4(3) | −6(3) |
| C(24) | 36(4) | 31(4) | 26(3) | −5(3) | −2(3) | −6(3) |
| F(2) | 44(2) | 48(2) | 38(2) | −19(2) | 0(2) | 9(2) |
| O(2) | 27(2) | 36(2) | 23(2) | −2(2) | 4(2) | −2(2) |
| N(3) | 17(3) | 35(3) | 23(3) | −8(2) | 6(2) | −1(2) |
| N(4) | 12(3) | 29(3) | 25(3) | −4(2) | 2(2) | 1(2) |
| C(25) | 19(3) | 45(4) | 37(4) | −20(3) | 6(3) | 5(3) |
| C(26) | 20(3) | 47(4) | 25(3) | −9(3) | 0(3) | 6(3) |
| C(27) | 7(3) | 43(4) | 27(3) | −8(3) | −1(2) | 3(2) |
| C(28) | 12(3) | 34(4) | 35(4) | −7(3) | −1(2) | −2(2) |
| C(29) | 13(3) | 36(4) | 26(3) | −2(3) | −1(2) | −2(2) |

TABLE 29-continued

Anisotropic displacement parameters (²×10³) (i.e. (^2 x 10^3)) for crystalline form D. The anisotropic displacement factor exponent takes the form: −2 pi^2 [h^2 a*^2 U11 + ... + 2 h k a* b* U12].

| | U11 | U22 | U33 | U23 | U13 | U12 |
|---|---|---|---|---|---|---|
| C(30) | 15(3) | 32(3) | 22(3) | −2(3) | 3(2) | −1(2) |
| C(31) | 49(5) | 57(5) | 58(5) | 5(4) | 12(4) | −5(4) |
| C(32) | 41(4) | 42(4) | 24(3) | −4(3) | 3(3) | 11(3) |
| C(33) | 15(3) | 41(4) | 24(3) | −6(3) | −1(2) | 5(3) |
| C(34) | 11(3) | 28(3) | 27(3) | −2(3) | 2(2) | 0(2) |
| C(35) | 11(3) | 35(3) | 22(3) | −3(3) | 1(2) | 0(2) |
| C(36) | 16(3) | 30(3) | 22(3) | 3(2) | 0(2) | −1(2) |
| C(37) | 29(3) | 36(4) | 25(3) | 2(3) | −8(3) | −3(3) |
| C(38) | 19(3) | 35(4) | 23(3) | 3(3) | 3(2) | −3(3) |
| C(39) | 19(3) | 30(3) | 25(3) | −2(3) | 1(2) | −2(2) |
| C(40) | 16(3) | 32(3) | 28(3) | 0(3) | 2(2) | 0(2) |
| C(41) | 19(3) | 33(3) | 19(3) | 4(2) | 0(2) | −4(3) |
| C(42) | 20(3) | 27(3) | 25(3) | −1(3) | −1(2) | −2(2) |
| C(43) | 24(3) | 40(4) | 22(3) | −1(3) | 1(3) | 4(3) |
| C(44) | 46(4) | 26(3) | 24(3) | −3(3) | −4(3) | 0(3) |
| C(45) | 32(4) | 35(4) | 23(3) | −3(3) | −1(3) | −10(3) |
| C(46) | 23(3) | 37(4) | 24(3) | 0(3) | −2(3) | −5(3) |
| C(47) | 14(3) | 33(4) | 34(3) | −8(3) | 3(2) | −2(3) |
| C(48) | 18(3) | 36(4) | 43(4) | −7(3) | −1(3) | −2(3) |
| Cl(1) | 21(1) | 31(1) | 35(1) | −4(1) | −1(1) | 0(1) |
| Cl(2) | 42(1) | 31(1) | 24(1) | −1(1) | −1(1) | −3(1) |

TABLE 30

Conformation of crystalline form D.

| bond | distance | angle with plane normal | orientation |
|---|---|---|---|
| C(6)—O(1) | 1.436(7) | 7.1(3) | Ax |
| C(6)—C(5) | 1.487(8) | 66.8(4) | Eq |
| C(12)—N(2) | 1.538(8) | 1.6(4) | Ax |
| C(12)—C(17) | 1.527(8) | 70.9(4) | Eq |

TABLE 31

Geometry of hydrogen bonds of crystalline form D.

| bond | D-H | H...A | D...A | D-H...A |
|---|---|---|---|---|
| N(1)—H(1)...Cl(1) | 0.88 | 2.29 | 3.148(5) | 164 |
| N(2)—H(2)...Cl(1) | 0.93 | 2.21 | 3.029(5) | 147 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A crystalline form of (1r,4r)-6'-fluoro-N,N-dimethyl-4-phenyl-4',9'-dihydro-3'H-spiro[cyclohexane-1,1'-pyrano[3,4,b]indol]-4-amine hydrochloride, which has
one or more X-ray diffraction peaks (CuKα radiation) selected from the group consisting of 10.6±0.2 (2Θ), 17.2±0.2 (2Θ), 18.6±0.2 (2Θ), 19.3±0.2 (2Θ), 22.2±0.2 (2Θ), 26.7±0.2 (2Θ), 29.3±0.2 (2Θ); and/or one or more Raman peaks selected from the group consisting of 183±2 cm$^{-1}$, 919±2 cm$^{-1}$, 1001±2 cm$^{-1}$, 1300±2 cm$^{-1}$, 1569±2 cm$^{-1}$, 1583±2 cm$^{-1}$, 2992±2 cm$^{-1}$, 3054±2 cm$^{-1}$ and 3069±2 cm$^{-1}$.

2. The crystalline form according to claim 1, which is an ansolvate.

3. The crystalline form according to claim 1, which upon DSC analysis exhibits an endothermal event with an onset temperature or a peak temperature in the range of 262-270° C.

4. A pharmaceutical composition comprising the crystalline form according to claim 1 and at least one pharmaceutically acceptable carrier or auxiliary.

5. A process for obtaining a solid form of (1r,4r)-6'-fluoro-N,N-dimethyl-4-phenyl-4',9'-dihydro-3'H-spiro[cyclohexane-1,1'-pyrano[3,4,b]indol]-4-amine hydrochloride according to claim 1, said process comprising:
- (a-1) adding hydrogen chloride to a solution or suspension of the free base (1r,4r)-6'-fluoro-N,N-dimethyl-4-phenyl-4',9'-dihydro-3'H-spiro[cyclohexane-1,1'-pyrano[3,4,b]indol]-4-amine in a mixture of acetone and THF to form the hydrochloride salt of (1r,4r)-6'-fluoro-N,N-dimethyl-4-phenyl-4',9'-dihydro-3'H-spiro[cyclohexane-1,1'-pyrano[3,4,b]indol]-4-amine, wherein the mixture comprises acetone and THF in a ratio from 100:1 to 1:1 and the addition is carried out at a temperature at or below the boiling point of the mixture; and
- (b-1) stirring the solution or suspension for at least 1 hour to precipitate (1r,4r)-6'-fluoro-N,N-dimethyl-4-phenyl-4',9'-dihydro-3'H-spiro[cyclohexane-1,1'-pyrano[3,4,b)]indol]-4-amine hydrochloride from the solution or suspension; and
- (c-1) separating the precipitated salt;

or

- (a-2) dissolving (1r,4r)-6'-fluoro-N,N-dimethyl-4-phenyl-4',9'-dihydro-3'H-spiro-[cyclohexane-1,1'-pyrano[3,4,b]indol]-4-amine hydrochloride in $CH_2Cl_2$ or a mixture of $CH_2Cl_2$ and methanol; and
- (b-2) evaporating the solvent from the solution;

or

- (a-3) suspending solid (1r,4r)-6'-fluoro-N,N-dimethyl-4-phenyl-4',9'-dihydro-3'H-spiro-[cyclohexane-1,1'-pyrano[3,4,b]indol]-4-amine hydrochloride in a solvent mixture selected from acetone/THF/water, $CH_2Cl_2$/methanol, or acetone/THF, and stirring the resulting suspension; and
- (b-3) separating the suspended solid from the suspension.

6. A process according to claim 5, wherein said solid form is a crystalline form.

7. A crystalline form of (1r,4r)-6'-fluoro-N,N-dimethyl-4-phenyl-4',9'-dihydro-3'H-spiro[cyclohexane-1,1'-pyrano[3,4,b]indol]-4-amine hydrochloride according to claim 1, having a CuKα radiation X-ray powder diffraction pattern comprising characteristic peaks at 10.6±0.2 (2Θ), 17.2±0.2 (2Θ), 18.6±0.2 (2Θ), 19.3±0.2 (2Θ), 26.7±0.2 (2Θ), 29.3±0.2 (2Θ) and optionally 22.2±0.2 (2Θ).

8. The crystalline form according to claim 7, wherein the crystalline form has an endothermal event with a peak temperature at about 262-270° C., as determined by DSC.

9. The pharmaceutical composition of claim 4, which comprises between about 0.001% by weight and about 20% by weight of the crystalline form.

* * * * *